US012026900B2

(12) United States Patent
Talbert et al.

(10) Patent No.: US 12,026,900 B2
(45) Date of Patent: Jul. 2, 2024

(54) HYPERSPECTRAL IMAGING IN A LIGHT DEFICIENT ENVIRONMENT

(71) Applicant: Cilag GmbH International, Zug (CH)

(72) Inventors: Joshua D. Talbert, Salt Lake City, UT (US); Donald M. Wichern, Salt Lake City, UT (US)

(73) Assignee: Cllag GmbH International, Zug (CH)

( * ) Notice: Subject to any disclaimer, the term of this patent is extended or adjusted under 35 U.S.C. 154(b) by 1086 days.

(21) Appl. No.: 16/234,360

(22) Filed: Dec. 27, 2018

(65) Prior Publication Data

US 2019/0191977 A1 Jun. 27, 2019

Related U.S. Application Data

(60) Provisional application No. 62/723,989, filed on Aug. 28, 2018, provisional application No. 62/610,888, filed on Dec. 27, 2017.

(51) Int. Cl.
*G06T 7/521* (2017.01)
*A61B 1/00* (2006.01)
(Continued)

(52) U.S. Cl.
CPC ............ *G06T 7/521* (2017.01); *A61B 1/0005* (2013.01); *A61B 1/00066* (2013.01);
(Continued)

(58) Field of Classification Search
CPC ... A61B 1/043; A61B 1/00006; A61B 1/0638; A61B 5/0261; A61B 5/20; A61B 5/4887;
(Continued)

(56) References Cited

U.S. PATENT DOCUMENTS 3,844,047 A 10/1974 Carson
4,556,057 A 12/1985 Hiruma et al.
(Continued)

FOREIGN PATENT DOCUMENTS

CN 111526774 A 8/2020
CN 111526775 A 8/2020
(Continued)

OTHER PUBLICATIONS

English Translation of JP2008259595 prepared by Google Patents (https://patents.google.com/patent/JP2008259595A/en?oq=JP2008259595).
(Continued)

*Primary Examiner* — Nasim N Nirjhar
(74) *Attorney, Agent, or Firm* — TechLaw Ventures, PLLC; Terrence J. Edwards

(57) ABSTRACT

An endoscopic imaging system for use in a light deficient environment includes an imaging device having a tube, one or more image sensors, and a lens assembly including at least one optical elements that corresponds to the one or more image sensors. The endoscopic system includes a display for a user to visualize a scene and an image signal processing controller. The endoscopic system includes a light engine having an illumination source generating one or more pulses of electromagnetic radiation and a lumen transmitting one or more pulses of electromagnetic radiation to a distal tip of an endoscope.

57 Claims, 48 Drawing Sheets

(51) Int. Cl.
  *A61B 1/04* (2006.01)
  *A61B 1/045* (2006.01)
  *A61B 1/05* (2006.01)
  *A61B 1/06* (2006.01)
  *G01J 3/02* (2006.01)
  *G01J 3/10* (2006.01)
  *G01J 3/28* (2006.01)
  *G02B 23/24* (2006.01)
  *H04N 5/265* (2006.01)
  *H04N 5/272* (2006.01)
  *H04N 13/239* (2018.01)
  *H04N 23/10* (2023.01)
  *H04N 23/13* (2023.01)
  *H04N 23/45* (2023.01)
  *H04N 23/56* (2023.01)
  *H04N 23/74* (2023.01)
  *H04N 23/741* (2023.01)
  *H04N 23/84* (2023.01)
  *H04N 25/53* (2023.01)
  *H04N 25/533* (2023.01)
  *H04N 23/50* (2023.01)

(52) U.S. Cl.
  CPC ...... *A61B 1/00096* (2013.01); *A61B 1/00186* (2013.01); *A61B 1/00193* (2013.01); *A61B 1/043* (2013.01); *A61B 1/045* (2013.01); *A61B 1/05* (2013.01); *A61B 1/063* (2013.01); *A61B 1/0638* (2013.01); *A61B 1/0646* (2013.01); *A61B 1/0653* (2013.01); *A61B 1/0661* (2013.01); *G01J 3/027* (2013.01); *G01J 3/10* (2013.01); *G01J 3/2803* (2013.01); *G01J 3/2823* (2013.01); *G02B 23/2461* (2013.01); *G02B 23/2484* (2013.01); *H04N 5/265* (2013.01); *H04N 5/272* (2013.01); *H04N 13/239* (2018.05); *H04N 23/125* (2023.01); *H04N 23/13* (2023.01); *H04N 23/45* (2023.01); *H04N 23/56* (2023.01); *H04N 23/74* (2023.01); *H04N 23/741* (2023.01); *H04N 23/84* (2023.01); *H04N 25/53* (2023.01); *H04N 25/533* (2023.01); *G01J 2003/2826* (2013.01); *G06T 2207/10024* (2013.01); *G06T 2207/10028* (2013.01); *G06T 2207/10068* (2013.01); *G06T 2207/30004* (2013.01); *H04N 23/555* (2023.01)

(58) Field of Classification Search
  CPC ....... A61B 5/489; A61B 5/4893; A61B 1/063; A61B 1/07; A61B 1/000095; A61B 1/045; A61B 1/0646; A61B 1/0655; A61B 5/0071; A61B 5/0084; G01N 21/6456; G01N 2021/6439; G01S 17/89; G01S 7/483; G02B 5/208; G06T 7/0012; G06T 7/20; G06T 7/521; G06T 7/70; G06T 2207/10012; G06T 2207/10016; G06T 2207/10024; G06T 2207/10028; G06T 2207/10036; G06T 2207/10064; G06T 2207/10068; G06T 2207/10152; G06T 2207/20212; G06T 2207/30096; G06T 2207/30101; G06T 2207/30104; H04N 5/2354; H04N 5/2356; H04N 9/04521; H04N 13/239; H04N 2005/2255; H04N 5/2253; H04N 5/2256; H04N 5/3532; H04N 13/214; H04N 13/218; H04N 13/254; H04N 13/257; H04N 5/2355; H04N 5/379
  See application file for complete search history.

(56) References Cited

U.S. PATENT DOCUMENTS

| | | |
|---|---|---|
| 5,318,024 A | 6/1994 | Kittrell et al. |
| 5,363,387 A | 11/1994 | Sinofsky |
| 5,515,449 A | 5/1996 | Tsuruoka et al. |
| 5,749,830 A | 5/1998 | Kaneko et al. |
| 5,784,162 A | 7/1998 | Cabib et al. |
| 6,061,591 A | 5/2000 | Frietag et al. |
| 6,110,106 A | 8/2000 | MacKinnon et al. |
| 6,236,879 B1 | 5/2001 | Konings |
| 6,537,211 B1 | 3/2003 | Wang et al. |
| 6,975,898 B2 | 12/2005 | Seibel |
| 7,826,878 B2 | 11/2010 | Alfano et al. |
| 9,895,054 B2 | 2/2018 | Morimoto et al. |
| 10,588,711 B2 | 3/2020 | Dicarlo et al. |
| 11,006,093 B1 | 5/2021 | Hegyi |
| 11,574,412 B2 | 2/2023 | Talbert et al. |
| 2001/0000317 A1 | 4/2001 | Yoneya et al. |
| 2002/0016533 A1 | 2/2002 | Marchitto et al. |
| 2002/0065468 A1 | 5/2002 | Utzinger et al. |
| 2002/0120182 A1 | 8/2002 | Muessig et al. |
| 2002/0123666 A1 | 9/2002 | Matsumoto |
| 2002/0138008 A1 | 9/2002 | Tsujita et al. |
| 2002/0139920 A1 | 10/2002 | Seibel et al. |
| 2002/0161282 A1 | 10/2002 | Fulghum |
| 2003/0058440 A1 | 3/2003 | Scott et al. |
| 2003/0059108 A1 | 3/2003 | Hubel |
| 2003/0100824 A1 | 5/2003 | Warren et al. |
| 2003/0153825 A1 | 8/2003 | Mooradian et al. |
| 2003/0223248 A1 | 12/2003 | Cronin et al. |
| 2004/0010192 A1 | 1/2004 | Benaron et al. |
| 2004/0092958 A1 | 5/2004 | Limonadi et al. |
| 2004/0116800 A1* | 6/2004 | Helfer .................. G01R 33/285 600/411 |
| 2004/0186351 A1 | 9/2004 | Imaizumi et al. |
| 2004/0234152 A1 | 11/2004 | Liege et al. |
| 2005/0020926 A1 | 1/2005 | Wiklof et al. |
| 2005/0107808 A1 | 5/2005 | Evans et al. |
| 2005/0205758 A1 | 9/2005 | Almeida |
| 2006/0069314 A1 | 3/2006 | Farr |
| 2006/0241499 A1 | 10/2006 | Irion et al. |
| 2006/0276966 A1 | 12/2006 | Cotton et al. |
| 2007/0016077 A1 | 1/2007 | Nakaoka et al. |
| 2007/0046778 A1 | 3/2007 | Ishihara et al. |
| 2007/0057211 A1 | 3/2007 | Bahlman et al. |
| 2007/0086495 A1 | 4/2007 | Sprague et al. |
| 2007/0177009 A1 | 8/2007 | Bayer et al. |
| 2007/0242330 A1 | 10/2007 | Rosman et al. |
| 2007/0276234 A1 | 11/2007 | Shahidi |
| 2008/0058629 A1 | 3/2008 | Seibel et al. |
| 2008/0081950 A1 | 4/2008 | Koenig et al. |
| 2008/0090220 A1 | 4/2008 | Freeman et al. |
| 2008/0177139 A1 | 7/2008 | Courtney et al. |
| 2008/0177140 A1 | 7/2008 | Cline et al. |
| 2008/0192231 A1 | 8/2008 | Jureller et al. |
| 2008/0249368 A1 | 10/2008 | Takei |
| 2009/0118578 A1 | 5/2009 | Takasugi et al. |
| 2009/0289200 A1 | 11/2009 | Ishii |
| 2009/0303317 A1 | 12/2009 | Tesar |
| 2009/0306478 A1 | 12/2009 | Mizuyoshi |
| 2010/0049180 A1 | 2/2010 | Wells et al. |
| 2010/0056928 A1* | 3/2010 | Zuzak ...................... G01J 3/10 356/302 |
| 2010/0128109 A1 | 5/2010 | Banks |
| 2010/0157039 A1 | 6/2010 | Sugai |
| 2010/0160917 A1 | 6/2010 | Fitz et al. |
| 2010/0168585 A1 | 7/2010 | Fujii et al. |
| 2010/0261958 A1 | 10/2010 | Webb et al. |
| 2010/0262017 A1 | 10/2010 | Frangioni |
| 2010/0277087 A1 | 11/2010 | Ikeda |
| 2010/0297659 A1 | 11/2010 | Yoo |
| 2011/0087212 A1 | 4/2011 | Aldridge et al. |
| 2011/0196355 A1 | 8/2011 | Mitchell et al. |
| 2011/0270092 A1 | 11/2011 | Kang et al. |
| 2011/0280810 A1 | 11/2011 | Hauger et al. |
| 2012/0010465 A1 | 1/2012 | Erikawa et al. |
| 2012/0062722 A1 | 3/2012 | Sase |

(56) References Cited

U.S. PATENT DOCUMENTS

| | | | |
|---|---|---|---|
| 2012/0123205 A1 | 5/2012 | Nie et al. | |
| 2012/0273470 A1 | 11/2012 | Zediker et al. | |
| 2012/0294498 A1 | 11/2012 | Popovic | |
| 2013/0085484 A1 | 4/2013 | Van Valen et al. | |
| 2013/0176395 A1 | 7/2013 | Kazakevich | |
| 2013/0188383 A1 | 7/2013 | Jaffe et al. | |
| 2013/0211246 A1 | 8/2013 | Parasher | |
| 2013/0211391 A1* | 8/2013 | BenYakar | A61B 18/20 606/10 |
| 2013/0324797 A1 | 12/2013 | Igarashi et al. | |
| 2014/0073885 A1 | 3/2014 | Frangioni | |
| 2014/0163319 A1* | 6/2014 | Blanquart | A61B 1/051 600/109 |
| 2014/0276093 A1 | 9/2014 | Zeien | |
| 2014/0300750 A1 | 10/2014 | Nagume | |
| 2014/0336501 A1 | 11/2014 | Masumoto | |
| 2015/0030542 A1 | 1/2015 | Singhal | |
| 2015/0073209 A1 | 3/2015 | Ikeda | |
| 2015/0305604 A1 | 10/2015 | Melsky | |
| 2015/0309284 A1 | 10/2015 | Kagawa et al. | |
| 2016/0006914 A1 | 1/2016 | Neumann | |
| 2016/0022126 A1 | 1/2016 | Ramesh et al. | |
| 2016/0062103 A1 | 3/2016 | Yang et al. | |
| 2016/0183775 A1 | 6/2016 | Blanquart et al. | |
| 2016/0195706 A1 | 7/2016 | Fujii | |
| 2016/0335778 A1 | 11/2016 | Smits | |
| 2017/0035280 A1 | 2/2017 | Yang et al. | |
| 2017/0059305 A1 | 3/2017 | Nonn et al. | |
| 2017/0071472 A1 | 3/2017 | Zeng et al. | |
| 2017/0086940 A1 | 3/2017 | Nakamura | |
| 2017/0163971 A1 | 6/2017 | Wang et al. | |
| 2017/0167980 A1 | 6/2017 | Dimitriadis et al. | |
| 2017/0205198 A1 | 7/2017 | Roncone et al. | |
| 2017/0209050 A1 | 7/2017 | Fengler et al. | |
| 2017/0232269 A1 | 8/2017 | Luttrull et al. | |
| 2017/0280029 A1 | 9/2017 | Steiner | |
| 2017/0280970 A1 | 10/2017 | Sartor et al. | |
| 2017/0293134 A1 | 10/2017 | Otterstrom et al. | |
| 2017/0360275 A1* | 12/2017 | Yoshizaki | G02B 23/2461 |
| 2018/0000401 A1 | 1/2018 | Kang et al. | |
| 2018/0008138 A1* | 1/2018 | Thommen | A61B 17/56 |
| 2018/0014000 A1* | 1/2018 | Blanquart | H04N 5/378 |
| 2018/0020920 A1 | 1/2018 | Ermilov et al. | |
| 2018/0038845 A1 | 2/2018 | Zimmermann et al. | |
| 2018/0217262 A1 | 8/2018 | Albelo et al. | |
| 2018/0234603 A1 | 8/2018 | Moore et al. | |
| 2018/0246313 A1 | 8/2018 | Eshel et al. | |
| 2019/0191974 A1 | 6/2019 | Talbert et al. | |
| 2019/0191975 A1 | 6/2019 | Talbert et al. | |
| 2019/0191976 A1 | 6/2019 | Talbert et al. | |
| 2019/0191978 A1 | 6/2019 | Talbert et al. | |
| 2019/0197712 A1 | 6/2019 | Talbert et al. | |
| 2019/0200848 A1 | 7/2019 | McDowall et al. | |
| 2020/0315439 A1 | 10/2020 | Mizoguchi | |
| 2021/0356757 A1* | 11/2021 | Weigel | G02B 27/48 |

FOREIGN PATENT DOCUMENTS

| | | |
|---|---|---|
| CN | 111526776 A | 8/2020 |
| CN | 111526777 A | 8/2020 |
| CN | 111565620 A | 8/2020 |
| CN | 111601536 A | 8/2020 |
| JP | H02152103 A | 6/1990 |
| JP | H04158205 A | 6/1992 |
| JP | 2002315721 A | 10/2002 |
| JP | 2007029232 A | 2/2007 |
| JP | 2008259595 A | 10/2008 |
| JP | 2010125284 A | 6/2010 |
| JP | 2011206227 A | 10/2011 |
| JP | 2011206435 A | 10/2011 |
| JP | 2012016545 A | 1/2012 |
| JP | 2012019982 A | 2/2012 |
| JP | 2012019983 A | 2/2012 |
| JP | 2012023492 A | 2/2012 |
| JP | 2012105715 A | 6/2012 |
| JP | 2012213550 A | 11/2012 |
| JP | 2015119712 A | 7/2015 |
| JP | 2015119836 A | 7/2015 |
| JP | 2015530893 A | 10/2015 |
| JP | 2015553271 A | 11/2015 |
| JP | 2016007336 A | 1/2016 |
| JP | 2016202726 A | 12/2016 |
| JP | 2018042676 A | 3/2018 |
| WO | 2014018951 A1 | 1/2014 |
| WO | 2014134314 A1 | 9/2014 |
| WO | WO 2015005277 A1 | 1/2015 |
| WO | WO 2015016172 A1 | 2/2015 |
| WO | WO 2015077493 A1 | 5/2015 |
| WO | 2014073138 A1 | 9/2016 |
| WO | 2016203572 A1 | 12/2016 |
| WO | WO 2016189892 A1 | 6/2017 |
| WO | WO 2017201093 A1 | 11/2017 |
| WO | WO 2016185763 A1 | 3/2018 |
| WO | 2019133736 A1 | 7/2019 |
| WO | 2019133737 A1 | 7/2019 |
| WO | 2019133739 A1 | 7/2019 |
| WO | 2019133741 A1 | 7/2019 |
| WO | 2019133750 A1 | 7/2019 |
| WO | 2019133753 A1 | 7/2019 |

OTHER PUBLICATIONS

English Translation of WO2016203572 prepared by Google Patents (https://patents.google.com/patent/WO2016203572A1/en?oq=WO2016203572).

English Translation of CN11526774A prepared by Google Patents (https://patents.google.com/patent/CN111526774A/en?oq=CN+111526774A).

English Translation of CN111526775A prepared by Google Patents (https://patents.google.com/patent/CN111526775A/en?oq=CN111526775).

English Translation of CN111526776 prepared by Google Potents (https://patents.google.com/patent/CN111526776A/en?oq=CN+111526776).

English Translation of CN111526777A prepared by Google Patents (https://patents.google.com/patent/CN111526777A/en?oq=CN+111526777).

English Translation of CN111565620A Prepared by Google Patents (https://patents.google.com/patent/CN111565620A/en?oq=CN111565620).

English Translation of CN111601536A Prepared by Google Patents (https://patents.google.com/patent/CN111601536A/en?oq=CN111601536A).

English Translation of JP H04-158205 prepared by Google Patents (https://patents.google.com/patent/JPH04158205A/en?oq=JPH04158205).

English Translation of JP2002315721 prepared by Google Patents (https://patents.google.com/patent/JP2002315721A/en?oq=JP2002315721).

English Translation of JP 2011206227 prepared by Google Patents (https://patents.google.com/patent/JP2011206227A/en?oq=JP2011206227).

English Translation of JP 2012016545 prepared by Google Patents (https://patents.google.com/patent/JP2012016545A/en?oq=JP2012016545).

English Translation of JP2016007336 prepared by Google Patents (https://patents.google.com/patent/JP2016007336A/en?oq=JP2016007336).

English Translation of WO2014073138 prepared by Google Patents (https://patents.google.com/patent/JPWO2014073138A1/en?oq=WO2014073138).

English Translation of Notification of Reasons for Refusal issued by the Japanese Intellectual Property Office dated Dec. 6, 2022, in connection with Japanese Patent Application No. 2020-536245.

English Translation of JP2012213550 prepared by Google Patents (https://patents.google.com/patent/JP2012213550A/en?oq=JP2012213550).

(56) References Cited

OTHER PUBLICATIONS

English Translation of JP H02152103 Prepared by Google Patents (https://patents.google.com/patent/JPH02152103A/en?oq=JP+H02152103).
English translation of JP2007029232 prepared by Google Patents (https://patents.google.com/patent/JP2007029232A/en?oq=JP2007029232).
English translation of JP 2011206435 prepared by Google Patents (https://patents.google.com/patent/JP2011206435A/en?oq=JP2011206435).
English Translation of JP2012019982 prepared by Google Patents (https://patents.google.com/patent/JP2012019982A/en?oq=JP2012019982).
English Translation of JP 2012019983 prepared by Google Patents (https://patents.google.com/patent/JP2012019983A/en?oq=JP2012019983).
English Translation of JP2012023492 prepared by Google Patents (https://patents.google.com/patent/JP2012023492A/en?oq=JP2012023492).
English Translation of JP2012105715 prepared by Google Patents (https://patents.google.com/patent/JP2012105715A/en?oq=JP2012105715).
English Translation of JP2015119712 prepared by Google Patents (https://patents.google.com/patent/JP2015119712A/en?oq=JP2015119712).
English Translation of JP2015119836 prepared by Google Patents (https://patents.google.com/patent/JP2015119836A/en?oq=JP2015119836).
English translation of JP2015530893 prepared by Google Patents (https://patents.google.com/patent/JP2015530893A/en?oq=JP2015530893).
English translation of JP2015531271 prepared by Google Patents (https://patents.google.com/patent/JP2015531271A/en?oq=JP2015531271).
English Translation of JP2016202726 prepared by Google Patents (https://patents.google.com/patent/JP2016202726A/en?oq=JP+2016202726).
English Translation of JP2018042676 prepared by Google Patents (https://patents.google.com/patent/JP2018042676A/en?oq=JP++2018042676).
English Translation of Notification of Reasons for Refusal issued by the Japanese Intellectual Property Office dated May 5, 2023, in connection with Japanese Patent Application No. 2020-536245.
English Translation of Notification of Reasons for Refusal issued by the Japanese Intellectual Property Office dated Dec. 4, 2022, in connection with Japanese Patent Application No. 2020-536243.
English Translation of Notification of Reasons for Refusal issued by the Japanese Intellectual Property Office dated May 5, 2023, in connection with Japanese Patent Application No. 2020-536243.
English Translation of Notification of Reasons for Refusal issued by the Japanese Intellectual Property Office dated Mar. 14, 2023, in connection with Japanese Patent Application No. 2020-536006.
English Translation of WO 2015005277 prepared by Google Patents (https://patents.google.com/patent/WO2015005277A1/en?oq=WO+2015005277).
English Translation of WO 2015016172 prepared by Google Patents (https://patents.google.com/patent/WO2015016172A1/en?oq=WO+2015016172).
English Translation of WO 2016185763 prepared by Google Patents (https://patents.google.com/patent/JPWO2016185763A1/en?oq=WO+2016185763).
English Translation of WO 2016189892 prepared by Google Patents (https://patents.google.com/patent/JPWO2016189892A1/en?oq=WO+2016189892).

\* cited by examiner

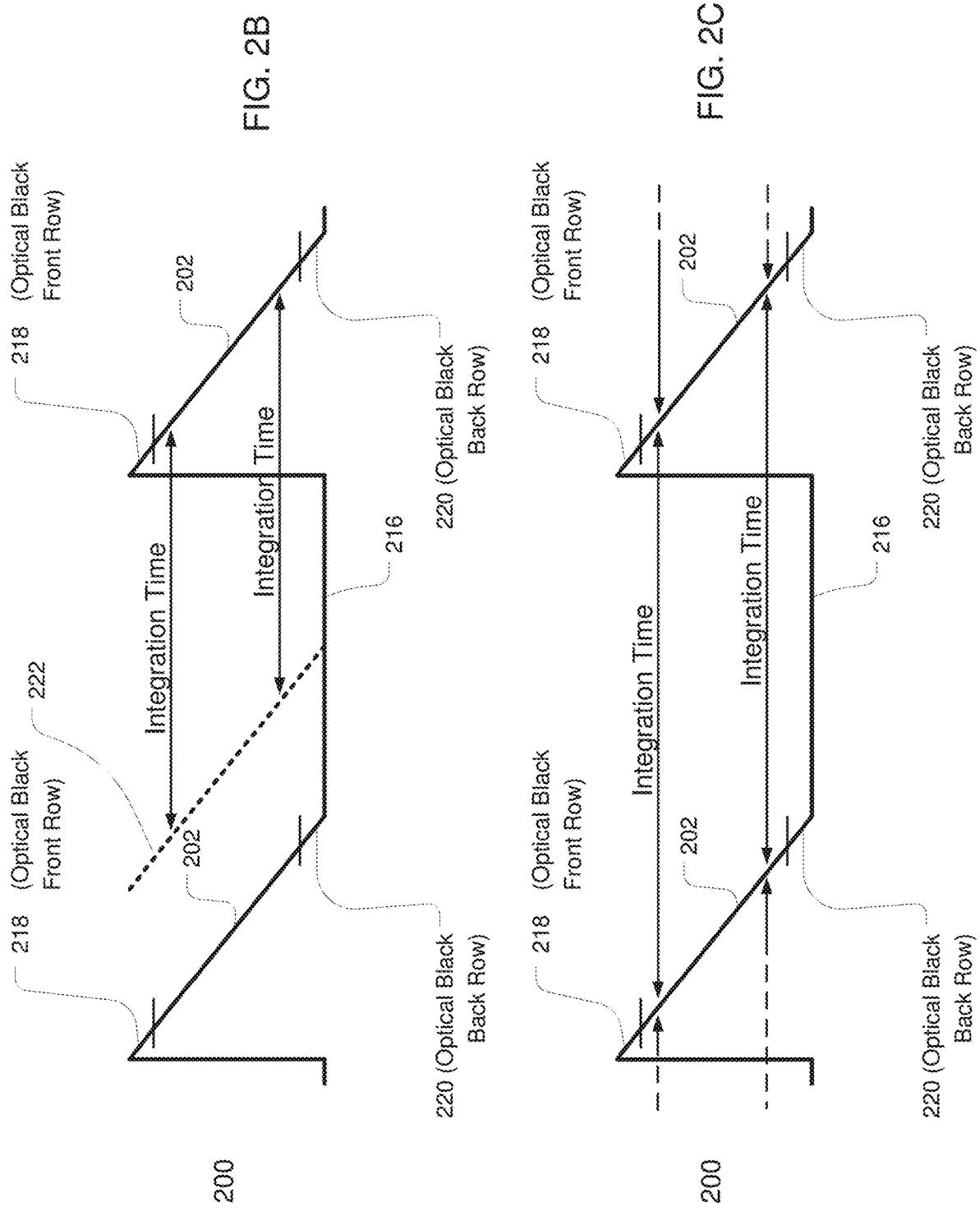

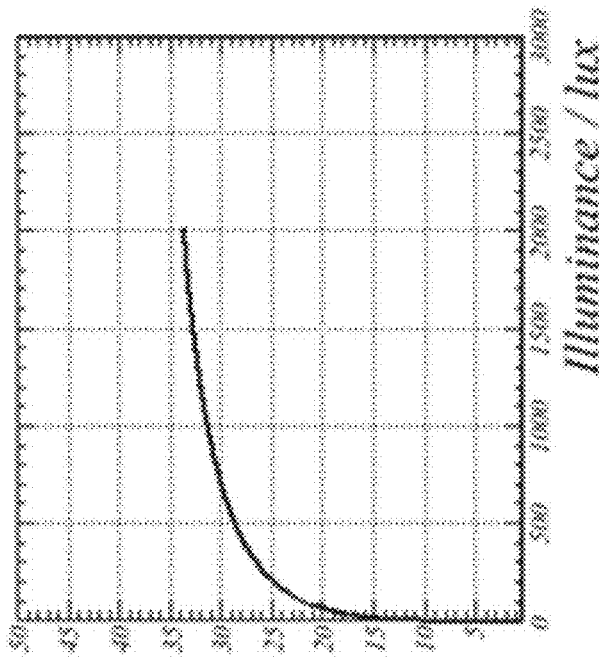
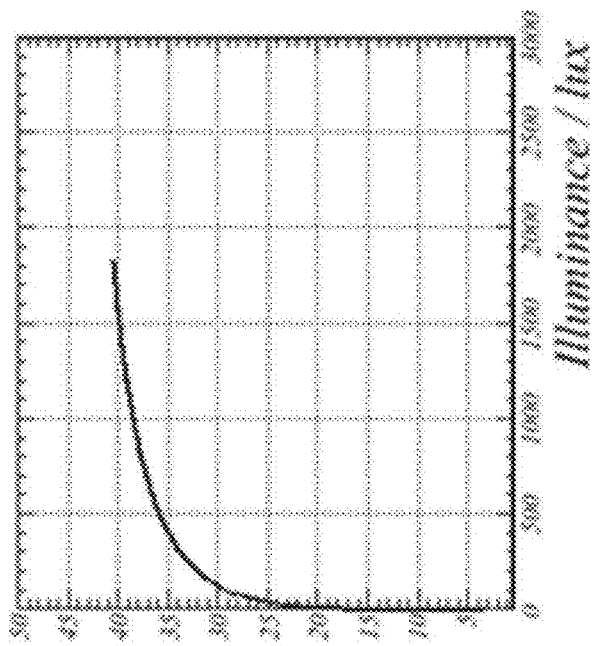
FIG. 24

3D with double pixel array

HYPERSPECTRAL IMAGING IN A LIGHT DEFICIENT ENVIRONMENT

CROSS-REFERENCE TO RELATED APPLICATIONS

This application claims the benefit of U.S. Provisional Patent Application No. 62/610,888, filed Dec. 27, 2017, titled "HYPERSPECTRAL IMAGING IN A LIGHT DEFICIENT ENVIRONMENT," and claims the benefit of U.S. Provisional Patent Application No. 62/723,989, filed Aug. 28, 2018, titled "HYPERSPECTRAL IMAGING IN A LIGHT DEFICIENT ENVIRONMENT," which are incorporated herein by reference in their entireties, including but not limited to those portions that specifically appear hereinafter, the incorporation by reference being made with the following exception: In the event that any portion of the above-referenced provisional applications are inconsistent with this application, this application supersedes the above-referenced provisional applications.

STATEMENT REGARDING FEDERALLY SPONSORED RESEARCH AND DEVELOPMENT

Not applicable.

BACKGROUND

Advances in technology have provided advances in imaging capabilities for medical use. An endoscope may be used to look inside a body and examine the interior of an organ or cavity of the body. Endoscopes may be used for investigating a patient's symptoms, confirming a diagnosis, or providing medical treatment. A medical endoscope may be used for viewing a variety of body systems and parts, including for example, the gastrointestinal tract, the respiratory tract, the urinary tract, the abdominal cavity by way of a small incision, and so forth. Endoscopes may further be used for surgical procedures, such as plastic surgery procedures, procedures performed on joints or bones, procedures performed on the neurological system, procedures performed within the abdominal cavity, and so forth.

Endoscopes have also been used in non-medical fields for viewing and inspecting spaces that may be inaccessible or difficult to see. For example, endoscopes may be used by planners or architects for visualizing scale models of proposed buildings or cities. Endoscopes may be used for visualizing an internal space of a complex system such as a computer. Endoscopes may even be used by law enforcement or military personnel for conducting surveillance in tight spaces or examining explosive devices.

Among the various uses for endoscopes, it may be beneficial to view a space in color. A digital color image may include at least three layers, or "color channels," for each pixel of the image. Each of the color channels measures the intensity and chrominance of light for a spectral band. Commonly, a digital color image includes a color channel for red, green, and blue spectral bands of light (this may be referred to as an RGB image). Each of the red, green, and blue color channels include brightness information for the red, green, or blue spectral band of light. The brightness information for the separate red, green, and blue layers may be combined to create a digital color image. Because a color image is made up of separate layers, a digital camera image sensor commonly includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image.

In the case of endoscopic imaging for medical diagnostics or medical procedures, it may be beneficial or even necessary to view a body cavity with color images. For example, if an endoscope is used to view the abdominal cavity of a body, a color image may provide valuable information to help identify different organs or tissues within the abdomen, or to identify certain conditions or diseases within the space. As discussed above, a digital camera capable of capturing color images may have at least three distinct types of pixel sensors to individually capture the red, green, and blue layers of the color images. The at least three distinct types of pixel sensors may consume a relatively significant physical space (when compared with a color-agnostic pixel array) such that the complete pixel array cannot fit on the small distal end of the endoscope that is inserted into the body. Because color digital cameras may include the at least three distinct types of pixel sensors, the total pixel array (i.e. the image sensor) is commonly located in a hand-piece unit of an endoscope that is held by an endoscope operator and is not placed within the body cavity. For such an endoscope, light is transmitted along the length of the endoscope from the hand-piece unit to the distal end of the endoscope that is placed within the body cavity. This endoscope configuration has significant limitations. Endoscopes with this configuration are delicate and can be easily misaligned or damaged when bumped or impacted during regular use. This can significantly degrade the quality of the images generated by the endoscope and necessitate that the endoscope be frequently repaired or replaced.

Endoscopic imaging may be used to guide a medical practitioner during a medical procedure such as a diagnostic imaging procedure or a surgical procedure. Further in some implementations, it may be desirable to execute a computer-implemented robotic surgery using endoscopic imaging and endoscopic medical devices. In both instances it may be desirable to determine precise measurements indicating distances and/or angles between, for example, structures in the body, devices or tools in the body cavity, and critical structures in the body. Such measurements can improve the outcome of endoscopic procedures and may be necessary in the case of robotic endoscopic procedures.

Various measurement systems and methods exist in the art for applications in archaeology, geography, atmospheric physics, autonomous vehicles, and others. One such system includes light detection and ranging (LIDAR), which is a three-dimensional laser scanning system. LIDAR has been applied in navigation systems such as airplanes or satellites to determine position and orientation of a sensor in combination with other systems and sensors. LIDAR may use active sensors to illuminate an object and detect energy that is reflected off the object and back to a sensor. Laser scanning technology has been applied to airborne and terrestrial settings. Airborne laser scanning has been used by an aircraft during flight to generate a three-dimensional point cloud of the aircraft's surrounding landscape. Terrestrial laser scanning has been used to survey stationary or mobile objects on the surface of the Earth for use in topography, monitoring, and location determination.

However, applications of laser scanning technology known in the art typically require highly specialized equipment that may not be useful for additional applications. Further, laser scanning technology provides a limited view of an environment and typically must be used in conjunction with multiple separate systems. For example, autonomous vehicles deploy LIDAR systems in conjunction with multiple imaging cameras, radar sensors, ultrasound sensors, and others. The numerous sensors and imaging systems required by an autonomous vehicle or other system may be very costly and may consume significant physical space. In the context of medical imaging procedures, such as medical endoscopic imaging, all sensors must fit within a small physical area within a body cavity. In some instances, for example in imaging of joints or organs, the geographic area may be exceptionally small and may only accommodate a very small tip of an endoscope. As such, medical endoscopes are necessarily small and cannot accommodate multiple distinct imaging and ranging systems.

In certain implementations, it may be desirable to deploy an endoscopic imaging system for generating an image of a body cavity and further for determining measurements within the body cavity. Such images and measurements may be provided to a user for viewing the body cavity and/or used by a computer-implemented program for executing a robotic system.

In some cases, and particularly in the case of medical imaging or medical procedures, it may be beneficial to see more than a color image. Color images reflect what the human eye detects when looking at an environment. However, the human eye is limited to viewing only visible light and cannot detect other wavelengths of the electromagnetic spectrum. At other wavelengths of the electromagnetic spectrum beyond the "visible light" wavelengths, additional information may be obtained about an environment. One method of detecting additional information about an environment, beyond what the human eye is capable of detecting, is the use of fluorescent reagents. In the case of imaging for medical purposes, fluorescent reagents may provide a unique view of a body cavity that highlights certain tissues, structures, or conditions that the human eye or a computer program cannot detect in an RGB image. An additional method of detecting additional information about an environment, beyond what the human eye is capable of detecting, includes the use of hyperspectral imaging.

Fluorescence is the emission of light by a substance that has absorbed light or other electromagnetic radiation. Certain fluorescent materials may "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the particular atom, molecule, or nanostructure. In most cases, the light emitted by the substance has a longer wavelength, and therefore lower energy, than the radiation that was absorbed by the substance. However, when the absorbed electromagnetic radiation is intense, it is possible for one electron to absorb two photons. This two-photon absorption can lead to emission of radiation having a shorter wavelength, and therefore higher energy, than the absorbed radiation. Additionally, the emitted radiation may also be the same wavelength as the absorbed radiation.

Fluorescence imaging has numerous practical applications, including mineralogy, gemology, medicine, spectroscopy for chemical sensors, detecting biological processes or signals, and so forth. Fluorescence may particularly be used in biochemistry and medicine as a non-destructive means for tracking or analyzing biological molecules. The biological molecules, including certain tissues or structures, may be tracked by analyzing the fluorescent emission of the biological molecules after being excited by a certain wavelength of electromagnetic radiation. However, relatively few cellular components are naturally fluorescent. In certain implementations, it may be desirable to visualize a certain tissue, structure, chemical process, or biological process that is not intrinsically fluorescent. In such an implementation, the body may be administered a dye or reagent that may include a molecule, protein, or quantum dot having fluorescent properties. The reagent or dye may then fluoresce after being excited by a certain wavelength of electromagnetic radiation. Different reagents or dyes may include different molecules, proteins, and/or quantum dots that will fluoresce at particular wavelengths of electromagnetic radiation. Thus, it may be necessary to excite the reagent or dye with a specialized band of electromagnetic radiation to achieve fluorescence and identify the desired tissue, structure, or process in the body.

Fluorescence imaging may provide valuable information in the medical field that may be used for diagnostic purposes and/or may be visualized in real-time during a medical procedure. Specialized reagents or dyes may be administered to a body to fluoresce certain tissues, structures, chemical processes, or biological processes. The fluorescence of the reagent or dye may highlight body structures such as blood vessels, nerves, particular organs, and so forth. Additionally, the fluorescence of the reagent or dye may highlight conditions or diseases such as cancerous cells or cells experiencing a certain biological or chemical process that may be associated with a condition or disease. The fluorescence imaging may be used in real-time by a medical practitioner or computer program for differentiating between, for example, cancerous and non-cancerous cells during a surgical tumor extraction. The fluorescence imaging may further be used as a non-destructive means for tracking and visualizing over time a condition in the body that would otherwise not be visible by the human eye or distinguishable in an RGB image.

However, fluorescence imaging requires specialized emissions of electromagnetic radiation and may further require specialized imaging sensors capable of reading the wavelength of electromagnetic radiation that is emitted by the fluoresced structure or reagent. Different reagents or dyes may be sensitive to different wavelengths of electromagnetic radiation and may further emit different wavelengths of electromagnetic radiation when fluoresced. Imaging systems may then be highly specialized and tuned for a certain reagent or dye such that the system is configured to emit certain wavelengths of electromagnetic radiation and includes imaging sensors configured for reading certain wavelengths of electromagnetic radiation. Such imaging systems may be useful for very limited applications and may not be capable of fluorescing more than one reagent or structure during a single imaging session. It can be very costly to need multiple distinct imaging systems that are each configured for fluorescing a particular reagent or dye. Additionally, it may be desirable to administer multiple reagents or dyes that are each configured for fluorescing a different structure or condition and visualizing the fluorescence imaging for each of the reagents or dyes in a single overlaid image.

Hyperspectral imaging can be used to identify different materials or objects and to identify different processes. The human eye sees color of visible light in mostly three bands of wavelengths that are perceived as combinations of red, green, and blue. A typical human eye will respond to wavelengths of electromagnetic radiation from about 350 nm to about 750 nm, and this band of wavelengths may be referred to as the "visible spectrum." Hyperspectral imaging is different in that it divides the spectrum of light wavelengths into many more bands based on the reflection of tissue, object or materials. This enables hyperspectral imaging to provide information beyond what is visible to the human eye. Hyperspectral imaging may provide beneficial information in a variety of applications where it is difficult or impossible for the human eye or computers to identify specific materials, objects, or processes. Hyperspectral imaging may be particularly effective in certain cases because some objects leave unique "fingerprints" in the electromagnetic spectrum that may be referred to as spectral signatures. These spectral signatures enable identification of certain materials, objects, or processes that cannot be seen with the human eye or computers.

Hyperspectral imaging was originally developed for applications in mining and geology. Unlike a normal camera image that provides limited information to the human eye, hyperspectral imaging can identify specific minerals based on the spectral signatures of the different minerals. Hyperspectral imaging can be useful even when captured in aerial images and can provide information about, for example, oil or gas leakages from pipelines or natural wells and their effects on nearby vegetation. This information is collected based on the spectral signatures of certain materials, objects, or processes that may be identified by hyperspectral imaging.

However, hyperspectral imaging is extremely complex and can require fast computer processing capacity, sensitive detectors, and large data storage capacities. Additionally, if a hyperspectral image is overlaid on a black-and-white or color image to provide context to a practitioner, a camera (or multiples cameras) capable of generating the overlaid image may have many distinct types of pixel sensors that are sensitive to distinct ranges of electromagnetic radiation. This may include the three separate types of pixels sensors for generating an RGB color image by way of conventional methods, along with additional pixel sensors for generating the hyperspectral image data at different wavelengths of the electromagnetic spectrum. This may consume a relatively large physical space and necessitate a large pixel array to ensure that image resolution is satisfactory. In the case of endoscopic imaging, the camera or cameras may be placed in an endoscope hand-unit or robotic-unit because the multiple wavelength-sensitive pixel sensors require too much physical space, and necessitate too large a pixel array, to be placed at the distal end of the endoscope within the body cavity. This introduces the same disadvantages mentioned above and can cause the endoscope to be very delicate such that image quality is significantly degraded when the endoscope is bumped or impacted during use.

In the case of endoscopic imaging, it may be desirable to determine an array of imaging data. For example, in one implementation, it may be desirable to determine an RGB image, fluorescence imaging data, hyperspectral imaging data, and precise measurements of a light deficient environment such as a body cavity. It may be desirable to overlay specialized imaging data over a black-and-white or RGB image. For example, in one implementation, it may be desirable to determine critical body structures by way of hyperspectral and/or fluorescence imaging data, and to highlight those critical body structures as an overlay on an RGB image. Further, it may be desirable to provide precise measurements of distances and/or angles within the body cavity, including measurements concerning the critical body structures as determined by the hyperspectral and/or fluorescence imaging data. Historically, this would require the use of multiple sensor systems, including a sensing system such as LIDAR for determining measurements within the body cavity along with multiple cameras. In systems known in the art, the multiple cameras may have many distinct types of pixel sensors that are each sensitive to distinct ranges of electromagnetic radiation. This may include the three separate types of pixels sensors for generating an RGB color image by way of conventional methods, along with additional pixel sensors for generating the fluorescence and/or hyperspectral image data at different wavelengths of the electromagnetic spectrum. This may consume a prohibitively large physical space and necessitate a large pixel array to ensure that image resolution is satisfactory. In the case of endoscopic imaging, the camera or cameras may be placed in an endoscope hand-unit or robotic-unit because the multiple wavelength-sensitive pixel sensors require too much physical space, and necessitate too large a pixel array, to be placed at the distal end of the endoscope within the body cavity. This introduces the same disadvantages mentioned above and can cause the endoscope to be very delicate such that image quality is significantly degraded when the endoscope is bumped or impacted during use.

As such, it is desirable to provides systems, methods, and devices for endoscopic imaging in a light deficient environment. Such systems, methods, and devices may provide multiple data sets for identifying critical structures in a body and providing precise and valuable information about the body cavity.

This disclosure relates generally to electromagnetic sensing and sensors that may be applicable to endoscope imaging. The disclosure also relates to low energy electromagnetic input conditions as well as low energy electromagnetic throughput conditions. The disclosure relates more particularly, but not necessarily entirely, to a system for producing an image in light deficient environments and associated structures, methods and features, which may include controlling a light source through duration, intensity or both, pulsing a component controlled light source during the blanking period of an image sensor ref, maximizing the blanking period to allow optimum light, and maintaining color balance.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified.

Advantages of the disclosure will become better understood with regard to the following description and accompanying drawings where:

FIGS. 2A to 2D are illustrations of the operational cycles of a sensor used to construct one image frame, according to embodiments of the disclosure;

FIG. 24 illustrates the impact on signal to noise ratio of the color correction for a typical Bayer-based sensor compared with no color correction;

DETAILED DESCRIPTION

Figure 1:
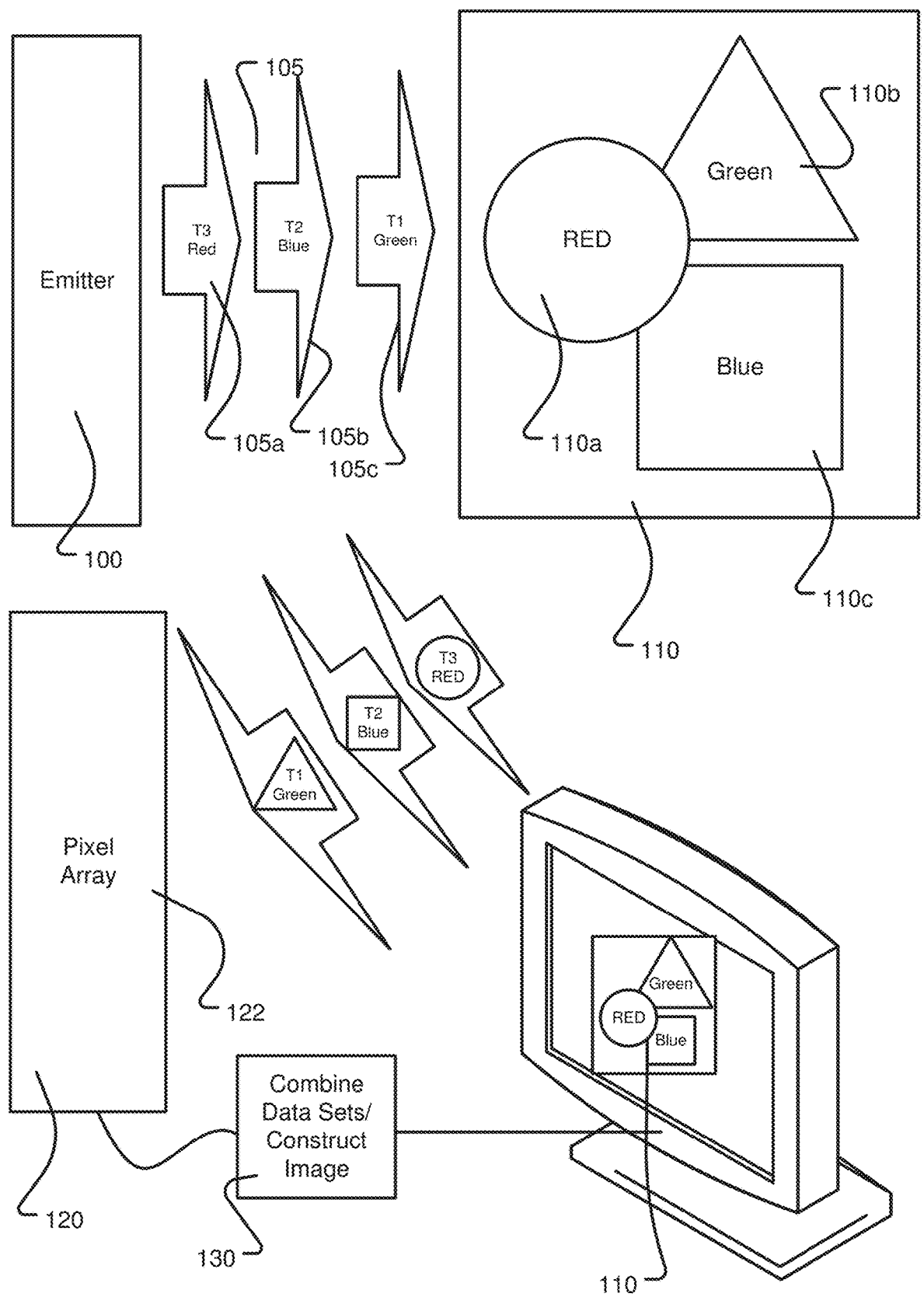
FIG. 1 is a schematic view of an embodiment of a system of a paired sensor and an electromagnetic emitter in operation for use in producing an image in a light deficient environment, according to one embodiment.

The disclosure extends to methods, systems, and computer-based products for digital imaging that may be primarily suited to medical applications such as medical endoscopic imaging. Such methods, systems, and computer-based products as disclosed herein may provide imaging or diagnostic capabilities for use in medical robotics applications, such as the use of robotics for performing imaging procedures, surgical procedures, and the like. In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

Endoscopes have a great variety of uses and may provide significant benefits in the medical field. Endoscopy is used in medicine to look inside a body and in some cases may provide imaging that would otherwise be impossible to see or would require invasive surgical procedures. Endoscopes may be used for medical diagnostics, investigation, or research, and may also be used to perform medical procedures in a minimally invasive manner Medical endoscopes may provide significant benefits to patients and medical practitioners by negating the need for painful and invasive corrective or exploratory surgeries.

As disclosed herein, an endoscopic system for use in a light deficient environment, such as a cavity of a body, may include an imaging device and a light engine. The light engine may include an illumination source for generating pulses of electromagnetic radiation and may further include a lumen for transmitting pulses of electromagnetic radiation to a distal tip of an endoscope. The lumen may transmit the pulses of electromagnetic radiation at particular wavelengths or bands of wavelengths of the electromagnetic spectrum. The lumen may transmit such pulses in a timed sequence and imaging data may be captured by a sensor during each of the pulses. The imaging data associated with the different wavelengths of the pulses may be used to generate a red green blue (RGB) image and/or fluorescence images. In an embodiment, fluorescence imaging may be overlaid on a black-and-white or RGB image.

As disclosed herein, the systems, methods, and devices for an endoscopic image system may provide specialized image data of a light deficient environment. The specialized image data may be used to generate fluorescence imaging and/or identify certain materials, tissues, components, or processes within a light deficient environment. In certain embodiments, fluorescence imaging may be provided to a practitioner or computer-implemented program to enable the identification of certain structures or tissues within a body. Such fluorescence imaging data may be overlaid on black-and-white or RGB images to provide additional information and context.

Further, such systems, methods, and devices for an endoscopic image system may be used in coordination with certain reagents or dyes. In a medical imaging implementation, certain reagents or dyes may be administered to a patient, and those reagents or dyes may fluoresce or react to certain wavelengths of electromagnetic radiation. The endoscopic image system as disclosed herein may transmit electromagnetic radiation at specified wavelengths to fluoresce the reagents or dyes. The fluorescence of the reagents or dyes may be captured by an image sensor to generate imaging to aid in the identification of tissues or structures and/or to aid in diagnosis or research. In an implementation, a patient may be administered a plurality of reagents or dyes that are each configured to fluoresce at different wavelengths and/or provide an indication of different structures, tissues, chemical reactions, biological processes, and so forth. In such an implementation, the endoscopic system as disclosed herein may emit each of the applicable wavelengths to fluoresce each of the applicable reagents or dyes. This may negate the historical need to perform individual imaging procedures for each of a plurality of reagents or dyes.

Medical endoscopes may provide a continuous digital image stream of an interior space of a body where a distal end of the endoscope is inserted. In various implementations, it may be beneficial or even necessary that the digital image stream provides full color imaging such that a medical practitioner may better differentiate between tissues and structures in the body. In further implementations, it may be beneficial to provide hyperspectral imaging data to differentiate between structures, tissues, processes, and conditions with enhanced precision. Additionally, hyperspectral imaging may enable a medical practitioner or computer program to receive information about a condition in a human body that is not visible to the human eye or discernable in an RGB color image.

Systems, methods, and devices are disclosed herein for generating color image data and/or fluorescence image data by an endoscope. A system of the disclosure includes an imaging device having a tube, one or more image sensors, and a lens assembly. The lens assembly may include at least one optical element that corresponds to at least one of the one or more image sensors. The system further includes a display to visual a scene and an image signal processing controller. The system may further include a light engine. The light engine includes an illumination source configured to generate one or more pulses of electromagnetic radiation and a lumen that transmits one or more pulses of electromagnetic radiation to a distal tip of an endoscope. In an embodiment, at least a portion of the one or more pulses of electromagnetic radiation includes an excitation wavelength of electromagnetic radiation between 770 nm and 790 nm that cause one or more reagents to fluoresce at a wavelength that is different from the excitation wavelength of the portion of the one or more pulses of electromagnetic radiation.

In an embodiment of the disclosure, an endoscope system illuminates a source and pulses electromagnetic radiation at a certain wavelength for exciting an electron in a reagent or dye. In an embodiment, the reagent or dye is configured to fluoresce in response to the certain wavelength of electromagnetic radiation that is emitted by the endoscope system. An image sensor in the endoscope system may read a fluorescence relaxation emission of the reagent or dye that may be of lower energy than the pulsed electromagnetic radiation for exciting the reagent or dye. The reagent or dye may be specialized for labeling a certain tissue, structure, biological process, and/or chemical process.

Imaging reagents, including fluorescent reagents, may enhance imaging capabilities in pharmaceutical, medical, biotechnology, diagnostic, and medical procedure industries. Many imaging techniques such as X-ray, computer tomography (CT), ultrasound, magnetic resonance imaging (MRI), and nuclear medicine, mainly analyze anatomy and morphology and are unable to detect changes at the molecular level. Fluorescent reagents, dyes, and probes, including quantum dot nanoparticles and fluorescent proteins, may assist medical imaging technologies by providing additional information about certain tissues, structures, chemical processes, and/or biological processes that are present within the imaging region. Imaging using fluorescent reagents may enable cell tracking and/or the tracking of certain molecular biomarkers. Fluorescent reagents may be applied for imaging cancer, infection, inflammation, stem cell biology, and others. Numerous fluorescent reagents and dyes are being developed and applied for visualizing and tracking biological processes in a non-destructive manner Such fluorescent reagents may be excited by a certain wavelength or band of wavelengths of electromagnetic radiation. Similarly, those fluorescent reagents may emit relaxation energy at a certain wavelength or band of wavelengths when fluorescing, and the emitted relaxation energy may be read by a sensor to determine the location and/or boundaries of the reagent or dye.

In an embodiment of the disclosure, an endoscope system pulses electromagnetic radiation for exciting an electron in a fluorescent reagent or dye. The wavelength or band of wavelengths of the electromagnetic radiation may be particularly selected for fluorescing a certain reagent or dye. In an embodiment, the endoscope system may pulse multiple different wavelengths of electromagnetic radiation for fluorescing multiple different reagents or dyes during a single imaging session. A sensor of the endoscope system may determine a location and/or boundary of a reagent or dye based on the relaxation emissions of the reagent or dye. The endoscope system may further pulse electromagnetic radiation in red, green, and blue bands of visible light. The endoscope system may determine data for an RGB image and a fluorescence image according to a pulsing schedule for the pulses of electromagnetic radiation.

In an embodiment of the disclosure, an endoscope system illuminates a source and pulses electromagnetic radiation for spectral or hyperspectral imaging. Spectral imaging uses multiple bands across the electromagnetic spectrum. This is different from conventional cameras that only capture light across the three wavelengths based in the visible spectrum that are discernable by the human eye, including the red, green, and blue wavelengths to generate an RGB image. Spectral imaging may use any wavelength bands in the electromagnetic spectrum, including infrared wavelengths, the visible spectrum, the ultraviolet spectrum, x-ray wavelengths, or any suitable combination of various wavelength bands. Spectral imaging may overlay imaging generated based on non-visible bands (e.g., infrared) on top of imaging based on visible bands (e.g. a standard RGB image) to provide additional information that is easily discernable by a person or computer algorithm.

Hyperspectral imaging is a subcategory of spectral imaging. Hyperspectral imaging includes spectroscopy and digital photography. In an embodiment of hyperspectral imaging, a complete spectrum or some spectral information is collected at every pixel in an image plane. A hyperspectral camera may use special hardware to capture any suitable number of wavelength bands for each pixel which may be interpreted as a complete spectrum. The goal of hyperspectral imaging may vary for different applications. In one application, the goal of hyperspectral imaging is to obtain the entire electromagnetic spectrum of each pixel in an image scene. This may enable certain objects to be found that might otherwise not be identifiable under the visible light wavelength bands. This may enable certain materials or tissues to be identified with precision when those materials or tissues might not be identifiable under the visible light wavelength bands. Further, this may enable certain processes to be detected by capturing an image across all wavelengths of the electromagnetic spectrum.

Hyperspectral imaging may provide particular advantages over conventional imaging in medical applications. The information obtained by hyperspectral imaging can enable medical practitioners and/or computer-implemented programs to precisely identify certain tissues or conditions that may lead to diagnoses that may not be possible or may be less accurate if using conventional imaging such as RGB imaging. Additionally, hyperspectral imaging may be used during medical procedures to provide image-guided surgery that may enable a medical practitioner to, for example, view tissues located behind certain tissues or fluids, identify atypical cancerous cells in contrast with typical healthy cells, identify certain tissues or conditions, identify critical structures and so forth. Hyperspectral imaging may provide specialized diagnostic information about tissue physiology, morphology, and composition that cannot be generated with conventional imaging.

Endoscopic hyperspectral imaging may present advantages over conventional imaging in various applications and implementations of the disclosure. In medical implementations, endoscopic hyperspectral imaging may permit a practitioner or computer-implemented program to discern, for example, nervous tissue, muscle tissue, various vessels, the direction of blood flow, and so forth. Hyperspectral imaging may enable atypical cancerous tissue to be precisely differentiated from typical healthy tissue and may therefore enable a practitioner or computer-implemented program to discern the boundary of a cancerous tumor during an operation or investigative imaging. Additionally, hyperspectral imaging in a light deficient environment as disclosed herein may be combined with the use of a reagent or dye to enable further differentiation between certain tissues or substances. In such an embodiment, a reagent or dye may be fluoresced by a specific wavelength band in the electromagnetic spectrum and therefore provide information specific to the purpose of that reagent or dye. The systems, methods, and devices as disclosed herein may enable any number of wavelength bands to be pulsed such that one or more reagents or dyes may be fluoresced at different times. In certain implementations, this may enable the identification or investigation of a number of medical conditions during a single imaging procedure.

A medical endoscope may pulse electromagnetic radiation at wavelength bands outside the visible light spectrum to enable the generation of hyperspectral images. Endoscopic hyperspectral imaging is a contactless and non-invasive means for medical imaging that does not require a patient to undergo harmful radiation exposure common in other imaging methods.

Conventional endoscopes, used in, for example, robotics endoscopic procedures such as arthroscopy and laparoscopy, are designed such that the image sensors are typically placed within a hand-piece unit that is held by an endoscope operator and is not inserted into a cavity. In such a configuration, an endoscope unit transmits incident light along the length of an endoscope tube toward the sensor via a complex set of precisely coupled optical components, with minimal loss and distortion. The cost of the endoscope unit is dominated by the optics because the optics components are expensive, and the manufacturing process of the optics components is labor intensive. Further, this type of endoscope is mechanically delicate and relatively minor impacts can easily damage the components or upset the relative alignments of those components. Even minor misalignments to the endoscope components (such as the precisely coupled optical components) can cause significant degradation to image quality or render the endoscope unusable. When the components are misaligned, the incident light traveling along the length of the endoscope may fall off such that there is little or no light at the distal end of the endoscope and the endoscope becomes unusable. Because conventional endoscopes require such precise and complex optical components, and because those components can become easily misaligned, such convention endoscopes require frequent and expensive repair cycles to maintain image quality.

One solution to this issue is to place the image sensor within the endoscope itself at the distal end. Such a solution may eliminate the need for a complex and precise collection of coupled optical components that can be easily misaligned and/or damaged. This solution potentially approaches the optical simplicity, robustness, and economy that is universally realized within, for example, mobile phone cameras. However, it should be appreciated that a great deal of the benefits provided by an endoscope arise from the compact size of the distal end of the endoscope. If the distal end of the endoscope is enlarged to accommodate the multiple distinct wavelength-sensitive pixel sensors conventionally used for color imaging or hyperspectral imaging, the pixel array may be too large, and the endoscope may no longer fit in tight spaces or may be obstructive or invasive when used in a medical implementation. Because the distal end of the endoscope must remain very small, it is challenging to place one or more image sensors at the distal end. An acceptable solution to this approach is by no means trivial and introduces its own set of engineering challenges, not the least of which is the fact that the sensors for color and/or hyperspectral imaging must fit within an area that is highly confined. This is particularly challenging where a pixel array in conventional cameras include separate pixel sensors for each of red, green, and blue visible light bands, along with additional pixel sensors for other wavelength bands used for hyperspectral imaging. The area of the distal tip of the endoscope may be particularly confined side-to-side in the X and Y dimensions, while there is more space along the length of the endoscope tube in the Z dimension.

Because many of the benefits of an endoscope arise from the small size of the distal end of the endoscope, aggressive constraints must be placed on the image sensor area when the image sensors are located at the distal end. These aggressive constraints placed on the sensor area naturally results in fewer and/or smaller pixels within a pixel array. Lowering the pixel count may directly affect the spatial resolution, while reducing the pixel area may reduce the available signal capacity and thereby the sensitivity of the pixel, as well as optimizing the number of pixels such that image quality is maximized, the minimum pixel resolution and native number of pixels using the maximum pixel quality and pitch, such that resolution is not an issue as well as lowering the signal to noise ratio (SNR) of each pixel. Lowering the signal capacity reduces the dynamic range, i.e., the ability of the imaging device or camera to simultaneously capture all the useful information from scenes with large ranges of luminosity. There are various methods to extend the dynamic range of imaging systems beyond that of the pixel itself. All of them may have some kind of penalty, however, (e.g., in resolution or frame rate) and they can introduce undesirable artifacts, which become problematic in extreme cases. Reducing the sensitivity has the consequence that greater light power is required to bring the darker regions of the scene to acceptable signal levels. Lowering the F-number (enlarging the aperture) can compensate for a loss in sensitivity, but at the cost of spatial distortion and reduced depth of focus.

In the sensor industry, complementary metal-oxide-semiconductor ("CMOS") image sensors have largely displaced conventional charge-coupled device ("CCD") image sensors in modern camera applications. CMOS image sensors have greater ease of integration and operation, superior or comparable image quality, greater versatility and lower cost, compared with CCD image sensors. Typically, CMOS image sensors may include the circuitry necessary to convert image information into digital data and have various levels of digital processing incorporated thereafter. This can range from basic algorithms for the purpose of correcting non-idealities, which may, for example, arise from variations in amplifier behavior, to full image signal processing (ISP) chains, providing video data in the standard red-green-blue ("RGB") color space for example (cameras-on-chip).

The control unit for an endoscope or image sensor may be located remotely from the image sensor and may be a significant physical distance away from the image sensor. When the control unit is remote from the sensor, it may be desirable to transmit the data in the digital domain because it is largely immune to interference noise and signal degradation when compared to transmitting an analog data stream. It will be appreciated that various electrical digital signaling standards may be used, such as LVDS (low voltage differential signaling), sub-LVDS, SLVS (scalable low voltage signaling) or other electrical digital signaling standards.

There may be a strong desire to minimize the number of electrical conductors to reduce the number of pads consuming space on the sensor, and to reduce the complexity and cost of sensor manufacture. Although the addition of analog to digital conversion to the sensor may be advantageous, the additional area occupied by the conversion circuits is offset because of the significant reduction in the analog buffering power needed due to the early conversion to a digital signal.

In terms of area consumption, given the typical feature size available in CMOS image sensor (CIS) technologies, it may be preferable in some implementations to have all the internal logic signals generated on the same chip as the pixel array via a set of control registers and a simple command interface.

Some implementations of the disclosure may include aspects of a combined sensor and system design that allows for high definition imaging with reduced pixel counts in a highly controlled illumination environment. This may be accomplished by virtue of frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a hyperspectral image. The pixels may be color agnostic such that each pixel may generate data for each pulse of electromagnetic radiation, including pulses for red, green, and blue visible light wavelengths along with other wavelengths that may be used for hyperspectral imaging.

As used herein, monochromatic sensor refers to an unfiltered imaging sensor. Since the pixels are color agnostic, the effective spatial resolution is appreciably higher than for their color (typically Bayer-pattern filtered) counterparts in conventional single-sensor cameras. They may also have higher quantum efficiency since far fewer incident photons are wasted between the individual pixels. Moreover, Bayer based spatial color modulation requires that the modulation transfer function (MTF) of the accompanying optics be lowered compared with the monochrome modulation, to blur out the color artifacts associated with the Bayer pattern. This has a detrimental impact on the actual spatial resolution that can be realized with color sensors.

The disclosure is also concerned with a system solution for endoscopy applications in which the image sensor is resident at the distal end of the endoscope. In striving for a minimal area sensor-based system, there are other design aspects that can be developed, beyond reduction in pixel count. The area of the digital portion of the chip may be minimized In addition, the number of connections to the chip (pads) may also be minimized. The disclosure describes novel methods that accomplish these goals for the realization of such a system. This involves the design of a full-custom CMOS image sensor with several novel features.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

Referring now to FIGS. 1-5, the systems and methods for producing an image in a light deficient environment will now be described. FIG. 1 illustrates a schematic view of a paired sensor and an electromagnetic emitter in operation for use in producing an image in a light deficient environment. Such a configuration allows for increased functionality in a light controlled or ambient light deficient environment.

It should be noted that as used herein the term "light" is both a particle and a wavelength and is intended to denote electromagnetic radiation that is detectable by a pixel array and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

A pixel array of an image sensor may be paired with an emitter electronically, such that they are synced during operation for both receiving the emissions and for the adjustments made within the system. As can be seen in FIG. 1, an emitter 100 may be tuned to emit electromagnetic radiation in the form of a laser, which may be pulsed to illuminate an object 110. The emitter 100 may pulse at an interval that corresponds to the operation and functionality of a pixel array 122. The emitter 100 may pulse light in a plurality of electromagnetic partitions 105, such that the pixel array receives electromagnetic energy and produces a data set that corresponds (in time) with each specific electromagnetic partition 105. For example, FIG. 1 illustrates a system having a monochromatic sensor 120 having a pixel array (black and white) 122 and supporting circuitry, which pixel array 122 is sensitive to electromagnetic radiation of any wavelength. The light emitter 100 illustrated in the figure may be a laser emitter that is capable of emitting a red electromagnetic partition 105a, a blue electromagnetic partition 105b, and a green electromagnetic partition 105c in any desired sequence. In an embodiment where a hyperspectral image may be generated, the light emitter 100 may pulse electromagnetic radiation at any wavelength in the electromagnetic spectrum such that a hyperspectral image may be generated. It will be appreciated that other light emitters 100 may be used in FIG. 1 without departing from the scope of the disclosure, such as digital or analog based emitters.

During operation, the data created by the monochromatic sensor 120 for any individual pulse may be assigned a specific color or wavelength partition, wherein the assignment is based on the timing of the pulsed color or wavelength partition from the emitter 100. Even though the pixels 122 are not color-dedicated, they can be assigned a color for any given data set based on a priori information about the emitter.

In an exemplary embodiment of the disclosure, the emitter 100 pulses electromagnetic radiation at specialized wavelengths. Such pulses may enable the generation of a specialized fluorescence image that is particularly suited for certain medical or diagnostic applications. In the exemplary embodiment, at least a portion of the electromagnetic radiation emitted by the emitter 100 includes an excitation wavelength of electromagnetic radiation between 770 nm and 790 nm and between 795 nm and 815 nm that cause one or more reagents to fluoresce at a wavelength that is different from the excitation wavelength of the portion of the electromagnetic radiation.

In one embodiment, three data sets representing RED, GREEN and BLUE electromagnetic pulses may be combined to form a single image frame. One or more additional data sets representing other wavelength partitions may be overlaid on the single image frame that is based on the RED, GREEN, and BLUE pulses. The one or more additional data sets may represent, for example, fluorescence imaging responsive to the excitation wavelength between 770 nm and 790 nm and between 795 nm and 815 nm. The one or more additional data sets may represent fluorescence imaging and/or hyperspectral that may be overlaid on the single image frame that is based on the RED, GREEN, and BLUE pulses.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infra-red; any combination of the foregoing, or any other color combination, including all visible and non-visible wavelengths, without departing from the scope of the disclosure. In the figure, the object 110 to be imaged contains a red portion 110a, green portion 110b and a blue portion 110c. As illustrated in the figure, the reflected light from the electromagnetic pulses only contains the data for the portion of the object having the specific color that corresponds to the pulsed color partition. Those separate color (or color interval) data sets can then be used to reconstruct the image by combining the data sets at 130.

In one embodiment, a plurality of data sets representing RED, GREEN, and BLUE electromagnetic pulses along with additional wavelength partitions along the electromagnetic spectrum may be combined to form a single image frame having an RGB image with hyperspectral image data overlaid on the RGB image. Depending on the application or instance, different combinations of wavelength data sets may be desirable. For example, in some implementations, a data set representing specific wavelength partitions may be used to generate a specialized hyperspectral image for diagnosing a particular medical condition, investigating certain body tissues, and so forth.

Figure 2:
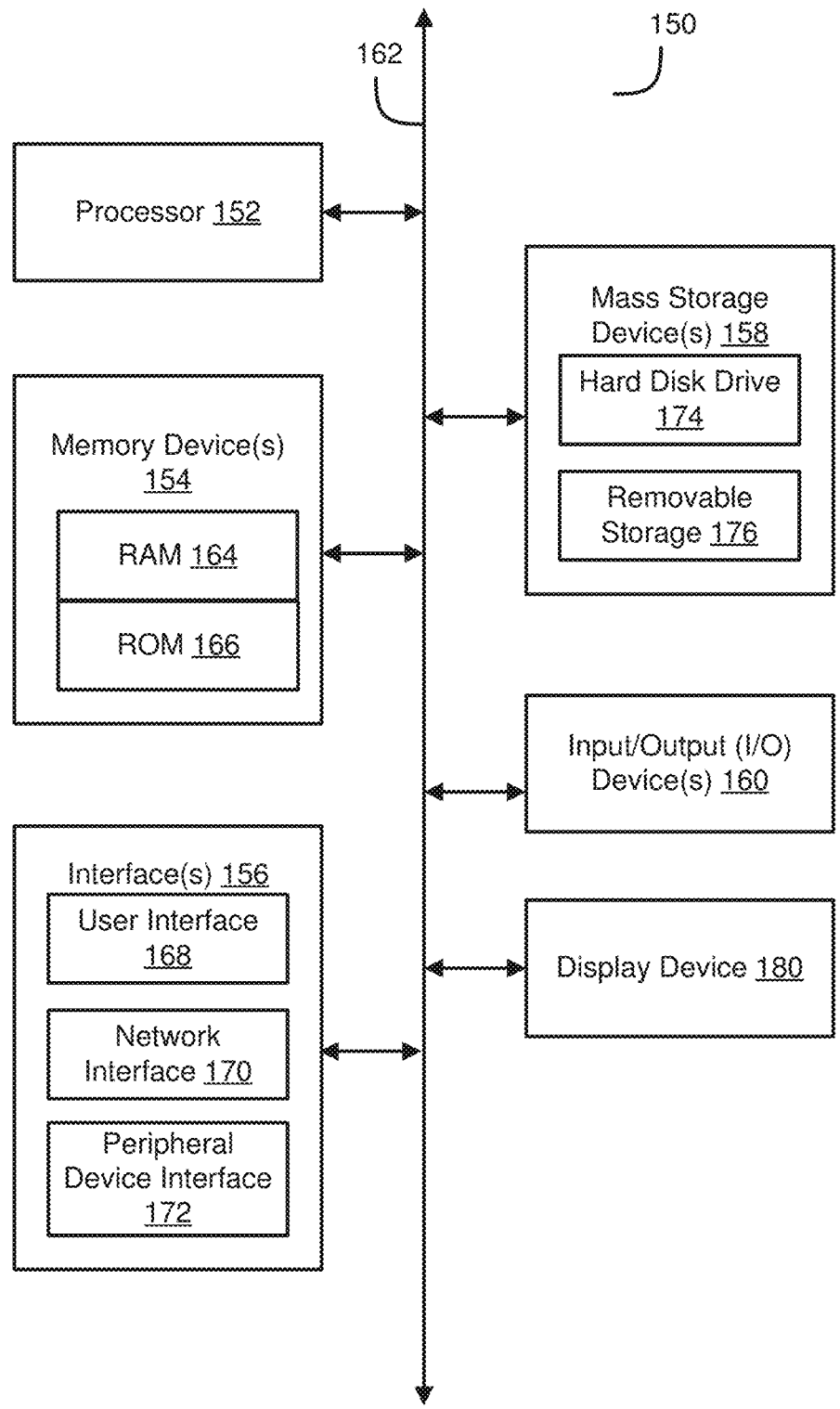
FIG. 2 is a schematic view of complementary system hardware.

As illustrated in FIG. 2, implementations of the present disclosure may comprise or utilize a special purpose or general-purpose computer, including computer hardware, such as, for example, one or more processors and system memory, as discussed in greater detail below. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2 is a block diagram illustrating an example computing device 150. Computing device 150 may be used to perform various procedures, such as those discussed herein. Computing device 150 can function as a server, a client, or any other computing entity. Computing device 150 can perform various monitoring functions as discussed herein, and can execute one or more application programs, such as the application programs described herein. Computing device 150 can be any of a wide variety of computing devices, such as a desktop computer, a notebook computer, a server computer, a handheld computer, camera control unit, tablet computer and the like.

Computing device 150 includes one or more processor(s) 152, one or more memory device(s) 154, one or more interface(s) 156, one or more mass storage device(s) 158, one or more Input/Output (I/O) device(s) 160, and a display device 180 all of which are coupled to a bus 162. Processor (s) 152 include one or more processors or controllers that execute instructions stored in memory device(s) 154 and/or mass storage device(s) 158. Processor(s) 152 may also include various types of computer-readable media, such as cache memory.

Memory device(s) 154 include various computer-readable media, such as volatile memory (e.g., random access memory (RAM) 164) and/or nonvolatile memory (e.g., read-only memory (ROM) 166). Memory device(s) 154 may also include rewritable ROM, such as Flash memory.

Mass storage device(s) 158 include various computer readable media, such as magnetic tapes, magnetic disks, optical disks, solid-state memory (e.g., Flash memory), and so forth. As shown in FIG. 2, a particular mass storage device is a hard disk drive 174. Various drives may also be included in mass storage device(s) 158 to enable reading from and/or writing to the various computer readable media. Mass storage device(s) 158 include removable media 176 and/or non-removable media.

I/O device(s) 160 include various devices that allow data and/or other information to be input to or retrieved from computing device 150. Example I/O device(s) 160 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 180 includes any type of device capable of displaying information to one or more users of computing device 150. Examples of display device 180 include a monitor, display terminal, video projection device, and the like.

Interface(s) 106 include various interfaces that allow computing device 150 to interact with other systems, devices, or computing environments. Example interface(s) 156 may include any number of different network interfaces 170, such as interfaces to local area networks (LANs), wide area networks (WANs), wireless networks, and the Internet. Other interface(s) include user interface 168 and peripheral device interface 172. The interface(s) 156 may also include one or more user interface elements 168. The interface(s) 156 may also include one or more peripheral interfaces such as interfaces for printers, pointing devices (mice, track pad, etc.), keyboards, and the like.

Bus 162 allows processor(s) 152, memory device(s) 154, interface(s) 156, mass storage device(s) 158, and I/O device (s) 160 to communicate with one another, as well as other devices or components coupled to bus 162. Bus 162 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 150, and are executed by processor(s) 152. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 2A:
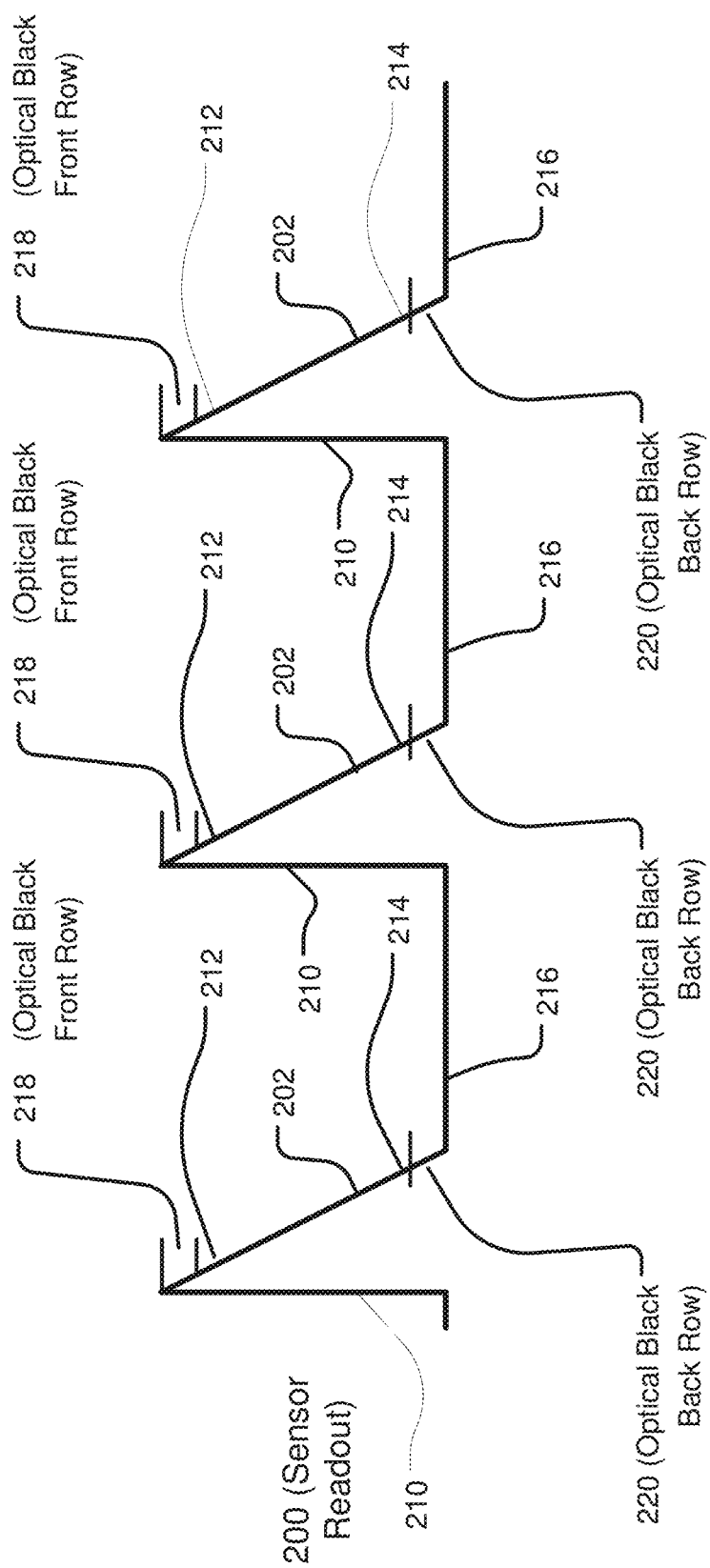
Figure 2D:
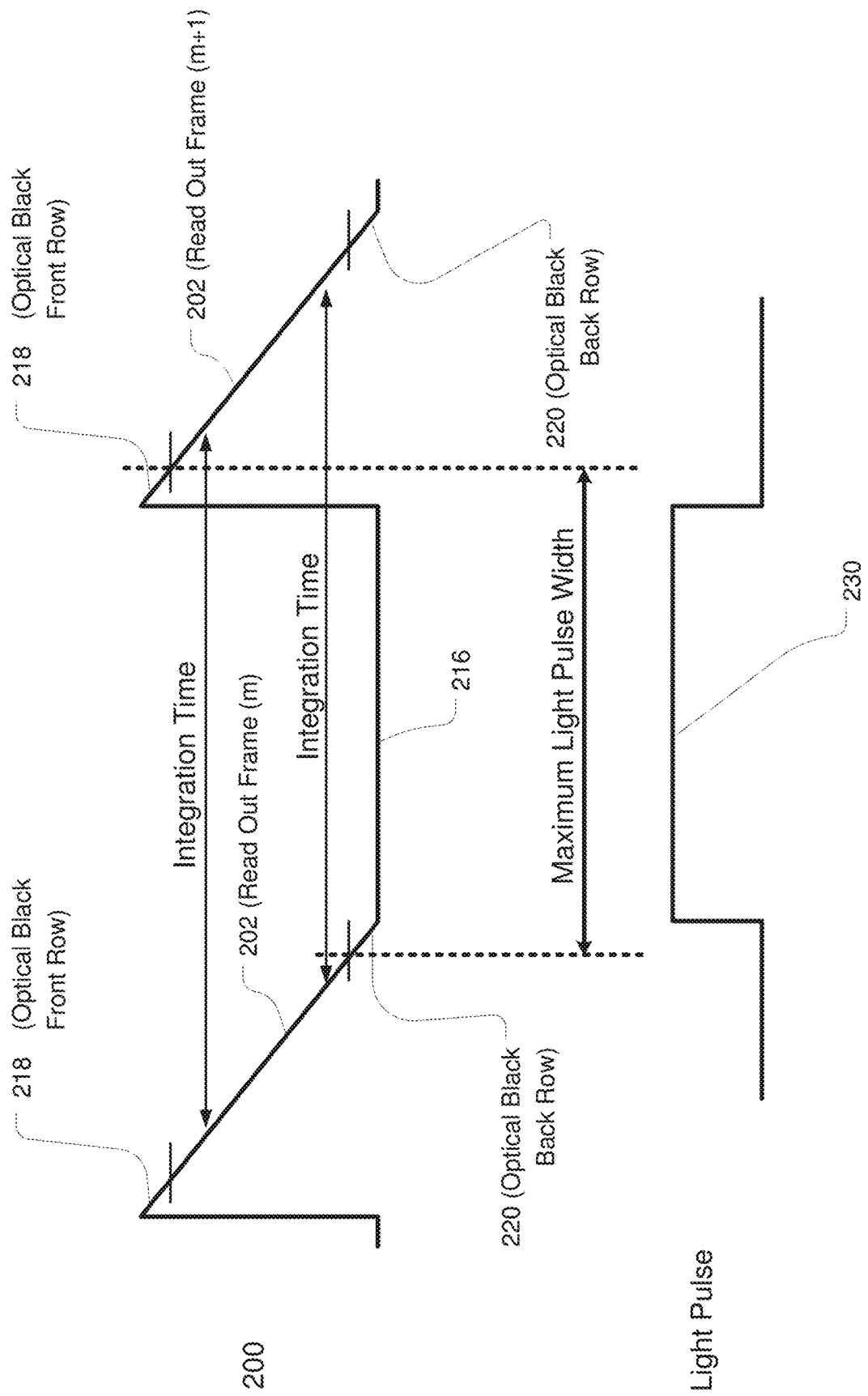

FIG. 2A illustrates the operational cycles of a sensor used in rolling readout mode or during the sensor readout 200. The frame readout may start at and may be represented by vertical line 210. The read-out period is represented by the diagonal or slanted line 202. The sensor may be read out on a row by row basis, the top of the downwards slanted edge being the sensor top row 212 and the bottom of the downwards slanted edge being the sensor bottom row 214. The time between the last row readout and the next readout cycle may be called the blanking time 216. It should be noted that some of the sensor pixel rows might be covered with a light shield (e.g., a metal coating or any other substantially black layer of another material type). These covered pixel rows may be referred to as optical black rows 218 and 220. Optical black rows 218 and 220 may be used as input for correction algorithms. As shown in FIG. 2A, these optical black rows 218 and 220 may be located on the top of the pixel array or at the bottom of the pixel array or at the top and the bottom of the pixel array. FIG. 2B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 222) may be used to start the integration time by resetting the pixel. The light will then integrate until the next readout phase. The position of the electronic shutter 222 can be moved between two readout cycles 202 to control the pixel saturation for a given amount of light. It should be noted that this technique allows for a constant integration time between two different lines but introduces a delay when moving from top to bottom rows. FIG. 2C illustrates the case where the electronic shutter 222 has been removed. In this configuration, the integration of the incoming light may start during readout 202 and may end at the next readout cycle 202, which also defines the start of the next integration. FIG. 2D shows a configuration without an electronic shutter 222, but with a controlled and pulsed light 230 during the blanking time 216. This ensures that all rows see the same light issued from the same light pulse 230. In other words, each row will start its integration in a dark environment, which may be at the optical black back row 220 of read out frame (m) for a maximum light pulse width, and will then receive a light strobe and will end its integration in a dark environment, which may be at the optical black front row 218 of the next succeeding read out frame (m+1) for a maximum light pulse width. In the FIG. 2D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking time 216. Because the optical black rows 218, 220 are insensitive to light, the optical black back rows 220 time of frame (m) and the optical black front rows 218 time of frame (m+1) can be added to the blanking time 216 to determine the maximum range of the firing time of the light pulse 230. As illustrated in the FIG. 2A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 3:
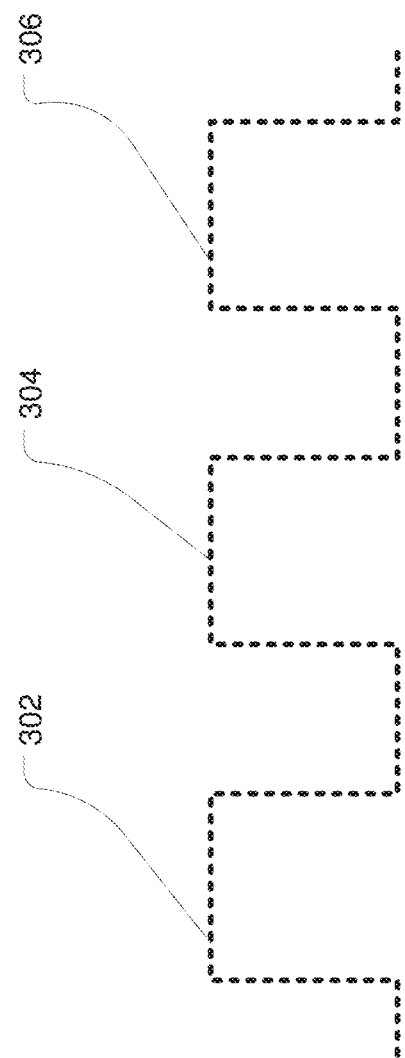
FIG. 3 is a graphical representation of the operation of an embodiment of an electromagnetic emitter, according to one embodiment.

FIG. 3 graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 3 illustrates Pulse 1 at 302, Pulse 2 at 304, and Pulse 3 at 306. In an embodiment, the emitter may pulse during the read-out portion 202 of the sensor operation cycle. In an embodiment, the emitter may pulse during the blanking portion 216 of the sensor operation cycle. In an embodiment, the emitter may pulse for a duration that is during portions of two or more sensor operational cycles. In an embodiment, the emitter may begin a pulse during the blanking portion 216, or during the optical black portion 220 of the readout portion 202, and end the pulse during the readout portion 202, or during the optical black portion 218 of the readout portion 202 of the next succeeding cycle. It will be understood that any combination of the above is intended to fall within the scope of this disclosure as long as the pulse of the emitter and the cycle of the sensor correspond.

Figure 4:
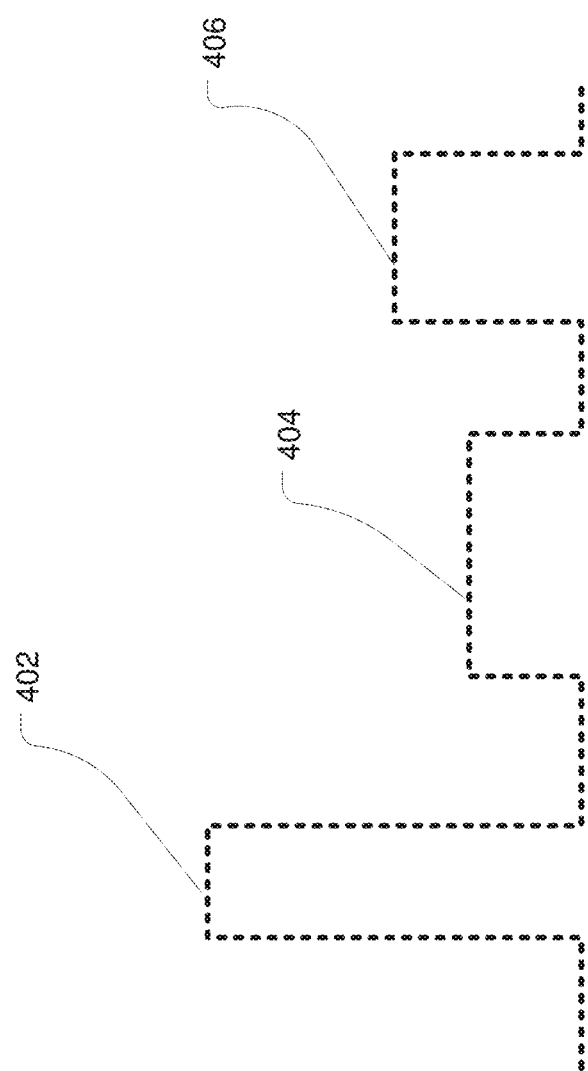
FIG. 4 is a graphical representation of varying the duration and magnitude of the emitted electromagnetic pulse to provide exposure control, according to one embodiment.

FIG. 4 graphically represents varying the duration and magnitude of the emitted electromagnetic pulse (e.g., Pulse 1 at 402, Pulse 2 at 404, and Pulse 3 at 406) to control exposure. An emitter having a fixed output magnitude may be pulsed during any of the cycles noted above in relation to FIGS. 2D and 3 for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time that the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4 illustrates varying the magnitude and duration of the pulses. In the illustration, Pulse 1 at 402 has a higher magnitude or intensity than either Pulse 2 at 404 or Pulse 3 at 406. Additionally, Pulse 1 at 402 has a shorter duration than Pulse 2 at 404 or Pulse 3 at 406, such that the electromagnetic energy provided by the pulse is illustrated by the area under the pulse shown in the illustration. In the illustration, Pulse 2 at 404 has a relatively low magnitude or intensity and a longer duration when compared to either Pulse 1 at 402 or Pulse 3 at 406. Finally, in the illustration, Pulse 3 at 406 has an intermediate magnitude or intensity and duration, when compared to Pulse 1 at 402 and Pulse 2 at 404.

Figure 5:
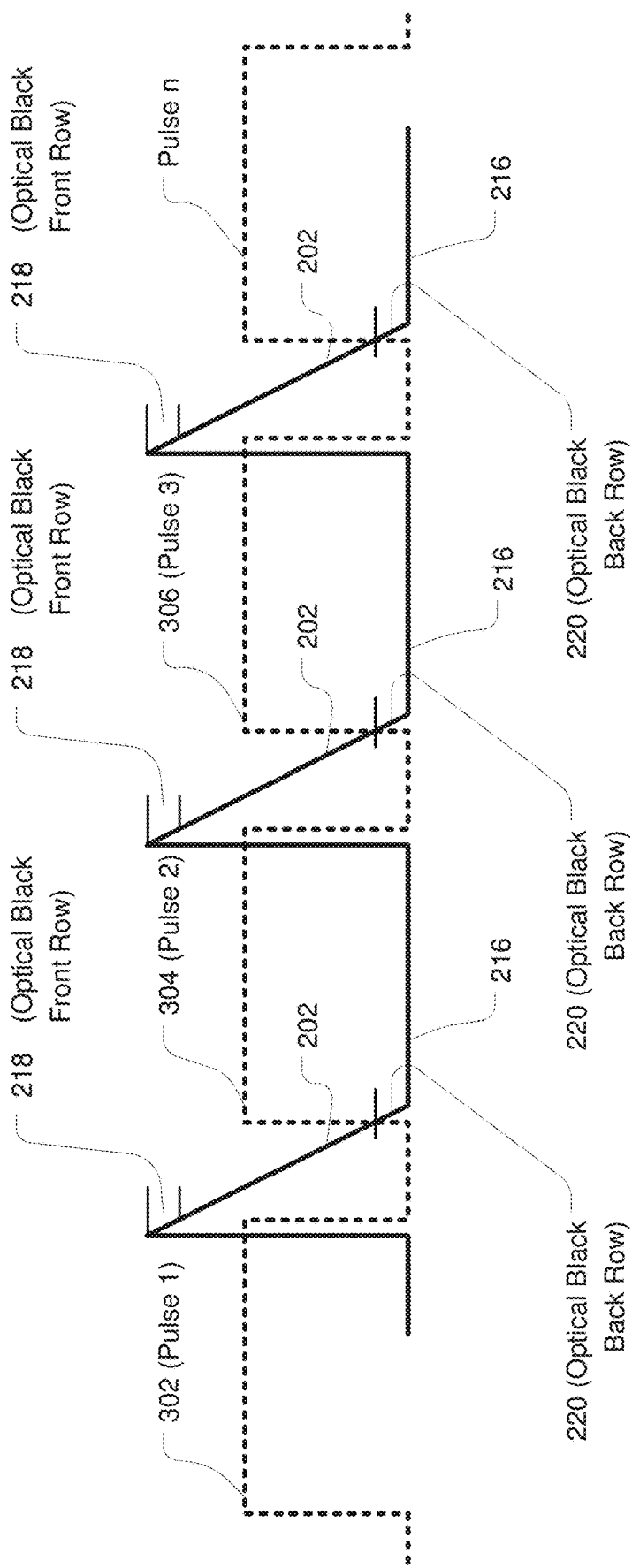
FIG. 5 is a graphical representation of an embodiment of the disclosure combining the operational cycles of a sensor, the electromagnetic emitter and the emitted electromagnetic pulses of FIGS. 2A-4, which demonstrate the imaging system during operation, according to one embodiment.

FIG. 5 is a graphical representation of an embodiment of the disclosure combining the operational cycles, the electromagnetic emitter and the emitted electromagnetic pulses of FIGS. 2-4 to demonstrate the imaging system during operation in accordance with the principles and teachings of the disclosure. As can be seen in the figure, the electromagnetic emitter pulses the emissions primarily during the blanking period 216 of the sensor, such that the pixels will be charged and ready to read during the read-out portion 202 of the sensor cycle. The dashed line portions in the pulse (from FIG. 3) illustrate the potential or ability to emit electromagnetic energy during the optical black portions 220 and 218 of the read cycle (sensor cycle) 200 if additional time is needed or desired to pulse electromagnetic energy.

Referring now to FIGS. 6-9A, FIG. 6 illustrates a schematic of two distinct processes over a period of time from t(0) to t(1) for recording a frame of video for full spectrum light and partitioned spectrum light. It should be noted that color sensors have a color filter array (CFA) for filtering out certain wavelengths of light per pixel commonly used for full spectrum light reception. An example of a CFA is a Bayer pattern. Because the color sensor may comprise pixels within the array that are made sensitive to a single color from within the full spectrum, a reduced resolution image results because the pixel array has pixel spaces dedicated to only a single color of light within the full spectrum. Usually such an arrangement is formed in a checkerboard type pattern across the entire array.

In contrast, when partitioned spectrums of light are used a sensor can be made to be sensitive or responsive to the magnitude of all light energy because the pixel array will be instructed that it is sensing electromagnetic energy from a predetermined partition of the full spectrum of electromagnetic energy in each cycle. Therefore, to form an image the sensor need only be cycled with a plurality of differing partitions from within the full spectrum of light and then reassembling the image to display a predetermined mixture of color values for every pixel across the array. Accordingly, a higher resolution image is also provided because there are reduced distances as compared to a Bayer sensor between pixel centers of the same color sensitivity for each of the color pulses. As a result, the formed colored image has a higher modulation transfer function (MTF). Because the image from each color partition frame cycle, has a higher resolution, the resultant image created when the partitioned light frames are combined into a full color frame, also has a higher resolution. In other words, because each and every pixel within the array (instead of, at most, every second pixel in a sensor with color filter) is sensing the magnitudes of energy for a given pulse and a given scene, just fractions of time apart, a higher resolution image is created for each scene with less derived (less accurate) data needing to be introduced.

For example, white or full spectrum visible light is a combination of red, green and blue light. In the embodiment shown in FIG. 6, it can be seen that in both the partitioned spectrum process 620 and full spectrum process 610 the time to capture an image is t(0) to t(1). In the full spectrum process 610, white light or full spectrum electromagnetic energy is emitted at 612. At 614, the white or full spectrum electromagnetic energy is sensed. At 616, the image is processed and displayed. Thus, between time t(0) and t(1), the image has been processed and displayed. Conversely, in the partitioned spectrum process 620, a first partition is emitted at 622 and sensed at 624. At 626, a second partition is emitted and then sensed at 628. At 630, a third partition is emitted and sensed at 632. At 634, the image is processed and displayed. It will be appreciated that any system using an image sensor cycle that is at least two times faster than the white light cycle is intended to fall within the scope of the disclosure.

Figure 6:
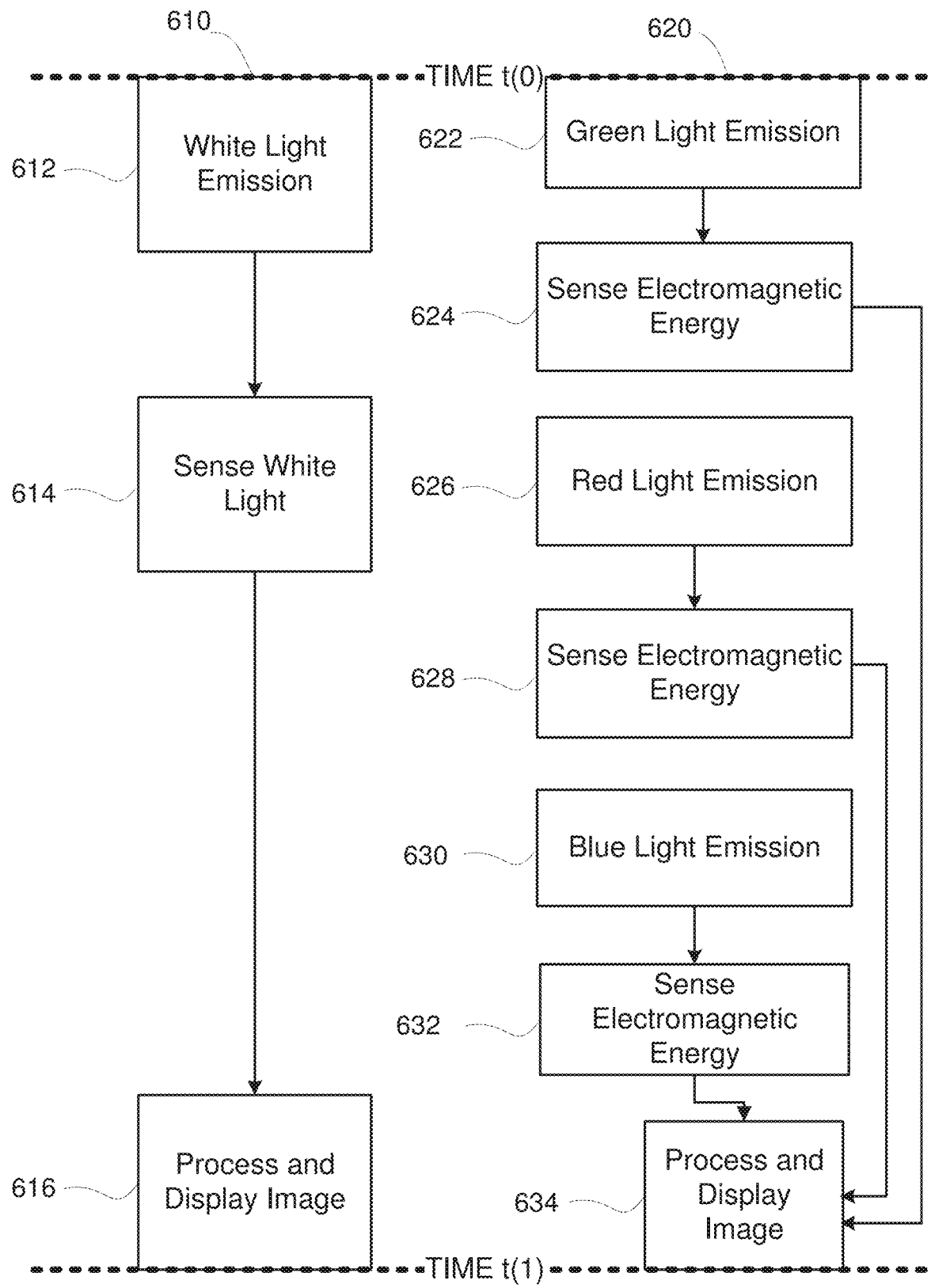
FIG. 6 illustrates a schematic of two distinct processes over a period of time from t(0) to t(1) for recording a frame of video for full spectrum light and partitioned spectrum light, according to one embodiment.

As can be seen graphically in the embodiment illustrated in FIG. 6 between times t(0) and t(1), the sensor for the partitioned spectrum system 620 has cycled three times for every one of the full spectrum system. In the partitioned spectrum system 620, the first of the three sensor cycles are for a green spectrum 622 and 624, the second of the three is for a red spectrum 626 and 628, and the third is for a blue spectrum 630 and 632. Thus, in an embodiment, wherein the display device (LCD panel) operates at 50-60 frames per second, a partitioned light system should operate at 150-180 frames per second to maintain the continuity and smoothness of the displayed video.

In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
  i. Green pulse;
  ii. Red pulse;
  iii. Blue pulse;
  iv. Green pulse;
  v. Red pulse;
  vi. Blue pulse;
  vii. Infra-red (IR) pulse;
  viii. (Repeat)

As can be seen in the example, an infrared partition or a specialized wavelength partition (e.g., 513-545 nm, 565-585 nm, and/or 900-100 nm) may be pulsed at a rate differing from the rates of the other partition pulses. This may be done to emphasize a certain aspect of the scene, with the IR data simply being overlaid with the other data in the video output to make the desired emphasis. It should be noted that the addition of an electromagnetic partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a partition pulse that is represented less in a pulse pattern (infrared in an above example), would result in an increase of less than 20% of the cycling speed of the sensor in order accommodate the irregular partition sampling.

In an embodiment, an electromagnetic partition may be emitted that is sensitive to dyes or materials that are used to highlight aspects of a scene. In the embodiment, it may be sufficient to highlight the location of the dyes or materials without need for high resolution. In such an embodiment, the dye sensitive electromagnetic partition may be cycled much less frequently than the other partitions in the system to include the emphasized data.

In various embodiments, the pulse cycle pattern may include any of the following wavelengths in any suitable order. Such wavelengths may be particularly suited for determining multispectral or hyperspectral image data or for determining image data based on a fluorescent reagent relaxation emission:
  i. 465±5 nm;
  ii. 533±4 nm;
  iii. 638±5 nm;
  iv. 780±5 nm;
  v. 805±5 nm;
  vi. 975±5 nm;
  vii. 577±2 nm; or
  viii. 523±4 nm.

Figure 7A:
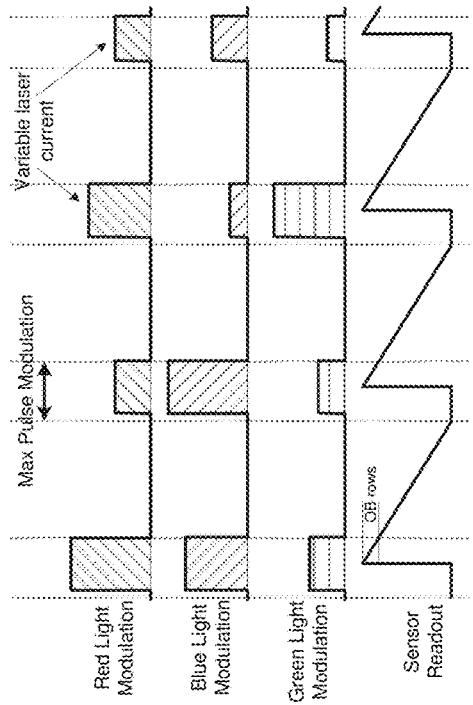
FIGS. 7A-7E illustrate schematic views of the processes over an interval of time for recording a frame of video for both full spectrum light and partitioned spectrum light in accordance with the principles and teachings of the disclosure.
Figure 7B:
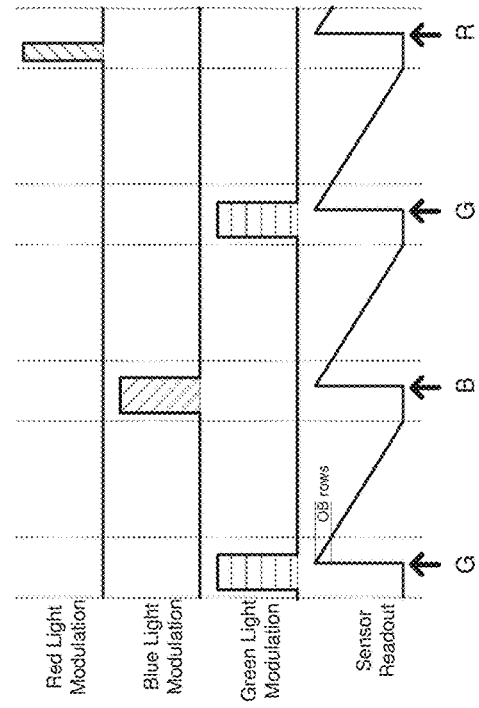
Figure 7C:
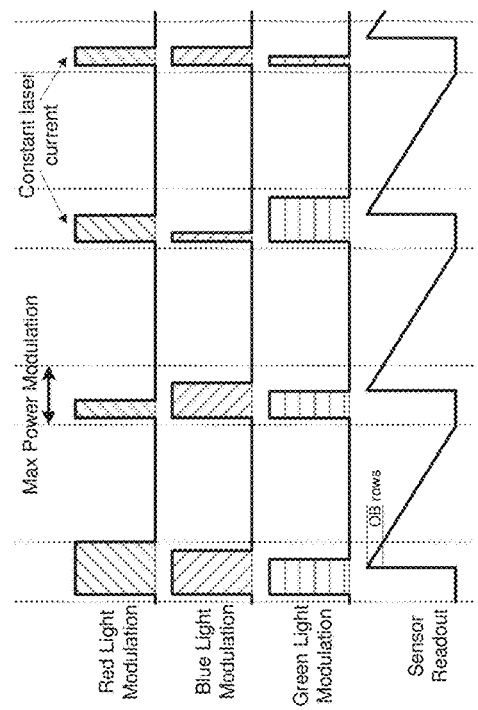

The partition cycles may be divided so as to accommodate or approximate various imaging and video standards. In an embodiment, the partition cycles may comprise pulses of electromagnetic energy in the Red, Green, Blue spectrum as follows as illustrated best in FIGS. 7A-7D. In FIG. 7A, the different light intensities have been achieved by modulating the light pulse width or duration within the working range shown by the vertical grey dashed lines. In FIG. 7B, the different light intensities have been achieved by modulating the light power or the power of the electromagnetic emitter, which may be a laser or LED emitter, but keeping the pulse width or duration constant. FIG. 7C shows the case where both the light power and the light pulse width are being modulated, leading to greater flexibility. The partition cycles may use CMY, IR and ultraviolet using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

Figure 7D:
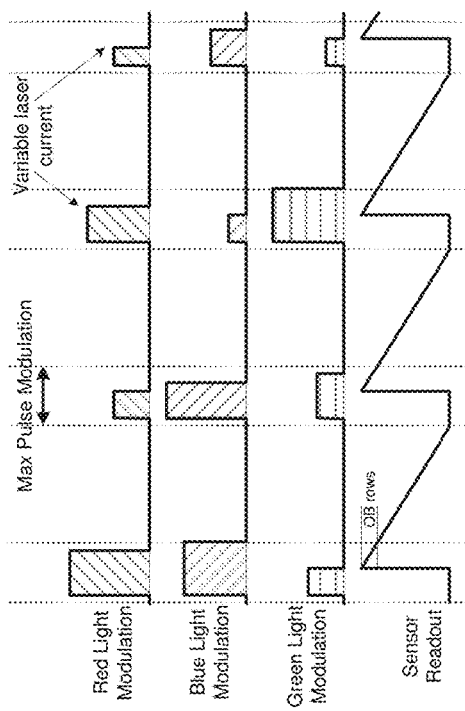

In an embodiment using color spaces Green-Blue-Green-Red (as seen in FIG. 7D) it may be desirous to pulse the luminance components more often than the chrominance components because users are generally more sensitive to light magnitude differences than to light color differences. This principle can be exploited using a mono-chromatic sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

Figure 7E:
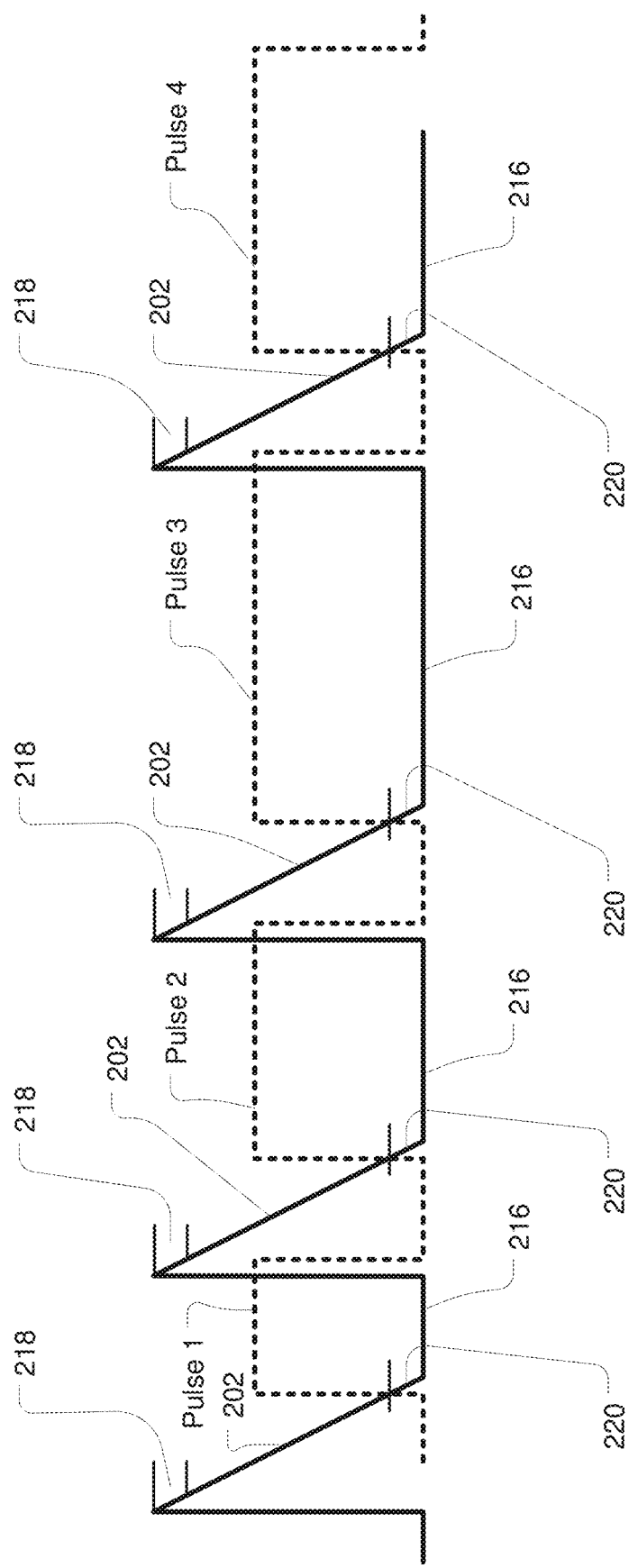

In an embodiment, duplicating the pulse of a weaker partition may be used to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E where the light pulses are different from frame to frame. The sensor may be built to be able to program different blanking times with a repeating pattern of 2 or 3 or 4 or n frames. In FIG. 7E, 4 different light pulses are illustrated, and Pulse 1 may repeat for example after Pulse 4 and may have a pattern of 4 frames with different blanking times. This technique can be used to place the most powerful partition on the smallest blanking time and therefore allow the weakest partition to have wider pulse on one of the next frames without the need of increasing the readout speed. The reconstructed frame can still have a regular pattern from frame to frame as it is constituted of many pulsed frames.

Figure 8:
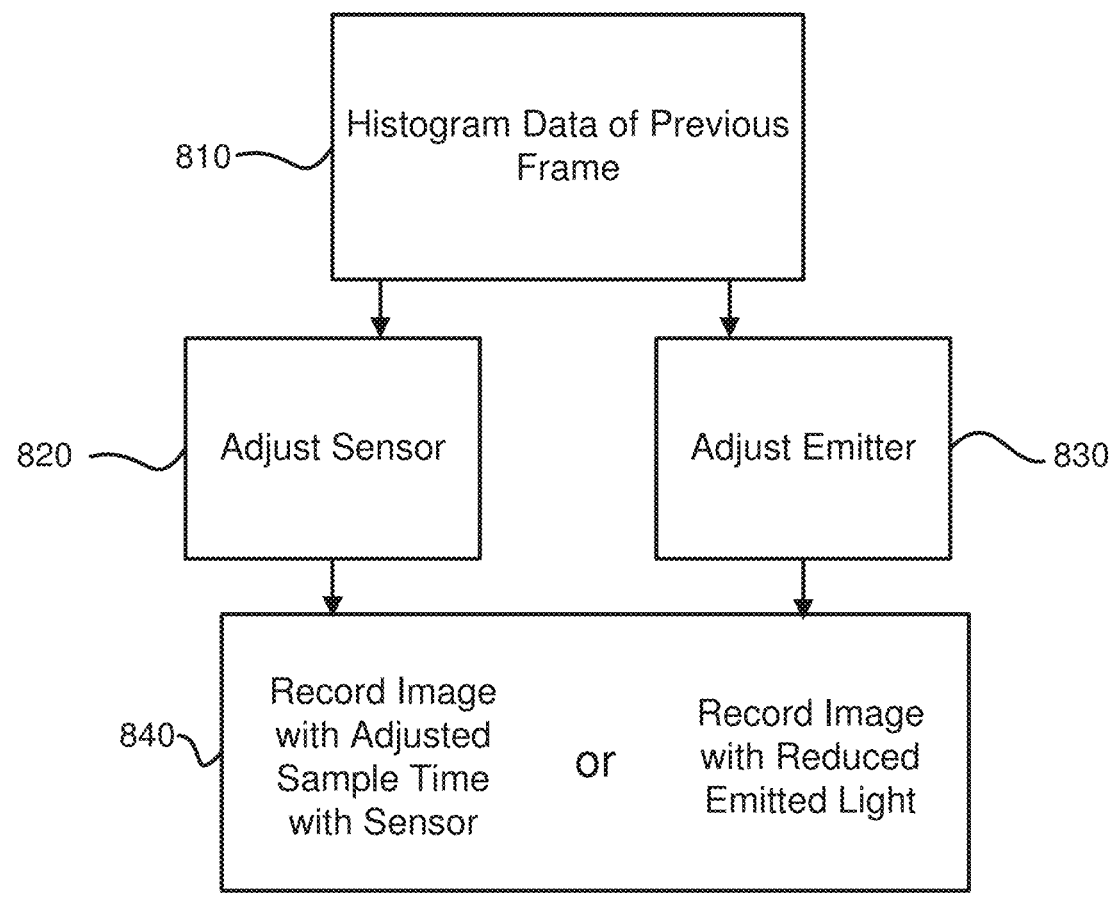
FIGS. 8-12 illustrate the adjustment of both the electromagnetic emitter and the sensor, wherein such adjustment may be made concurrently in some embodiments in accordance with the principles and teachings of the disclosure.
Figure 9:
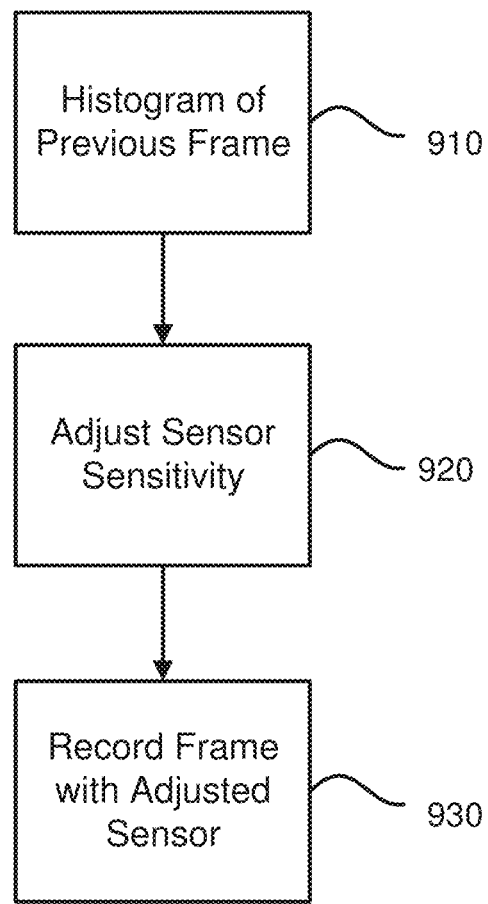

As can be seen in FIG. 8, because each partitioned spectrum of light may have different energy values, the sensor and/or light emitter may be adjusted to compensate for the differences in the energy values. At 810, the data obtained from the histogram from a previous frame may be analyzed. At 820, the sensor may be adjusted as noted below. Additionally, at 830, the emitter may be adjusted. At 840, the image may be obtained from the adjusted sample time from the sensor or the image may be obtained with adjusted (either increased or decreased) emitted light, or a combination of the above. For example, because the red light spectrum is more readily detected by a sensor within the system than the blue light spectrum, the sensor can be adjusted to be less sensitive during the red partition cycle and more sensitive during the blue partition cycle because of the low Quantum Efficiency that the blue partition has with respect to silicon (illustrated best in FIG. 9). Similarly, the emitter may be adjusted to provide an adjusted partition (e.g., higher or lower intensity and duration). Further, adjustments may be made at the sensor and emitter level both. The emitter may also be designed to emit at one specific frequency or may be changed to emit multiple frequencies of a specific partition to broaden the spectrum of light being emitted, if desired for a particular application.

Figure 10:
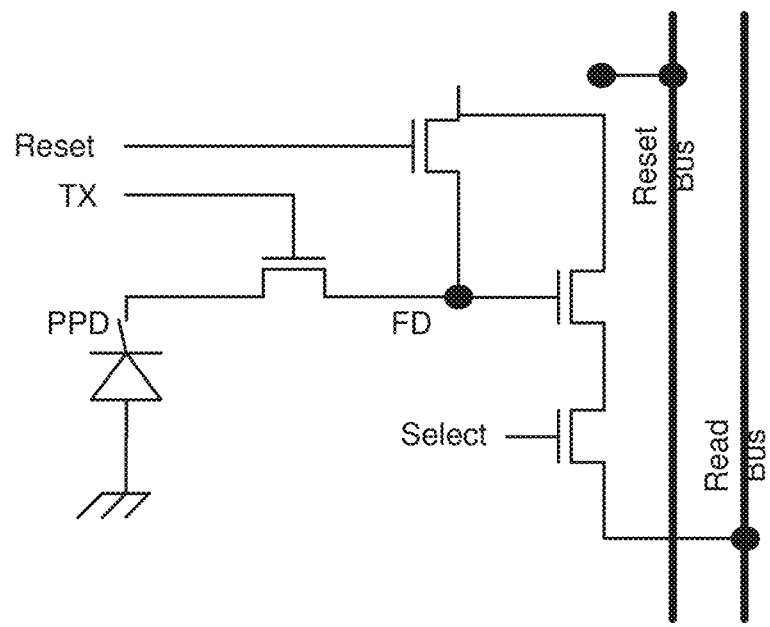

FIG. 10 shows a schematic of an unshared 4T pixel. The TX signal is used to transfer accumulated charges from the photo diode (PPD) to the floating diffusion (FD). The reset signal is used to reset the FD to the reset bus. If reset and TX signals are "On" at the same time, the PPD is constantly reset (each photo charge generated in the PPD is directly collected at the reset bus) and the PPD is always empty. Usual pixel array implementation includes a horizontal reset line that attaches the reset signals of all pixels within one row and a horizontal TX line that attaches the TX signals of all pixels within one row.

Figure 11:
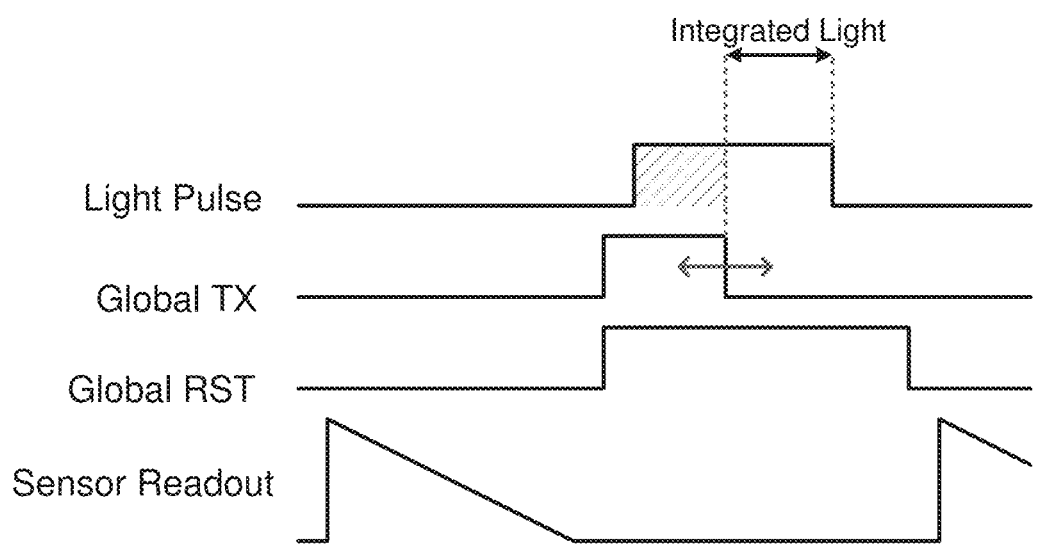

In an embodiment, timing of the sensor sensibility adjustment is illustrated, and sensor sensibility adjustment can be achieved using a global reset mechanism (i.e., a means of firing all pixel array reset signals at once) and a global TX mechanism (i.e., a means of firing all pixel array TX signals at once). This is shown in FIG. 11. In this case, the light pulse is constant in duration and amplitude, but the light integrated in all pixels starts with the "on" to "off" transition of the global TX and ends with the light pulse. Therefore, the modulation is achieved by moving the falling edge of the global TX pulse.

Figure 12:
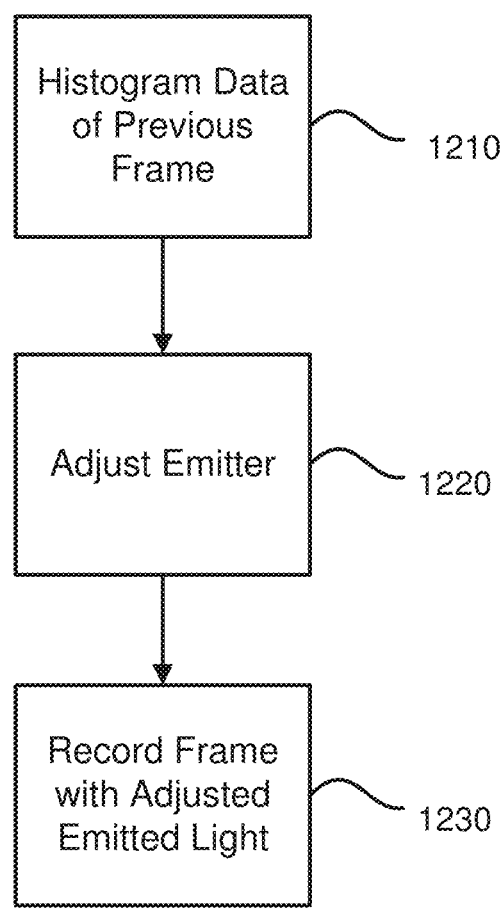

Conversely, the emitter may emit red light at a lesser intensity than blue light to produce a correctly exposed image (illustrated best in FIG. 12). At 1210, the data obtained from the histogram from a previous frame may be analyzed. At 1220, the emitter may be adjusted. At 1230, the image may be obtained from the adjusted emitted light. Additionally, in an embodiment both the emitter and the sensor can be adjusted concurrently.

Reconstructing the partitioned spectrum frames into a full spectrum frame for later output could be as simple as blending the sensed values for each pixel in the array in some embodiments. Additionally, the blending and mixing of values may be simple averages or may be tuned to a predetermined lookup table (LUT) of values for desired outputs. In an embodiment of a system using partitioned light spectrums, the sensed values may be post-processed or further refined remotely from the sensor by an image or secondary processor, and just before being output to a display.

Figure 13:
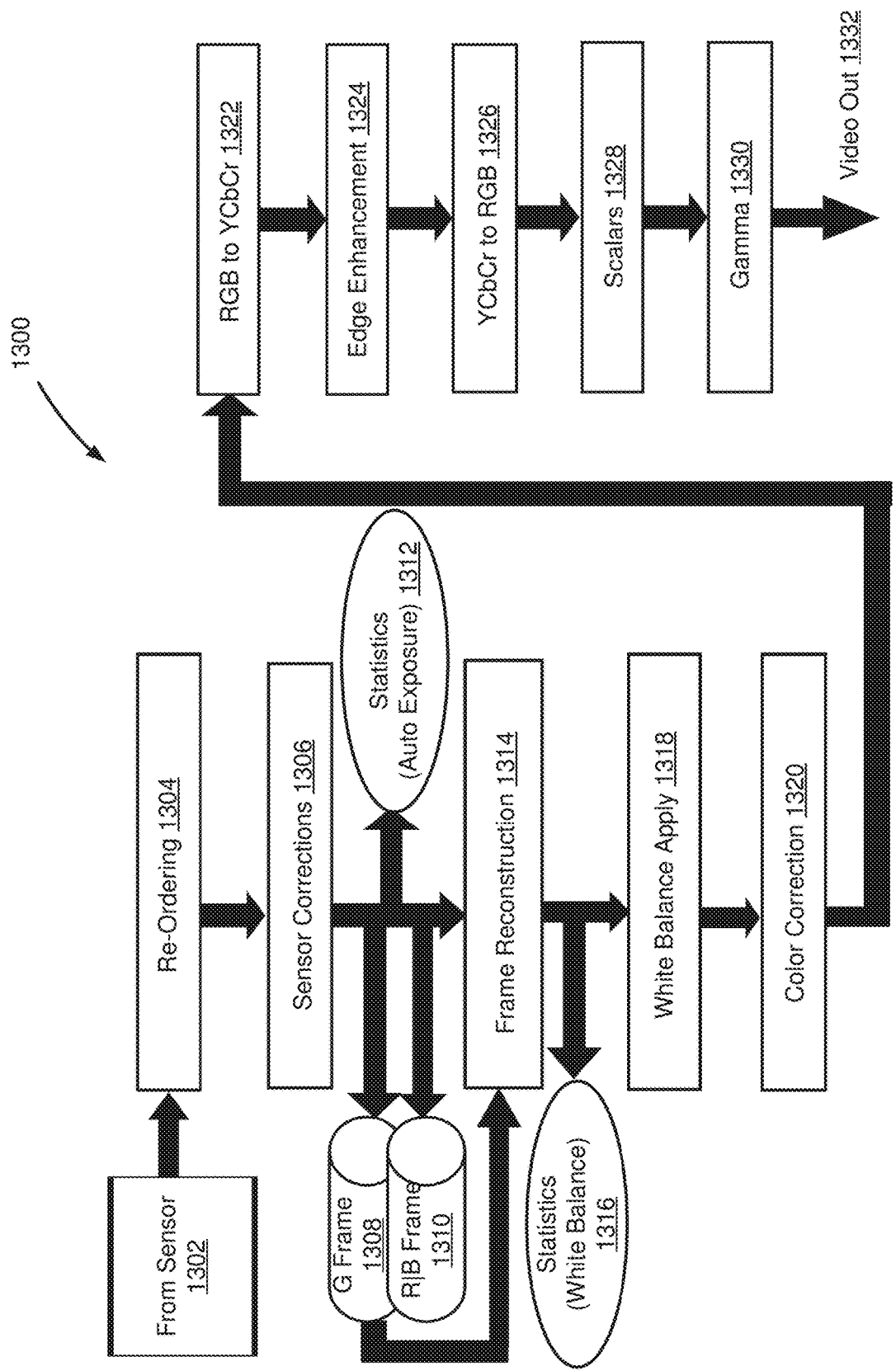
FIGS. 13-21 illustrate sensor correction methods and hardware schematics for use with a partitioned light system, according to embodiments of the disclosure.

FIG. 13 illustrates a basic example at 1300 of a monochrome ISP and how an ISP chain may be assembled for the purpose of generating sRGB image sequences from raw sensor data, yielded in the presence of the G-R-G-B light pulsing scheme.

Figure 21:
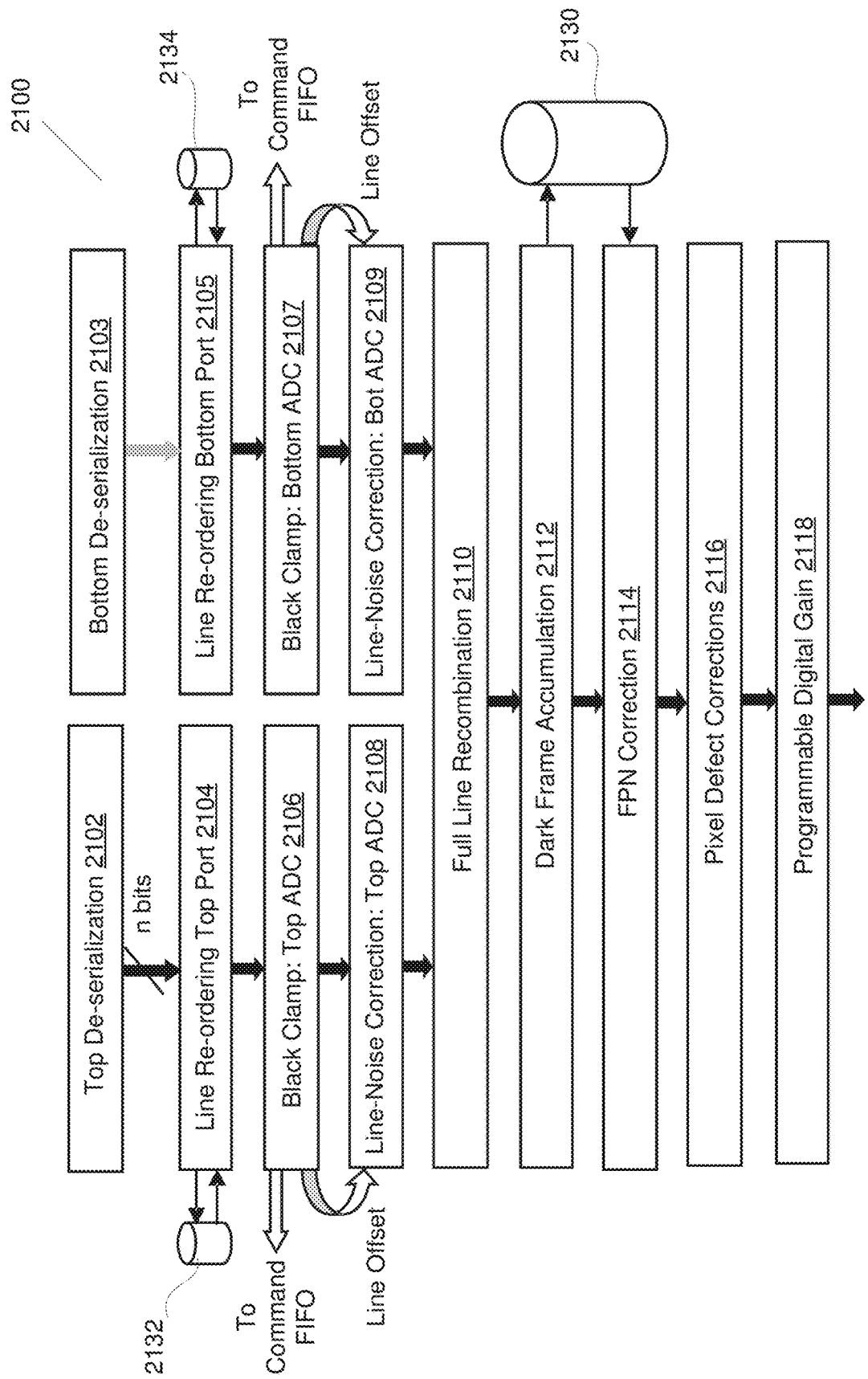

The first stage is concerned with making corrections (see 1302, 1304 and 1306 in FIG. 13) to account for any non-idealities in the sensor technology for which it is most appropriate to work in the raw data domain (see FIG. 21).

At the next stage, two frames (see 1308 and 1310 in FIG. 13) would be buffered since each final frame derives data from three raw frames. The frame reconstruction at 1314 would proceed by sampling data from the current frame and the two buffered frames (1308 and/or 1310). The reconstruction process results in full color frames in linear RGB color space.

In this example, the white balance coefficients at 1318 and color correction matrix at 1320 are applied before converting to YCbCr space at 1322 for subsequent edge enhancement at 1324. After edge enhancement at 1324, images are transformed back to linear RGB at 1326 for scaling at 1328, if applicable.

Finally, the gamma transfer function at 1330 would be applied to translate the data into the sRGB domain at 1332.

Figure 14:
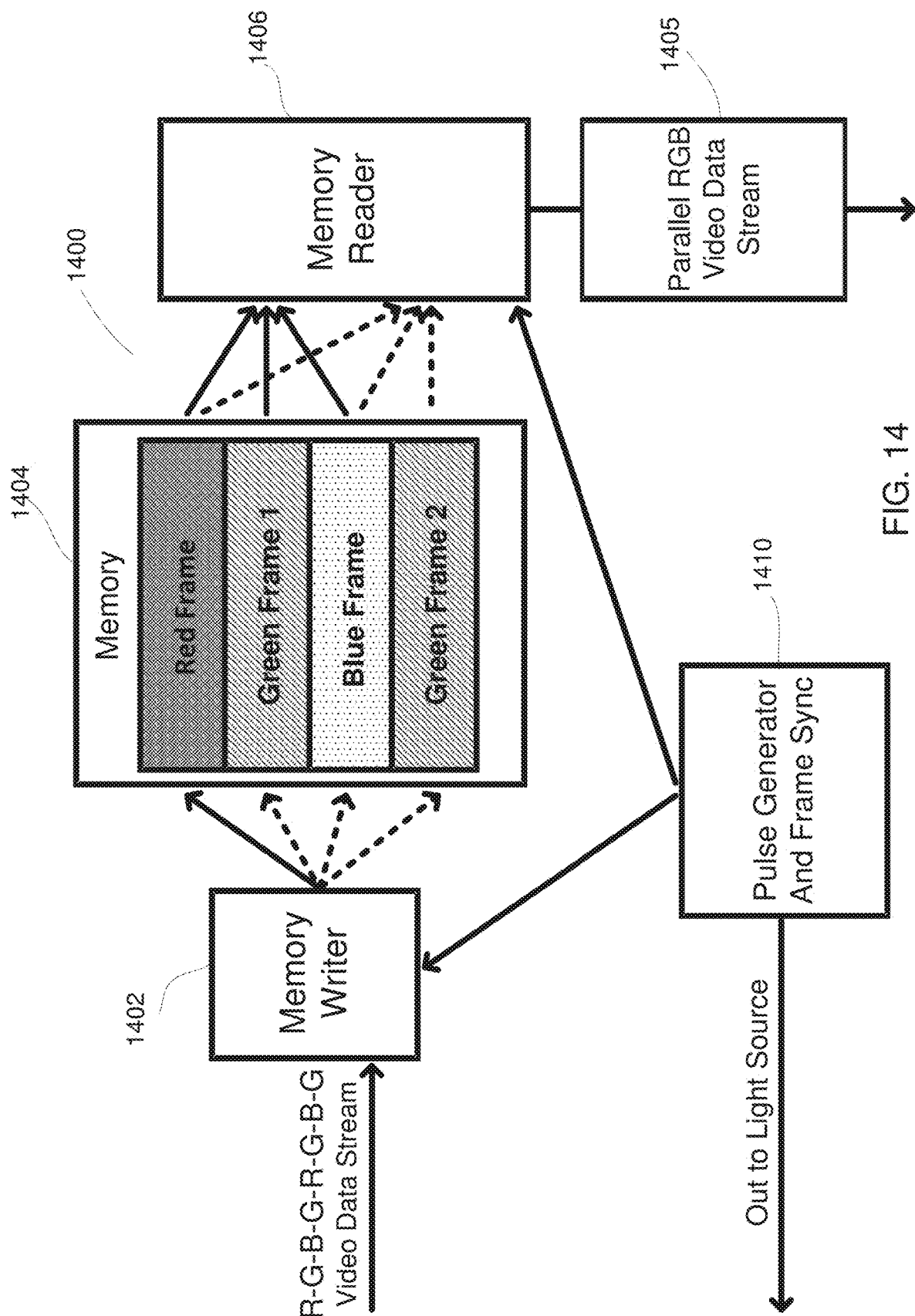

FIG. 14 is an embodiment example of color fusion hardware. The color fusion hardware takes in an RGBGRGBGRGBG video data stream at 1402 and converts it to a parallel RGB video data stream at 1405. The bit width on the input side may be, e.g., 12 bits per color. The output width for that example would be 36 bits per pixel. Other embodiments may have different initial bit widths and 3 times that number for the output width. The memory writer block takes as its input the RGBG video stream at 1402 and writes each frame to its correct frame memory buffer at 1404 (the memory writer triggers off the same pulse generator 1410 that runs the laser light source). As illustrated at 1404, writing to the memory follows the pattern, Red, Green 1, Blue, Green 2, and then starts back with Red again. At 1406, the memory reader reads three frames at once to construct an RGB pixel. Each pixel is three times the bit width of an individual color component. The reader also triggers off the laser pulse generator at 1410. The reader waits until Red, Green 1 and Blue frames have been written, then proceeds to read them out in parallel while the writer continues writing Green 2 and starts back on Red. When Red completes the reader begins reading from Blue, Green 2 and Red. This pattern continues indefinitely.

Figure 15:
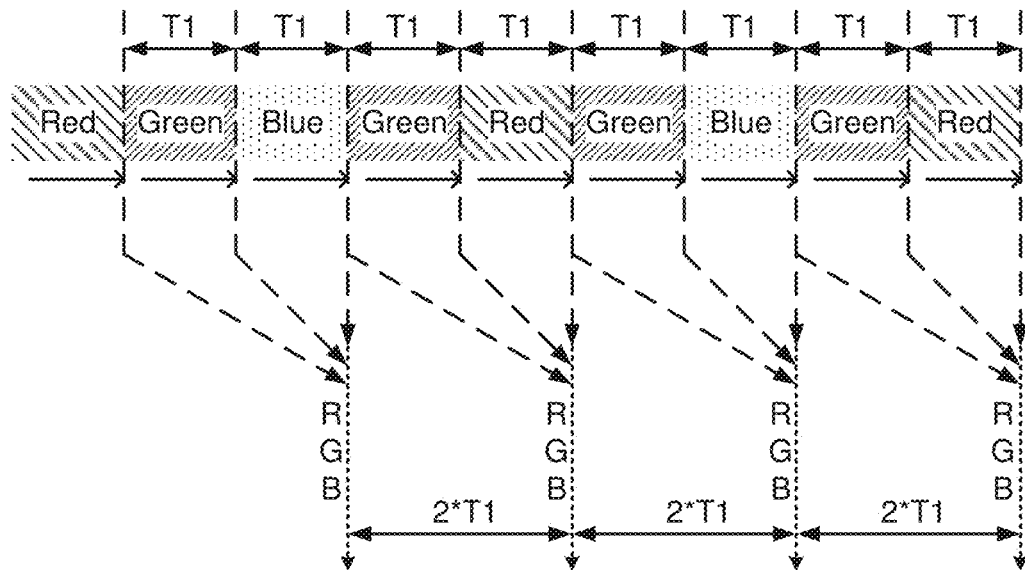
Figure 16:
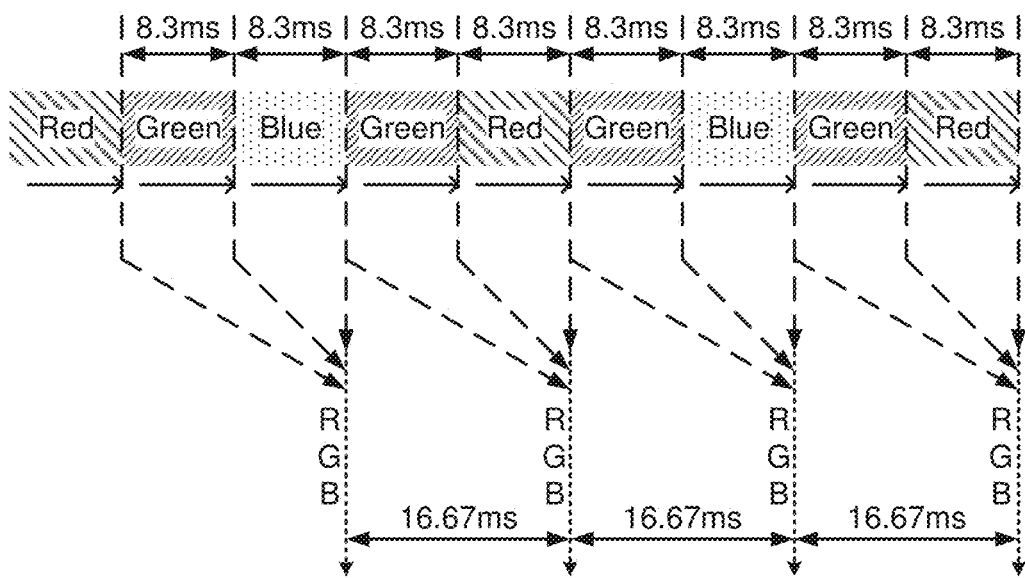

Referring now to FIGS. 15 and 16, the RG1BG2RG1BG2 pattern reconstruction illustrated in FIG. 16 allows 60 fps output with 120 fps input in an embodiment. Each consecutive frame contains either a red or blue component from the previous frame. In FIG. 16, each color component is available in 8.3 ms and the resulting reconstructed frame has a period of 16.67 ms. In general, for this pulsing scheme, the reconstructed frame has a period twice of that of the incoming colored frame as shown in FIG. 15. In other embodiments, different pulsing schemes may be employed. For example, embodiments may be based on the timing of each color component or frame (T1) and the reconstructed frame having a period twice that of the incoming color frame (2×T1). Different frames within the sequence may have different frame periods and the average capture rate could be any multiple of the final frame rate.

FIGS. 17-20 illustrate color correction methods and hardware schematics for use with a partitioned light system. It is common in digital imaging to manipulate the values within image data to correct the output to meet user expectations or to highlight certain aspects of the imaged object. Most commonly this is done in satellite images that are tuned and adjusted to emphasize one data type over another. Most often, in satellite acquired data there is the full spectrum of electromagnetic energy available because the light source is not controlled, i.e., the sun is the light source. In contrast, there are imaging conditions where the light is controlled and even provided by a user. In such situations, calibration of the image data is still desirable, because without calibration improper emphasis may be given to certain data over other data. In a system where the light is controlled by the user, it is advantageous to provide emissions of light that are known to the user and may be only a portion of the electromagnetic spectrum or a plurality of portions of the full electromagnetic spectrum. Calibration remains important to meet the expectations of the users and check for faults within the system. One method of calibration can be a table of expected values for a given imaging condition that can be compared to the data from the sensor. An embodiment may include a color neutral scene having known values that should be output by the imaging device and the device may be adjusted to meet those known values when the device samples the color neutral scene.

Figure 17:
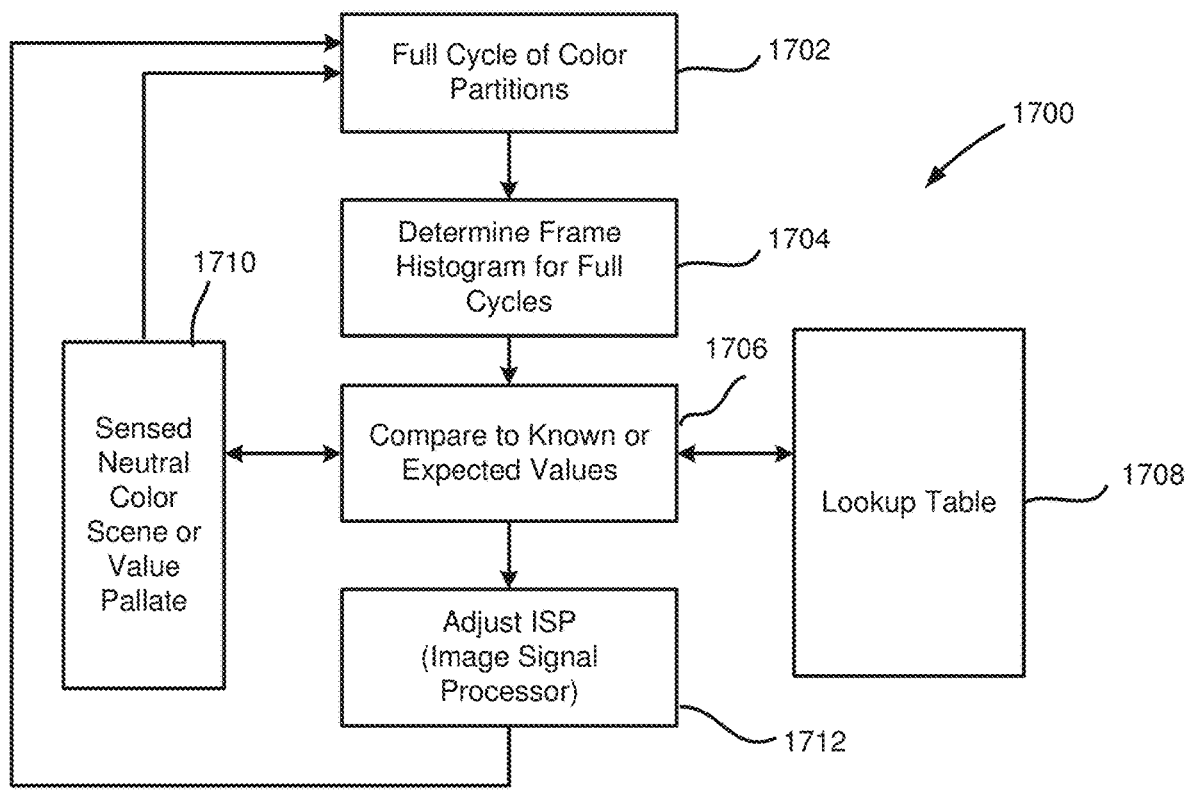

In use, and upon start up, the system may sample a color neutral scene at 1710 (as illustrated in FIG. 17) by running a full cycle of a plurality of electromagnetic spectrum partitions at 1702. A table of values 1708 may be formed to produce a histogram for the frame at 1704. The values of the frame can be compared to the known or expected values from the color neutral scene at 1706. The imaging device may then be adjusted to meet the desired output at 1712. In an embodiment illustrated in FIG. 17, the system may comprise an image signal processor (ISP) that may be adjusted to color correct the imaging device.

It should be noted that because each partitioned spectrum of light may have different energy values, the sensor and/or light emitter may be adjusted to compensate for the differences in the energy values. For example, in an embodiment, because the blue light spectrum has a lower quantum efficiency than the red light spectrum with regard to silicon based imagers, the sensor's responsiveness can then be adjusted to be less responsive during the red cycle and more responsive during the blue cycle. Conversely, the emitter may emit blue light at a higher intensity, because of the lower quantum efficiency of the blue light, than red light to produce a correctly exposed image.

Figure 18:
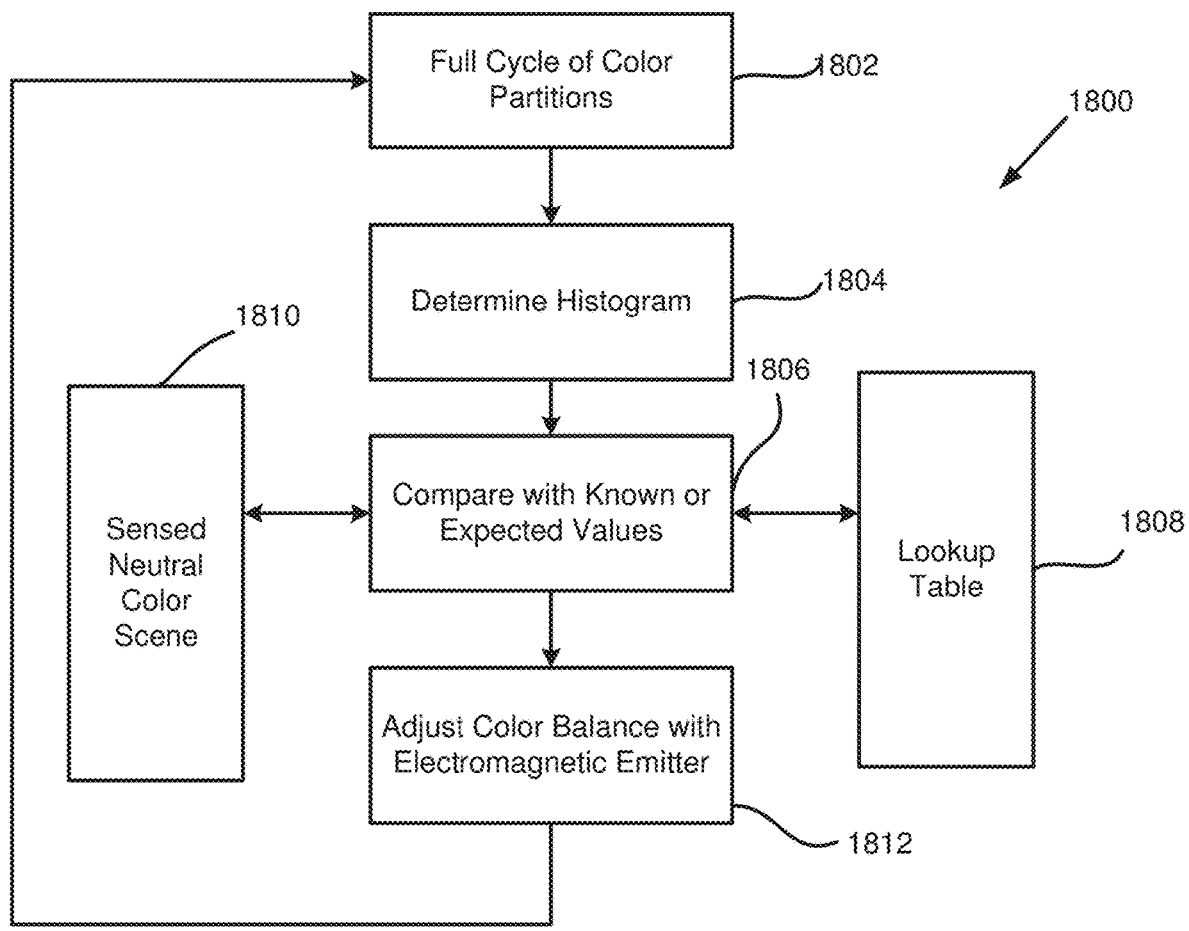
Figure 19:
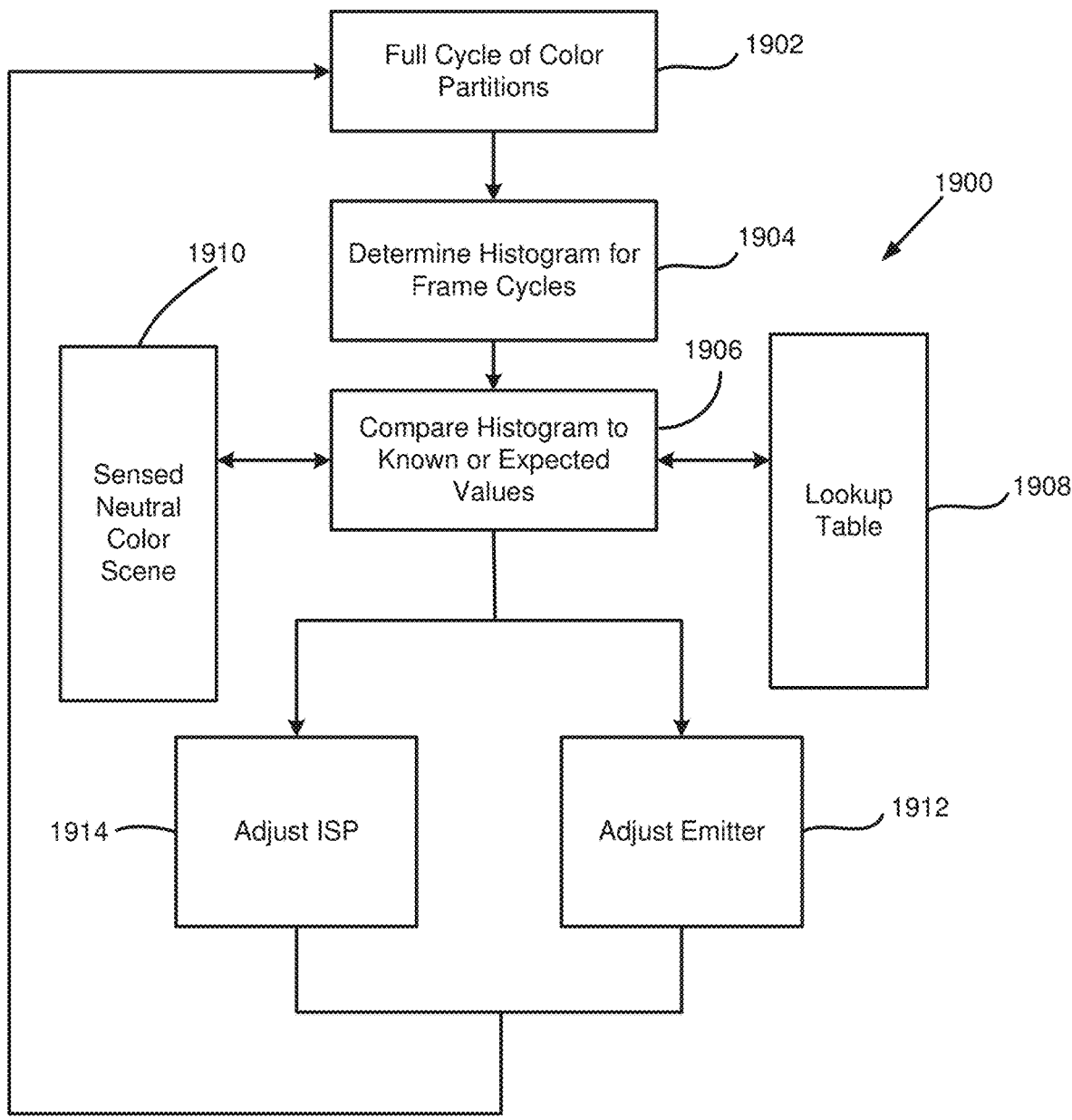

In an embodiment illustrated in FIG. 18, where the light source emissions are provided and controllable by the system, adjustment of those light emissions can be made to color correct an image at 1800. Adjustments may be made to any aspect of the emitted light such as magnitude, duration (i.e., time-on), or the range within the spectrum partition. Additionally, both the emitter and the sensor can be adjusted concurrently in some embodiments as shown in FIG. 19.

Figure 20:
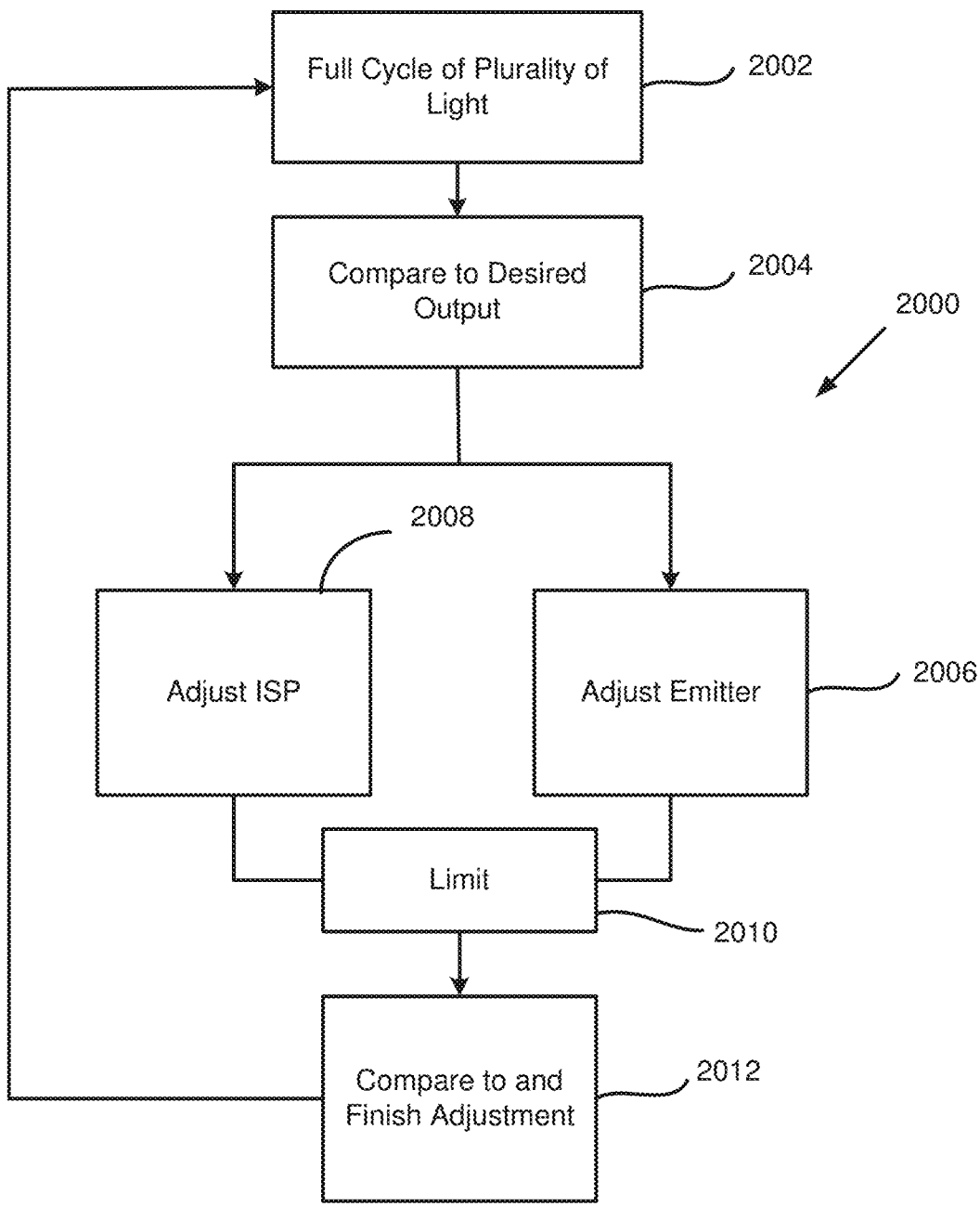

To reduce the amount of noise and artifacts within the outputted image stream or video, fractionalized adjustments may be made to the sensor or emitter within the system as can be seen in FIG. 20. Illustrated in FIG. 20 is a system 2000 where both the emitter 2006 and the sensor 2008 can be adjusted, but an imaging device where either the emitter or sensor is adjusted during use or for a portion of use is also contemplated and is within the scope of this disclosure. It may be advantageous to adjust only the emitter during one portion of use and adjust only the sensor during another portion of use, while further yet adjusting both concurrently during a portion of use. In any of the above embodiments, improved image quality may be obtained by limiting the overall adjustments that the system can make between frame cycles. In other words, an embodiment may be limited such that the emitter may only be adjusted a fraction of its operational range at any time between frames. Likewise, the sensor may be limited such that it may only be adjusted a fraction of its operational range at any time between frames. Furthermore, both the emitter and sensor may be limited such that they may only be adjusted together at a fraction of their respective operational ranges at any time between frames in an embodiment.

In an exemplary embodiment, a fractional adjustment of the components within the system may be performed, for example, at about 0.1 dB of the operational range of the components to correct the exposure of the previous frame. The 0.1 dB is merely an example and it should be noted that is other embodiments the allowed adjustment of the components may be any portion of their respective operational ranges. The components of the system can change by intensity or duration adjustment that is generally governed by the number of bits (resolution) output by the component. The component resolution may be typically between a range of about 10-24 bits but should not be limited to this range as it is intended to include resolutions for components that are yet to be developed in addition to those that are currently available. For example, after a first frame it is determined that the scene is too blue when observed, then the emitter may be adjusted to decrease the magnitude or duration of the pulse of the blue light during the blue cycle of the system by a fractional adjustment as discussed above, such as about 0.1 dB.

In this exemplary embodiment, more than 10 percent may have been needed, but the system has limited itself to 0.1 dB adjustment of the operational range per system cycle. Accordingly, during the next system cycle the blue light can then be adjusted again, if needed. Fractionalized adjustment between cycles may have a damping effect of the outputted imaged and will reduce the noise and artifacts when operating emitters and sensors at their operation extremes. It may be determined that any fractional amount of the components' operational range of adjustment may be used as a limiting factor, or it may be determined that certain embodiments of the system may comprise components that may be adjusted over their entire operational range.

Additionally, the optical black area of any image sensor may be used to aid in image correction and noise reduction. In an embodiment, the values read from the optical black area may be compared to those of the active pixel region of a sensor to establish a reference point to be used in image data processing. FIG. 21 shows the kind of sensor correction processes that might be employed in a color pulsed system. CMOS image sensors typically have multiple non-idealities that have a detrimental effect on image quality, particularly in low light. Chief among these are fixed pattern noise and line noise. Fixed pattern noise is a dispersion in the offsets of the sense elements. Typically, most of the FPN is a pixel to pixel dispersion which stems, among other sources, from random variations in dark current from photodiode to photodiode. This looks very unnatural to the viewer. Even more egregious is column FPN, resulting from offsets in the readout chain associated with a particular columns of pixels. This results in perceived vertical stripes within the image.

Being in total control of the illumination has the benefit that entire frames of dark data may periodically be acquired and used to correct for the pixel and column offsets. In the illustrated example, a single frame buffer may be used to make a running average of the whole frame without light using, e.g., simple exponential smoothing. This dark average frame would be subtracted from every illuminated frame during regular operation.

Line-Noise is a stochastic temporal variation in the offsets of pixels within each row. Since it is temporal, the correction must be computed anew for each line and each frame. For this purpose, there are usually many optically blind (OB) pixels within each row in the array, which must first be sampled to assess the line offset before sampling the light sensitive pixels. The line offset is then simply subtracted during the line noise correction process.

In the example in FIG. 21, there are other corrections concerned with getting the data into the proper order, monitoring and controlling the voltage offset in the analog domain (black clamp) and identifying/correcting individual defective pixels.

Figure 22:
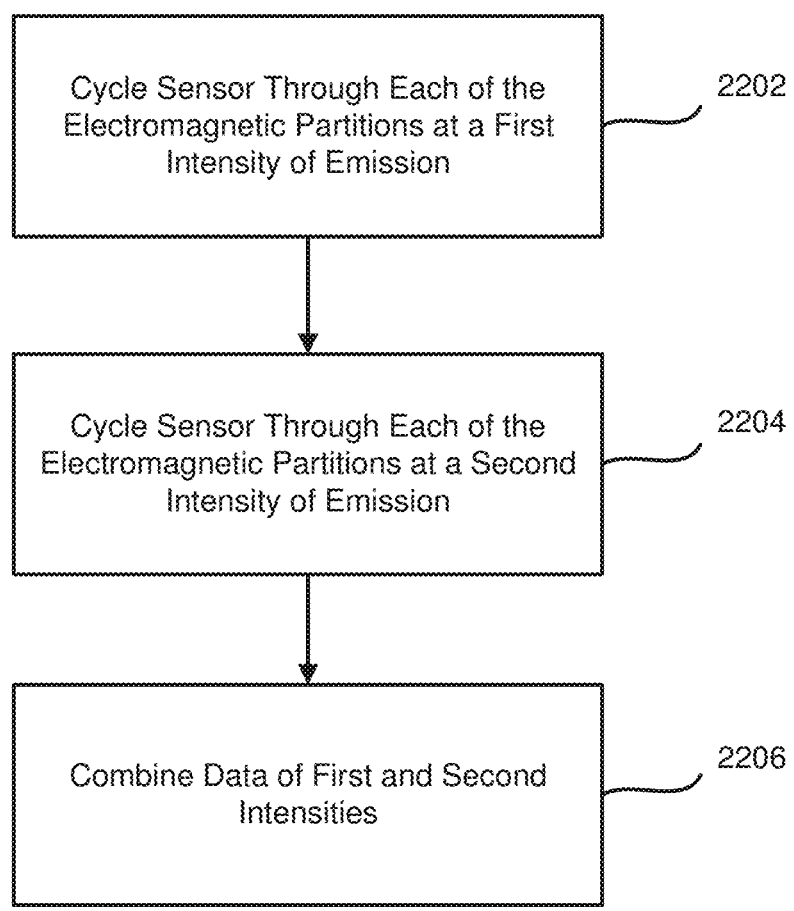
FIGS. 22-23 illustrate method and hardware schematics for increasing the dynamic range within a closed or limited light environment, according to embodiments of the disclosure.
Figure 23:
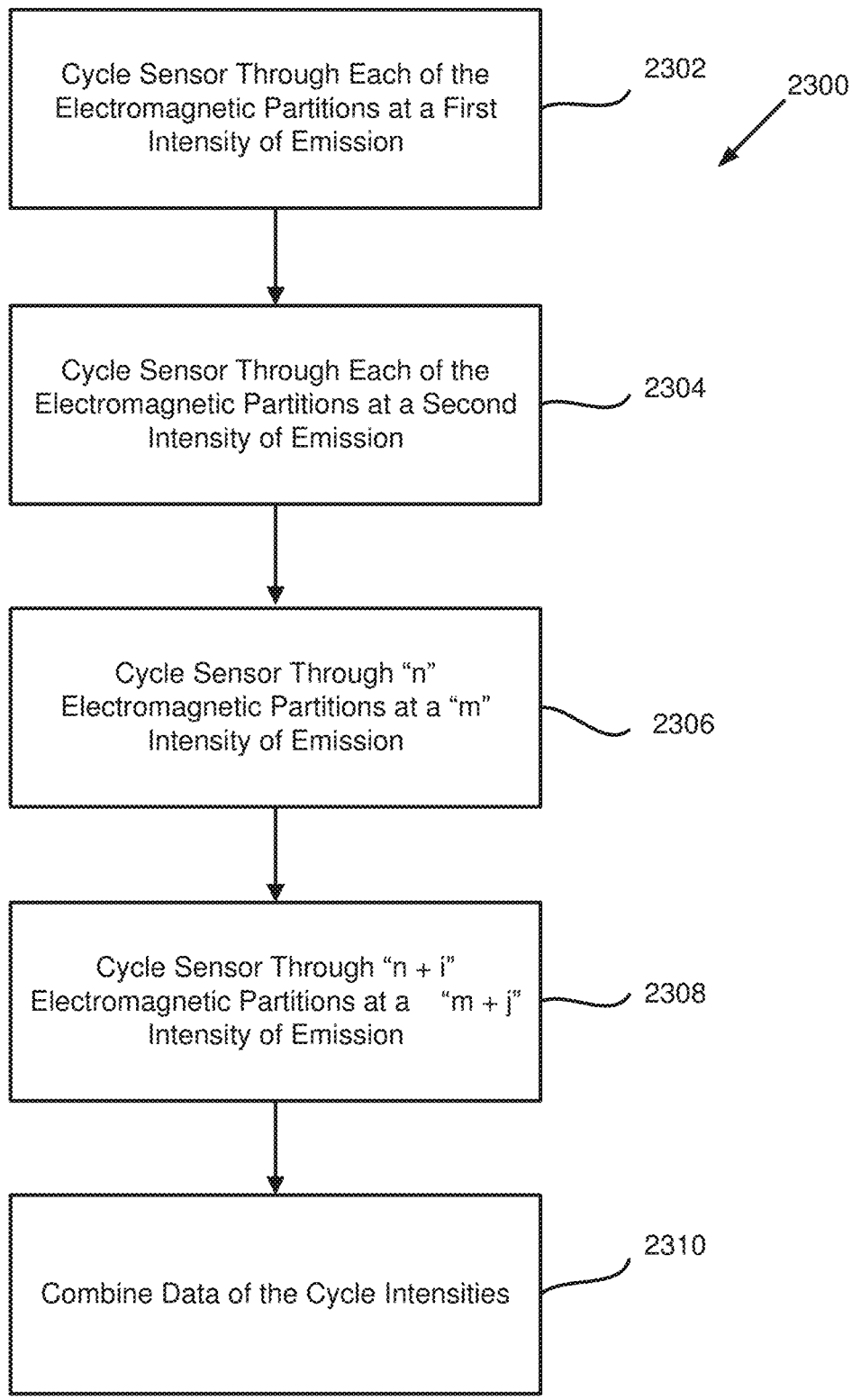

FIGS. 22 and 23 illustrate method and hardware schematics for increasing the dynamic range within a closed or limited light environment. In an embodiment, exposure inputs may be input at different levels over time and combine to produce greater dynamic range. As can be seen in FIG. 22, an imaging system may be cycled at a first intensity for a first cycle at 2202 and then subsequently cycled at a second intensity for a second cycle at 2204, and then by combining those first and second cycles into a single frame at 2206 so that greater dynamic range can be achieved. Greater dynamic range may be especially desirable because of the limited space environment in which an imaging device is used. In limited space environments that are light deficient or dark, except for the light provided by the light source, and where the light source is close to the light emitter, exposure has an exponential relationship to distance. For example, objects near the light source and optical opening of the imaging device tend to be over exposed, while objects farther away tend to be extremely under exposed because there is very little (in any) ambient light present.

As can be seen in FIG. 23, the cycles of a system having emissions of electromagnetic energy in a plurality of partitions may be serially cycled according to the partitions of electromagnetic spectrum at 2300. For example, in an embodiment where the emitter emits lasers in a distinct red partition, a distinct blue partition, and a distinct green partition, the two cycle data sets that are going to be combined may be in the form of:

i. red at intensity one at 2302,
  ii. red at intensity two at 2304,
  iii. blue at intensity one at 2302,
  iv. blue at intensity two at 2304,
  v. green at intensity one at 2302,
  vi. green at intensity two at 2304.

Alternatively, the system may be cycled in the form of:

i. red at intensity one at 2302,
  ii. blue at intensity one at 2302,
  iii. green at intensity one at 2302,
  iv. red at intensity two at 2304,
  v. blue at intensity two at 2304,
  vi. green at intensity two at 2304.

In such an embodiment, a first image may be derived from the intensity one values, and a second image may be derived from the intensity two values, and then combined or processed as complete image data sets at 2310 rather than their component parts.

It is contemplated to be within the scope of this disclosure that any number of emission partitions may be used in any order. As seen in FIG. 23, "n" is used as a variable to denote any number of electromagnetic partitions and "m" is used to denote any level of intensity for the "n" partitions. Such a system may be cycled in the form of:

i. n at intensity m at 2306,
  ii. n+1 at intensity m+1,
  iii. n+2 at intensity m+2,
  iv. n+i at intensity m+j at 2308.

Accordingly, any pattern of serialized cycles can be used to produce the desired image correction wherein "i" and "j" are additional values within the operation range of the imaging system.

Digital color cameras incorporate an image processing stage for the purpose of maximizing the fidelity of color reproduction. This is accomplished by means of a 3×3 matrix known as the Color Correction Matrix (CCM):

$$\begin{bmatrix} R \\ G \\ B \end{bmatrix}_{OUT} = \begin{bmatrix} R \\ G \\ B \end{bmatrix}_{IN} \begin{bmatrix} a & b & c \\ d & e & f \\ g & h & i \end{bmatrix}$$

The terms in the CCM are tuned using a set of reference colors (e.g., from a Macbeth chart) to provide the best overall match to the sRGB standard color space. The diagonal terms, a, e and i, are effectively white balance gains. Typically, though, the white balance is applied separately, and the sums of horizontal rows are constrained to be unity, in order no net gain is applied by the CCM itself. The off-diagonal terms effectively deal with color crosstalk in the input channels. Therefore, Bayer sensors have higher off-diagonals than 3-chip cameras since the color filer arrays have a lot of response overlap between channels.

There is a signal-to-noise ratio penalty for color correction which is dependent on the magnitude of the off-diagonal terms. A hypothetical sensor with channels that perfectly matched the sRGB components would have the identity matrix CCM:

$$\begin{bmatrix} R \\ G \\ B \end{bmatrix}_{OUT} = \begin{bmatrix} R \\ G \\ B \end{bmatrix}_{IN} \begin{bmatrix} 1 & 0 & 0 \\ 0 & 1 & 0 \\ 0 & 0 & 1 \end{bmatrix}$$

The signal to noise ratio evaluated in the green channel, for a perfect white photo signal of 10,000 e-per pixel (neglecting read noise) for this case would be:

$$SNR = \frac{10{,}000}{\sqrt{10{,}000}} = 100$$

Any departure from this degrades the SNR. Take e.g. the following CCM which has values that would not be unusual for a Bayer CMOS sensor:

$$\begin{bmatrix} R \\ G \\ B \end{bmatrix}_{OUT} = \begin{bmatrix} R \\ G \\ B \end{bmatrix}_{IN} \begin{bmatrix} 2.6 & -1.4 & -0.2 \\ -0.3 & 1.6 & -0.3 \\ 0 & -0.6 & 1.6 \end{bmatrix}$$

In this case, the green SNR:

$$SNR = \frac{(-3000 + 16{,}000 - 3000)}{\sqrt{(3000 + 16{,}000 - 3000)}} = 67.1$$

FIG. 24 shows the result of a full SNR simulation using D65 illumination for a typical Bayer sensor CCM for the case of using the identity matrix versus the tuned CCM. The SNR evaluated for the luminance component is about 6 dB worse as a consequence of the color correction.

Figure 25:
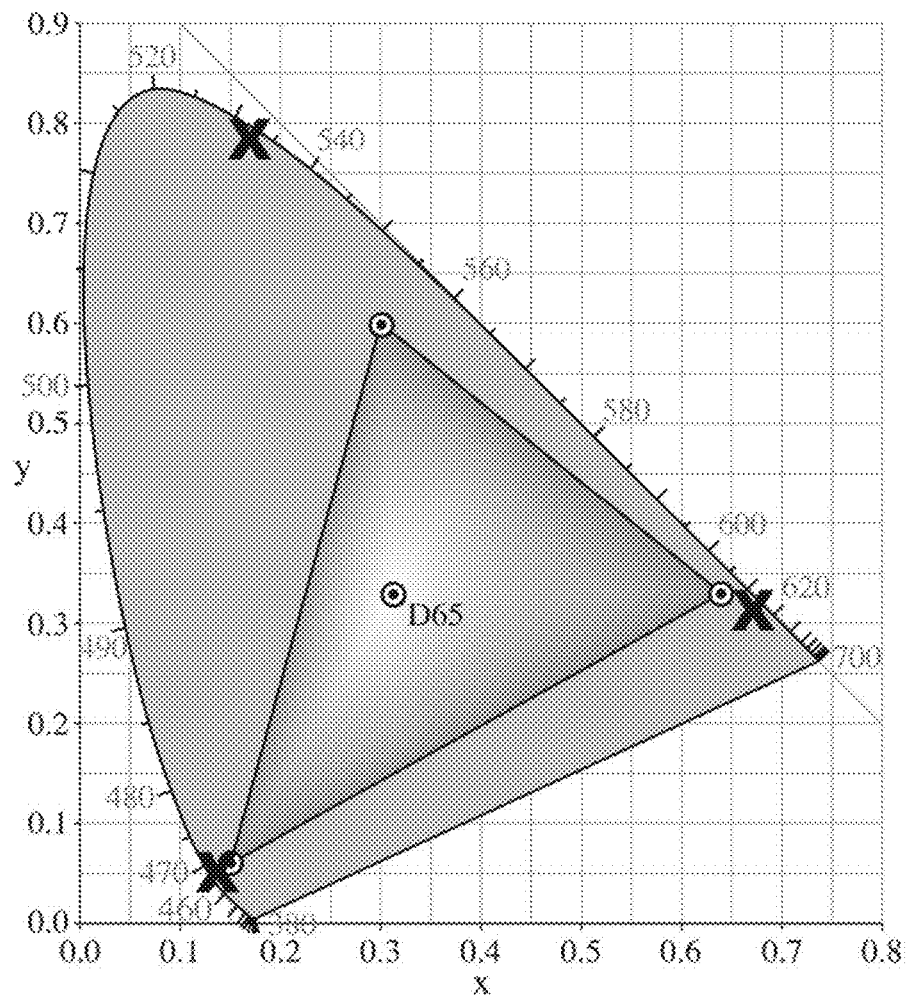
FIG. 25 illustrates the chromaticity of 3 monochromatic lasers compared to the sRGB gamut.

The system described in this disclosure uses monochromatic illumination at a plurality of discrete wavelengths, therefore there is no color crosstalk per se. The crosses in FIG. 25 indicate the positions of three wavelengths which are available via laser diode sources (465, 532 & 639 nm), compared the sRGB gamut which is indicated by the triangle.

The off-diagonal terms for the CCM is in this case are drastically reduced, compared with Bayer sensors, which provides a significant SNR advantage.

Figure 26:
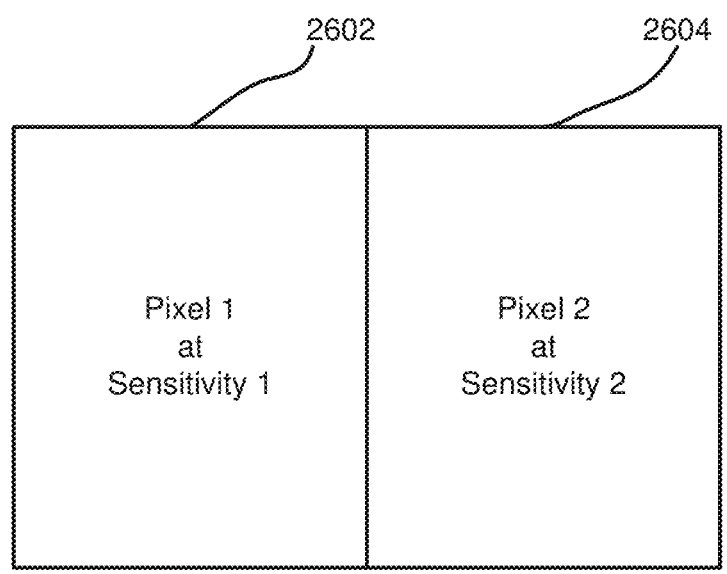
FIGS. 26-27B illustrate method and hardware schematics for increasing the dynamic range within a closed or limited light environment, according to embodiments of the disclosure.

FIG. 26 illustrates an imaging system having increased dynamic range as provided by the pixel configuration of the pixel array of the image sensor. As can be seen in the figure, adjacent pixels 2602 and 2604 may be set at differing sensitivities such that each cycle includes data produced by pixels that are more and less sensitive with respect to each other. Because a plurality of sensitivities can be recorded in a single cycle of the array the dynamic range may be increased if recorded in parallel, as opposed to the time dependent serial nature of other embodiments.

In an embodiment, an array may comprise rows of pixels that may be placed in rows based on their sensitivities. In an embodiment, pixels of differing sensitivities may alternate within a row or column with respect to its nearest neighboring pixels to from a checkerboard pattern throughout the array based on those sensitivities. The above may be accomplished through any pixel circuitry share arrangement or in any stand-alone pixel circuit arrangement.

Wide dynamic range can be achieved by having multiple global TX, each TX firing only on a different set of pixels. For example, in global mode, a global TX1 signal is firing a set 1 of pixels, a global TX2 signal is firing a set 2 of pixels . . . a global TXn signal is firing a set n of pixels.

Figure 27A:
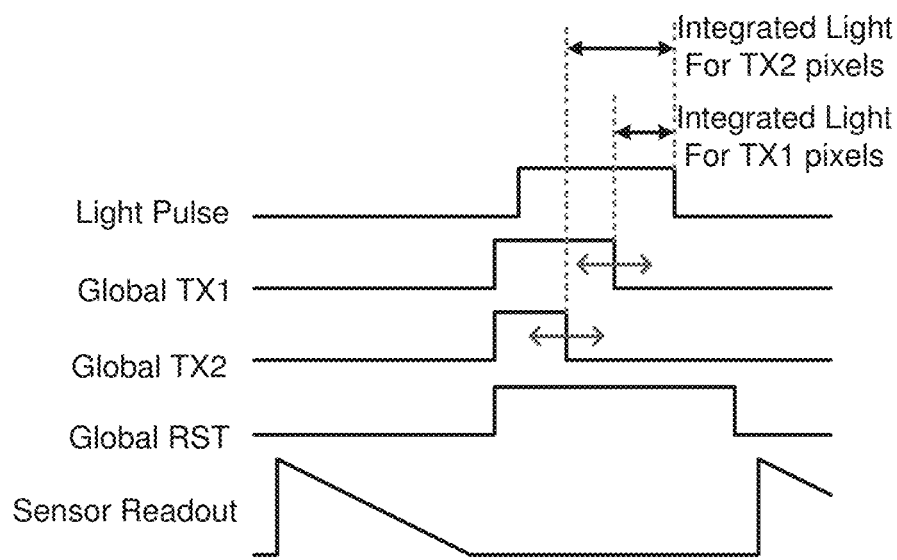
Figure 27B:
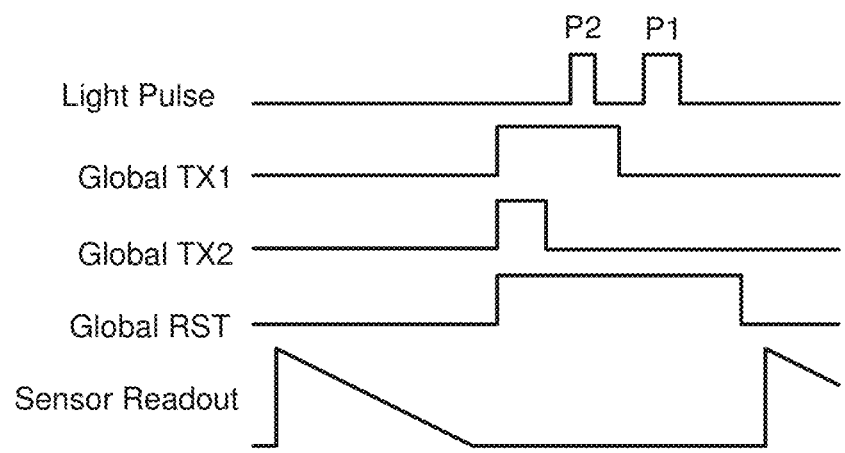

Based on FIG. 11, FIG. 27A shows a timing example for 2 different pixel sensitivities (dual pixel sensitivity) in the pixel array. In this case, global TX1 signal fires half of the pixels of the array and global TX2 fires the other half of the pixels. Because global TX1 and global TX2 have different "on" to "off" edge positions, integrated light is different between the TX1 pixels and the TX2 pixels. FIG. 27B shows a different embodiment of the timing for dual pixel sensitivity. In this case, the light pulse is modulated twice (pulse duration and/or amplitude). TX1 pixels integrate P1 pulse and TX2 pixels integrate P1+P2 pulses. Separating global TX signals can be done many ways. The following are examples:

i. Differentiating TX lines from each row; and
ii. Sending multiple TX lines per row, each addressing a different set of pixels.

In one implementation, a means of providing wide-dynamic range video is described, which exploits the color pulsing system described in this disclosure. The basis of this is to have multiple flavors of pixels, or pixels that may be tuned differently, within the same monochrome array that are able to integrate the incident light for different durations within the same frame. An example of the pixel arrangement in the array of such a sensor would be a uniform checkerboard pattern throughout, with two independently variable integration times. For such a case, it is possible to provide both red and blue information within the same frame. In fact, it is possible to do this at the same time as extending the dynamic range for the green frame, where it is most needed, since the two integration times can be adjusted on a frame by frame basis. The benefit is that the color motion artifacts are less of an issue if all the data is derived from two frames versus three. There is of course a subsequent loss of spatial resolution for the red and blue data, but that is of less consequence to the image quality compared with green, since the luminance component is dominated by green data.

An inherent property of the monochrome wide-dynamic range (WDR) array is that the pixels that have the long integration time must integrate a superset of the light seen by the short integration time pixels. For regular wide-dynamic range operation in the green frames, that is desirable. For the red and blue frames, it means that the pulsing must be controlled in conjunction with the exposure periods to, e.g., provide blue light from the start of the long exposure and switch to red at the point that the short exposure pixels are turned on (both pixel types have their charges transferred at the same time).

At the color fusion stage, the two flavors of pixels are separated into two buffers. The empty pixels are then filled in using, e.g., linear interpolation. At this point, one buffer contains a full image of blue data and the other red+blue. The blue buffer may be subtracted from the second buffer to give pure red data.

Figure 28A:
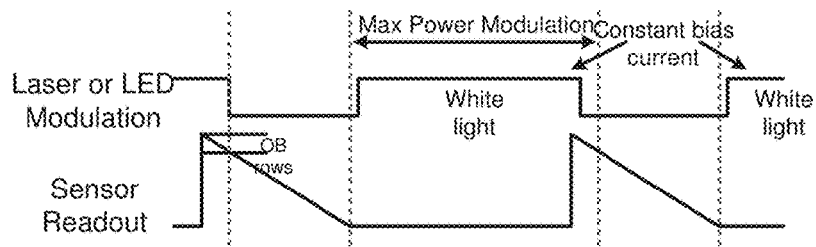
FIGS. 28A-28C illustrate the use of a white light emission that is pulsed and/or synced with a corresponding color sensor, according to embodiments of the disclosure.
Figure 28B:
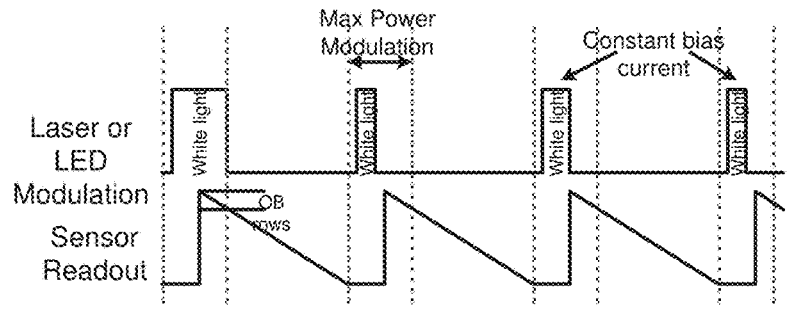
Figure 28C:
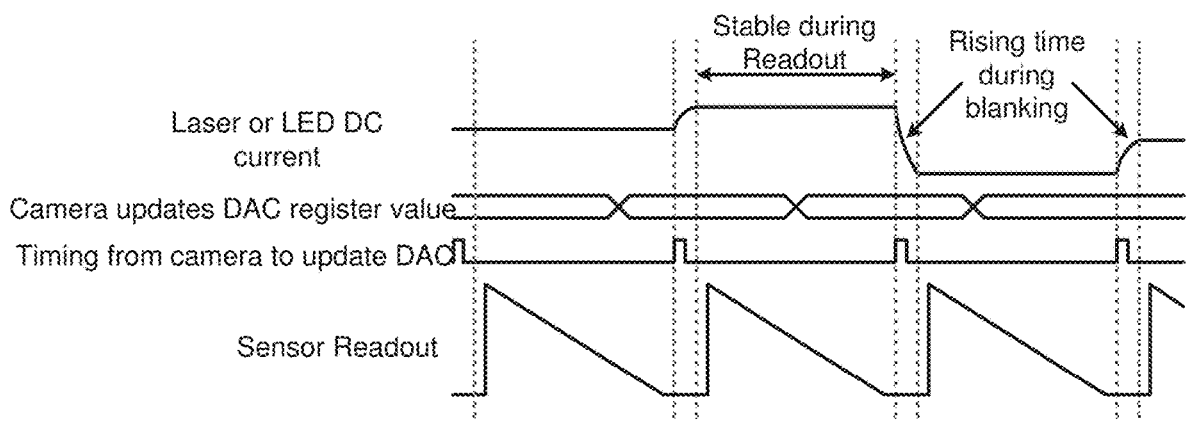

FIGS. 28A-28C illustrate the use of a white light emission that is pulsed and/or synced, or held constant, with a corresponding color sensor. As can be seen in FIG. 28A, a white light emitter may be configured to emit a beam of light during the blanking period of a corresponding sensor to provide a controlled light source in a controlled light environment. The light source may emit a beam at a constant magnitude and vary the duration of the pulse as seen in FIG. 28A, or may hold the pulse constant with varying the magnitude to achieve correctly exposed data as illustrated in FIG. 28B. Illustrated in FIG. 28C is a graphical representation of a constant light source that can be modulated with varying current that is controlled by and synced with a sensor.

In an embodiment, white light or multi-spectrum light may be emitted as a pulse, if desired, to provide data for use within the system (illustrated best in FIGS. 28A-28C). White light emissions in combination with partitions of the electromagnetic spectrum may be useful for emphasizing and de-emphasizing certain aspects within a scene. Such an embodiment might use a pulsing pattern of:

i. Green pulse;
ii. Red pulse;
iii. Blue pulse;

iv. Green pulse;
v. Red pulse;
vi. Blue pulse;
vii. White light (multi-spectrum) pulse;
viii. (Repeat)

Any system using an image sensor cycle that is at least two times faster than the white light cycle is intended to fall within the scope of the disclosure. It will be appreciated that any combination of partitions of the electromagnetic spectrum is contemplated herein, whether it be from the visible or non-visible spectrum of the full electromagnetic spectrum.

Figure 29A:
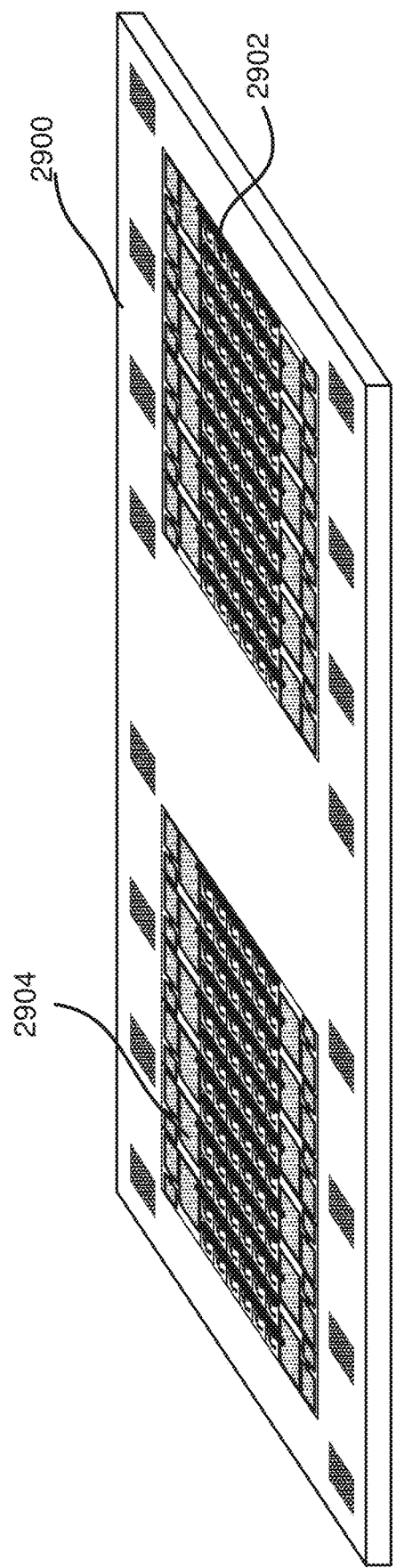
FIGS. 29A and 29B illustrate an implementation having a plurality of pixel arrays for producing a three-dimensional image, according to embodiments of the disclosure.
Figure 29B:
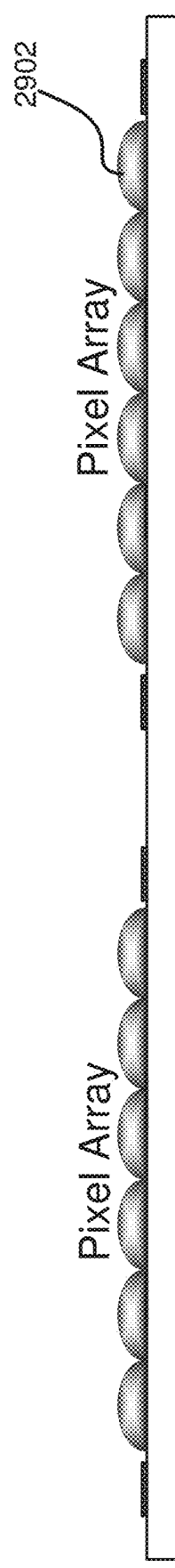

FIGS. 29A and 29B illustrate a perspective view and a side view, respectively, of an implementation of a monolithic sensor 2900 having a plurality of pixel arrays for producing a three-dimensional image in accordance with the teachings and principles of the disclosure. Such an implementation may be desirable for three-dimensional image capture, wherein the two pixel arrays 2902 and 2904 may be offset during use. In another implementation, a first pixel array 2902 and a second pixel array 2904 may be dedicated to receiving a predetermined range of wave lengths of electromagnetic radiation, wherein the first pixel array is dedicated to a different range of wave length electromagnetic radiation than the second pixel array.

Figure 30A:
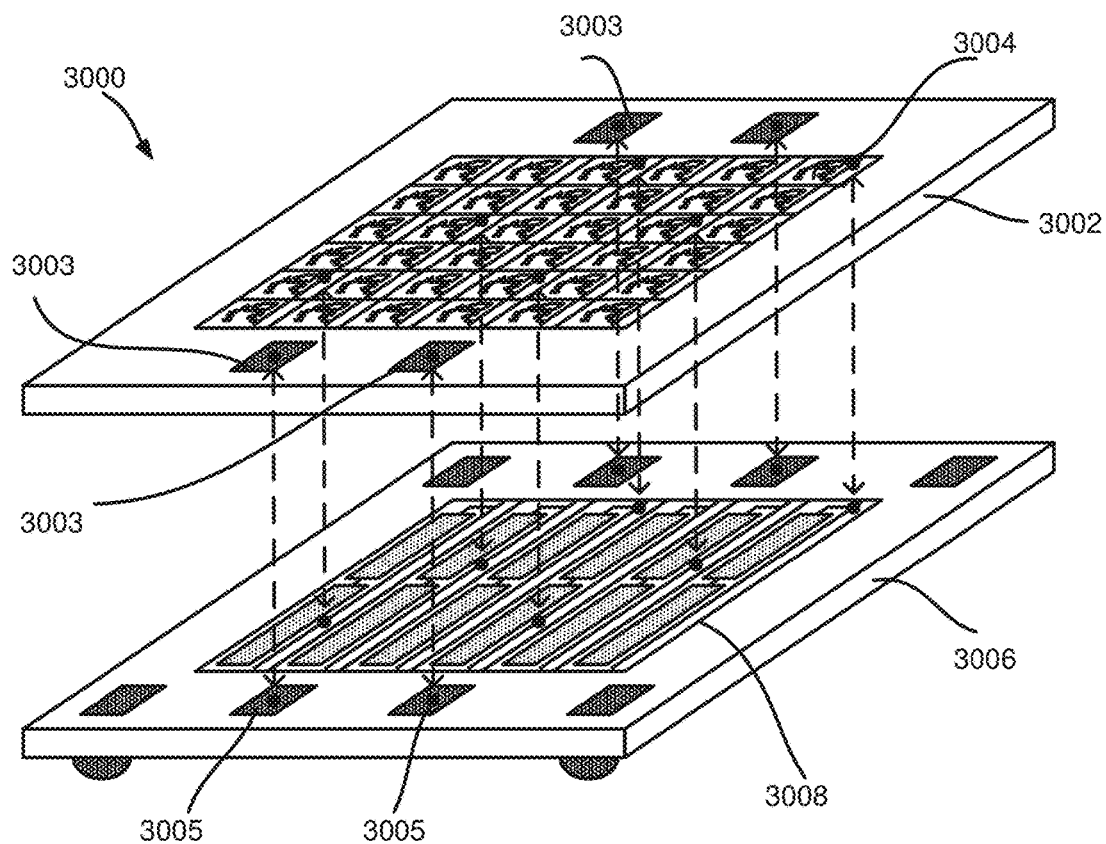
FIGS. 30A and 30B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 30B:
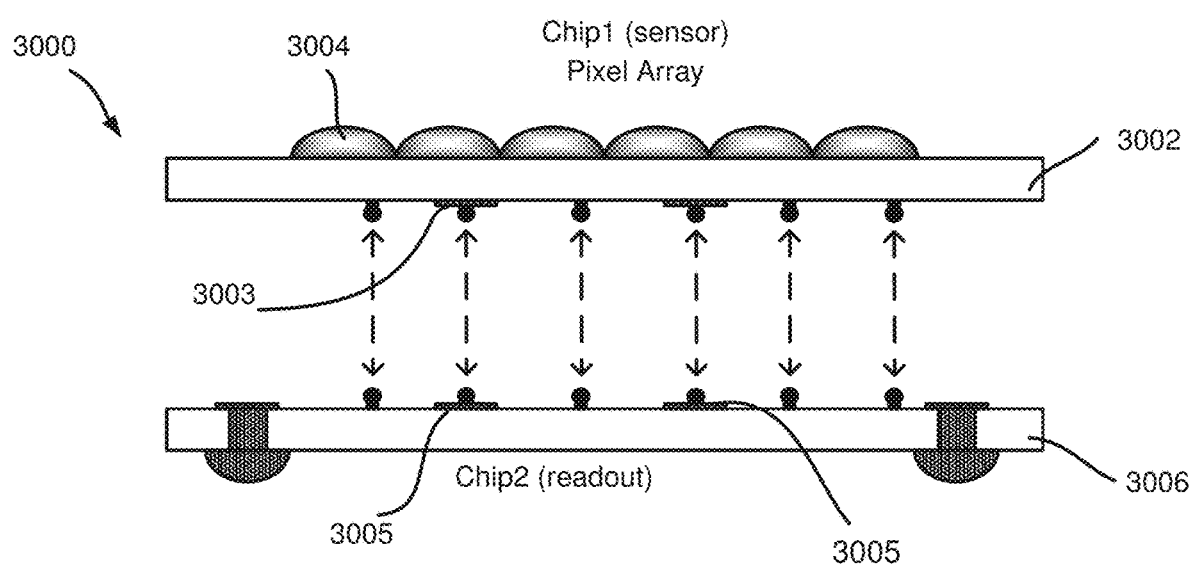

FIGS. 30A and 30B illustrate a perspective view and a side view, respectively, of an implementation of an imaging sensor 3000 built on a plurality of substrates. As illustrated, a plurality of pixel columns 3004 forming the pixel array are located on the first substrate 3002 and a plurality of circuit columns 3008 are located on a second substrate 3006. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 3002 of the two substrates/chips may be processed using an image CMOS process. The first substrate/chip 3002 may be comprised either of a pixel array exclusively or a pixel array surrounded by limited circuitry. The second or subsequent substrate/chip 3006 may be processed using any process and does not have to be from an image CMOS process. The second substrate/chip 3006 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 3002 may be stacked with the second or subsequent substrate/chip 3006 using any three-dimensional technique. The second substrate/chip 3006 may support most, or a majority, of the circuitry that would have otherwise been implemented in the first image CMOS chip 3002 (if implemented on a monolithic substrate/chip) as peripheral circuits and therefore have increased the overall system area while keeping the pixel array size constant and optimized to the fullest extent possible. The electrical connection between the two substrates/chips may be done through interconnects 3003 and 3005, which may be wire bonds, bump and/or TSV (Through Silicon Via).

Figure 31A:
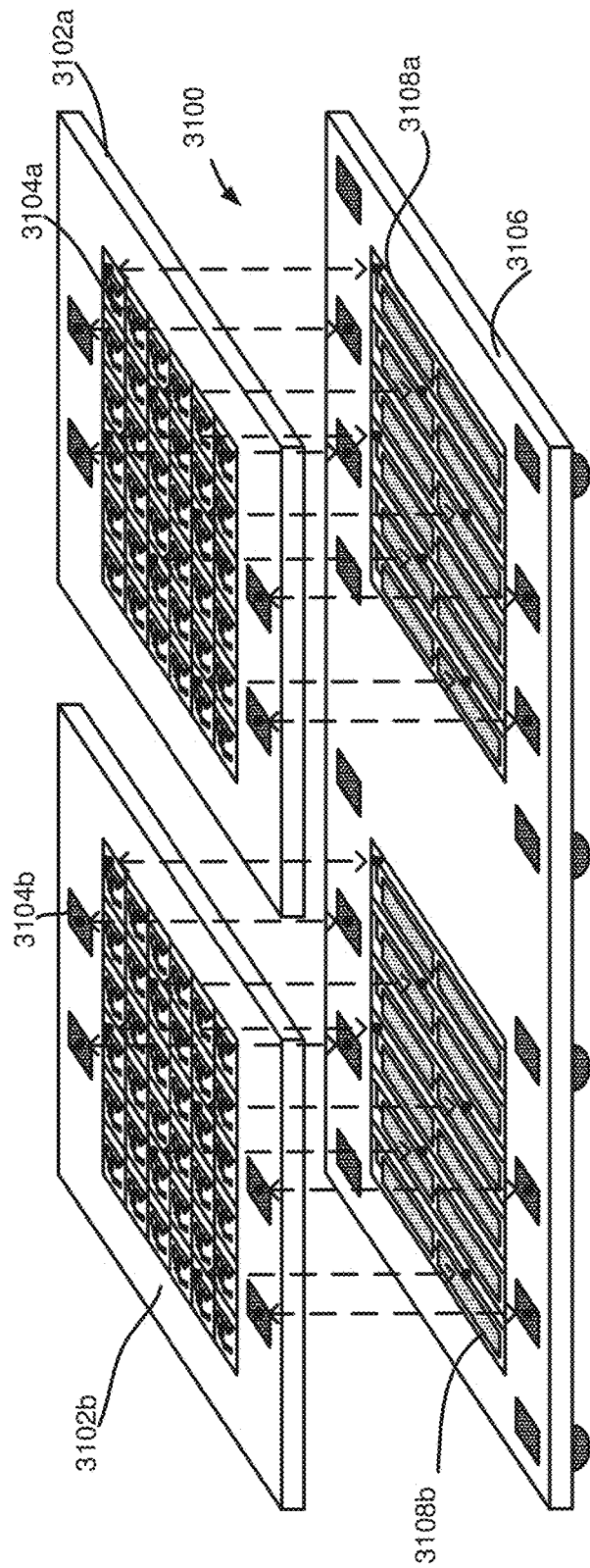
FIGS. 31A and 31B illustrate a perspective view and a side view, respectively, of an implementation of an imaging sensor having a plurality of pixel arrays for producing a three-dimensional image, wherein the plurality of pixel arrays and the image sensor are built on a plurality of substrates.
Figure 31B:
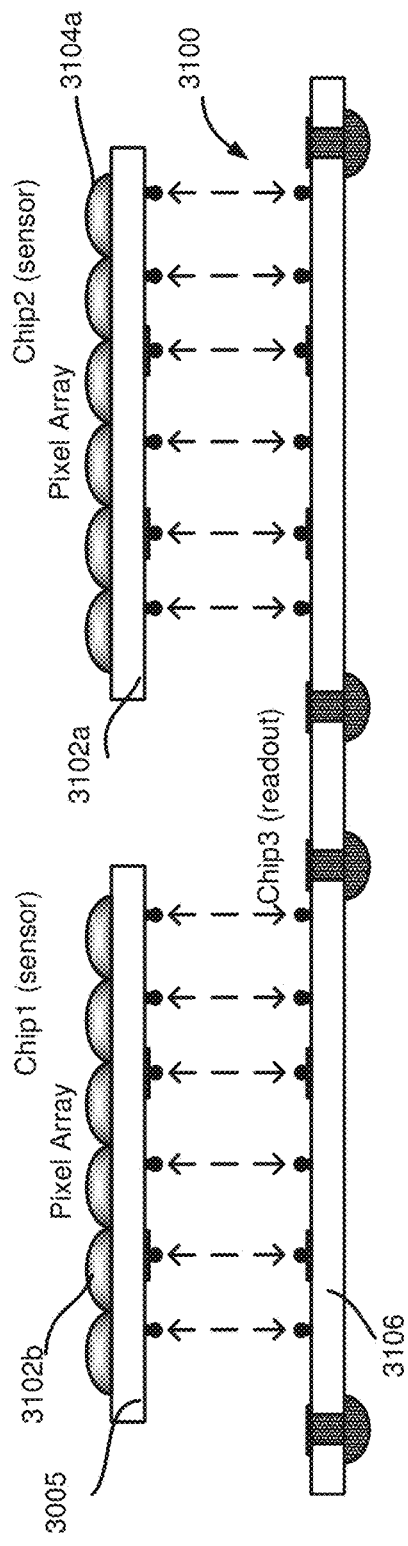

FIGS. 31A and 31B illustrate a perspective view and a side view, respectively, of an implementation of an imaging sensor 3100 having a plurality of pixel arrays for producing a three-dimensional image. The three-dimensional image sensor may be built on a plurality of substrates and may comprise the plurality of pixel arrays and other associated circuitry, wherein a plurality of pixel columns 3104a forming the first pixel array and a plurality of pixel columns 3104b forming a second pixel array are located on respective substrates 3102a and 3102b, respectively, and a plurality of circuit columns 3108a and 3108b are located on a separate substrate 3106. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single-use/disposable device platform a device is provided sterile to the operating room and used only once before being disposed of.

Figure 32:
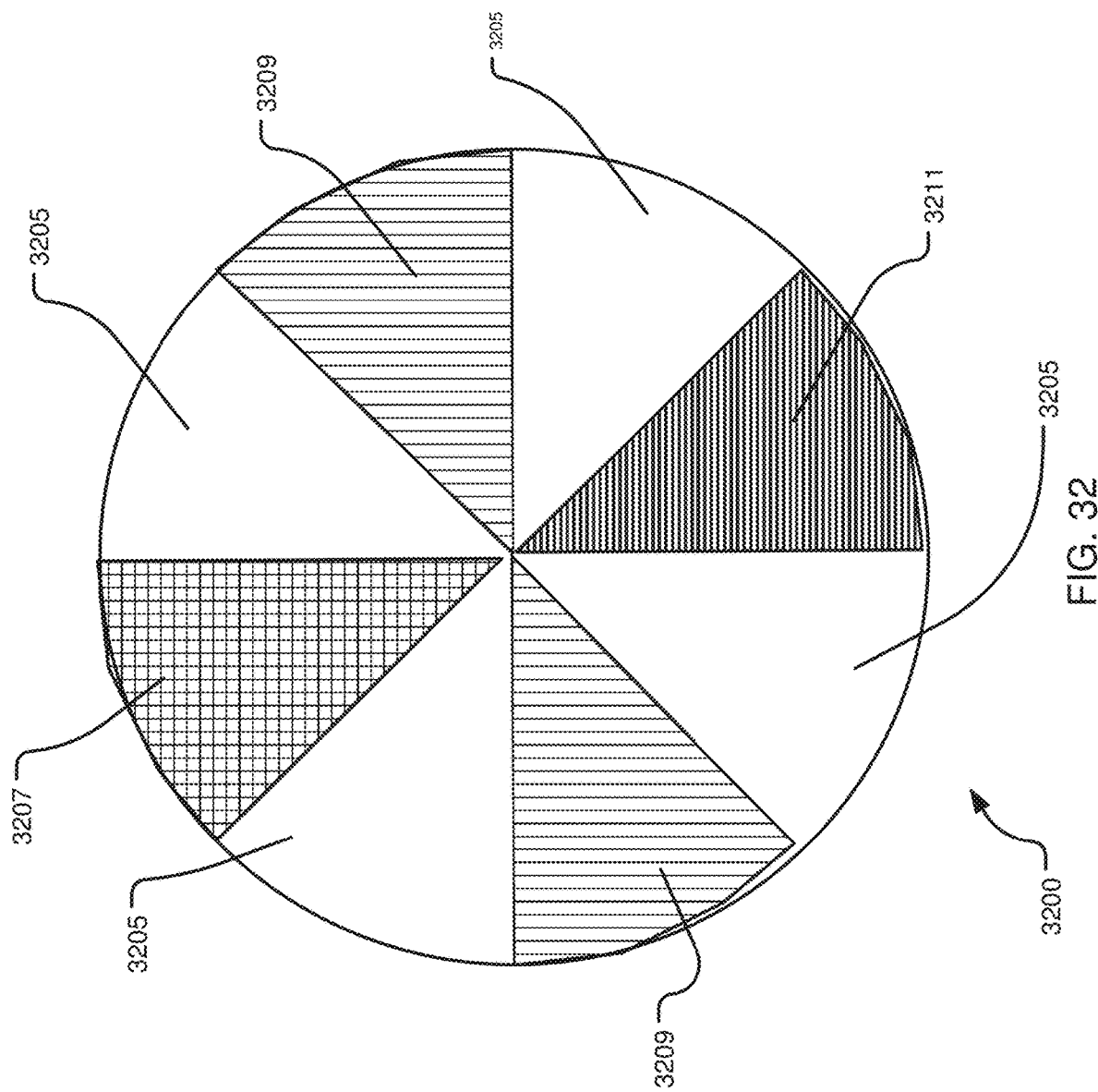
FIGS. 32-36 illustrate embodiments of emitters comprising various mechanical filter and shutter configurations, according to embodiments of the disclosure.

An embodiment of an emitter may employ the use of a mechanical shutter and filters to create pulsed color light. As illustrated in FIG. 32, an alternate method to produce pulsed color light, using a white light source and a mechanical color filter and shutter system 3200. The wheel could contain a pattern of translucent color filter windows and opaque sections for shuttering. The opaque sections would not allow light through and would create a period of darkness in which the sensor read-out could occur. The white light source could be based on any technology: laser, LED, xenon, halogen, metal halide, or other. The white light can be projected through a series of color filters 3207, 3209 and 3211 of the desired pattern of colored light pulses. One embodiment pattern could be Red filter 3207, Green filter 3209, Blue filter 3211, Green filter 3209. The filters and shutter system 3200 could be arranged on a wheel that spins at the required frequency to be in sync with the sensor such that knowledge of the arch length and rate of rotation of the mechanical color filters 3207, 3209 and 3211 and shutters 3205 system would provide timing information for the operation of a corresponding monochromatic image sensor.

Figure 33:
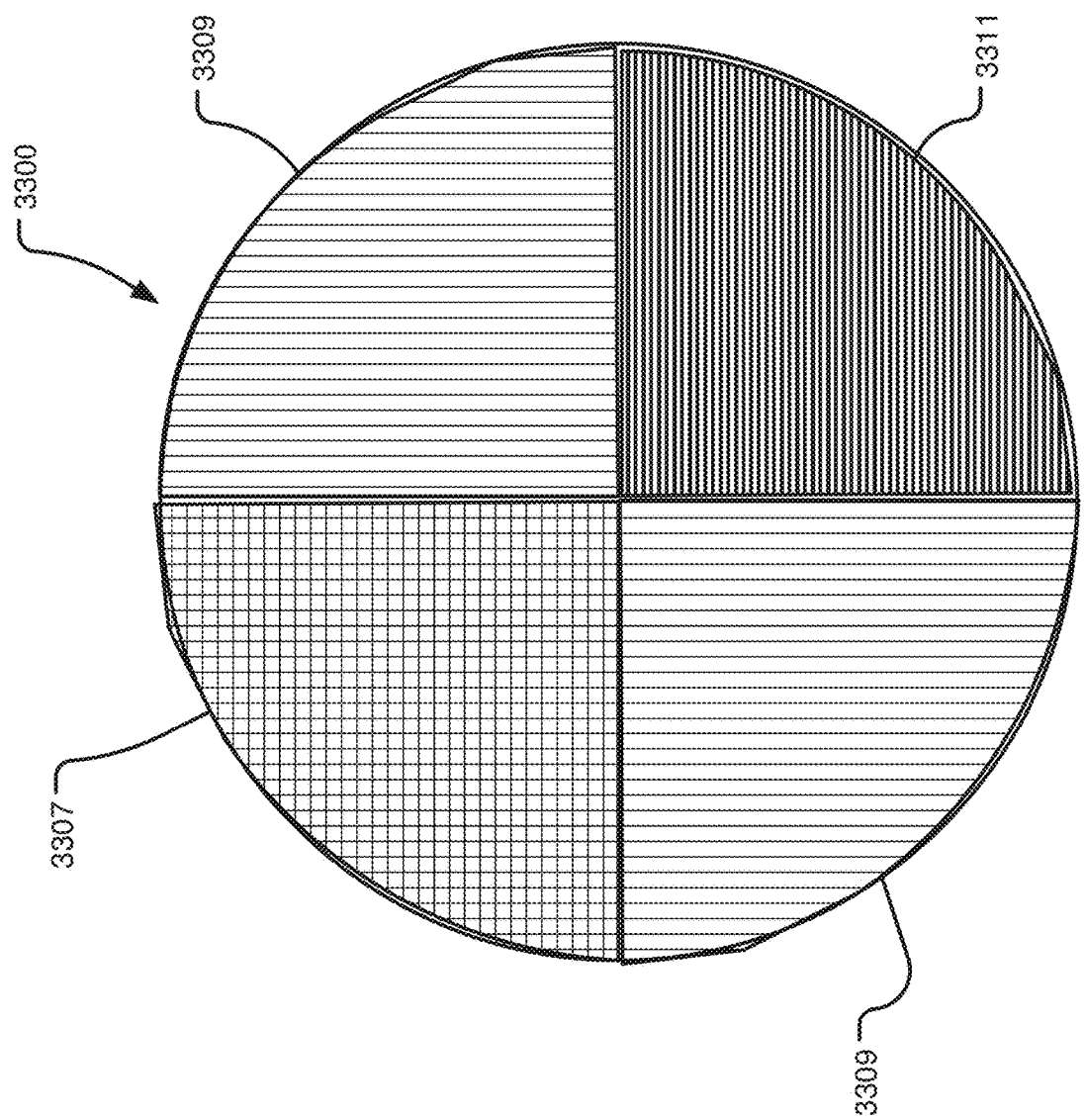

Illustrated in FIG. 33 an embodiment may comprise a pattern of only translucent color filters 3307, 3309 and 3311 on a filter wheel 3300. In the present configuration, a different shutter may be used. The shutter could be mechanical and could dynamically adjust the "pulse" duration by varying is size. Alternately the shutter could be electronic and incorporated into the sensor design. A motor spinning the filter wheel 3300 will need to communicate with or be controlled in conjunction with the sensor such that knowledge of the arch length and rate of rotation of the mechanical color filters 3307, 3309 and 3311 system would provide timing information for the operation of the corresponding monochromatic image sensor. The control system will need to know the proper color filter for each frame captured by the sensor so that the full-color image can be reconstructed properly in the ISP. A color pattern of RGBG is shown, but other colors and/or patterns could be used if advantageous. The relative size of the color sections is shown as equal but could be adjusted if advantageous. The mechanical structure of the filter is shown as a circle moving rotationally, but could be rectangular with a linear movement, or a different shape with a different movement pattern.

Figure 34:
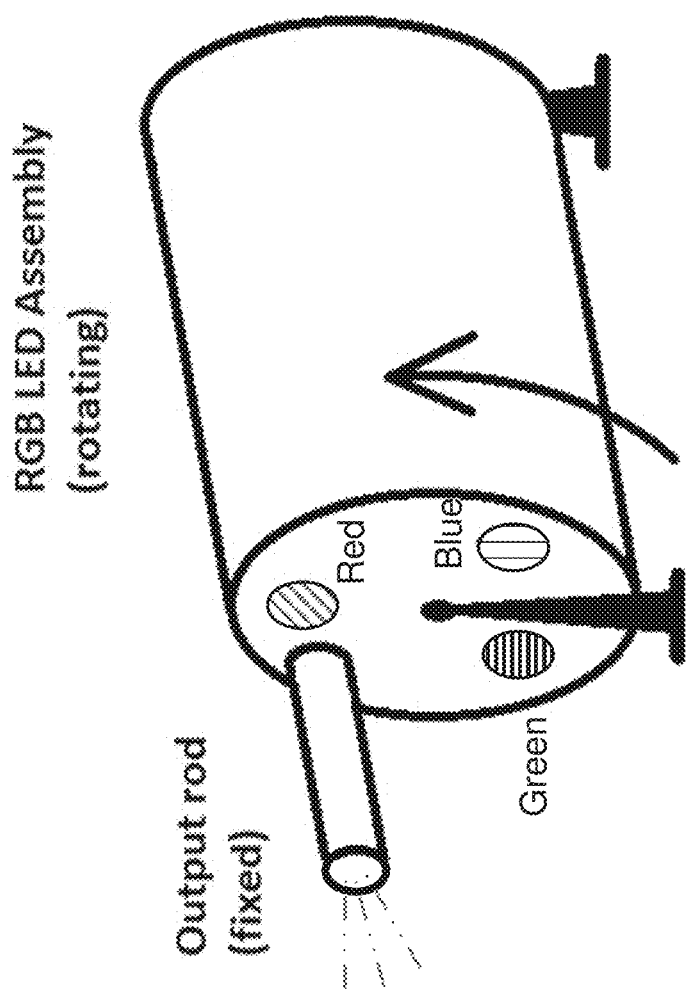

As illustrated FIG. 34, an embodiment for pulsing color light may consist of a mechanical wheel or barrel that holds the electronics and heat sinks for Red, Green, Blue or White LEDS. The LEDs would be spaced at the distance that would be related to the rate of spin or twist of the barrel or wheel to allow for timing of light pulsing consistent with other embodiments in the patent. The wheel or barrel would be spun using an electrical motor and a mechanical bracket attaching the wheel or barrel to the electrical motor. The motor would be controlled using a microcontroller, FPGA, DSP, or other programmable device that would contain a control algorithm for proper timing as described in the patent. There would be a mechanical opening on one side that would be optically coupled to a fiber optic to transport the fiber to the end of the scopes with the methods described in the patent. This coupling could also have a mechanical aperture that could open and close to control the amount of light allowed down the fiber optic cable. This would be a mechanical shutter device alternatively one could use the electronic shutter that is designed into a CMOS or CCD type sensor. This device would be difficult to control and calibrate in production but is another way one could get pulsed light into our system.

Figure 35:
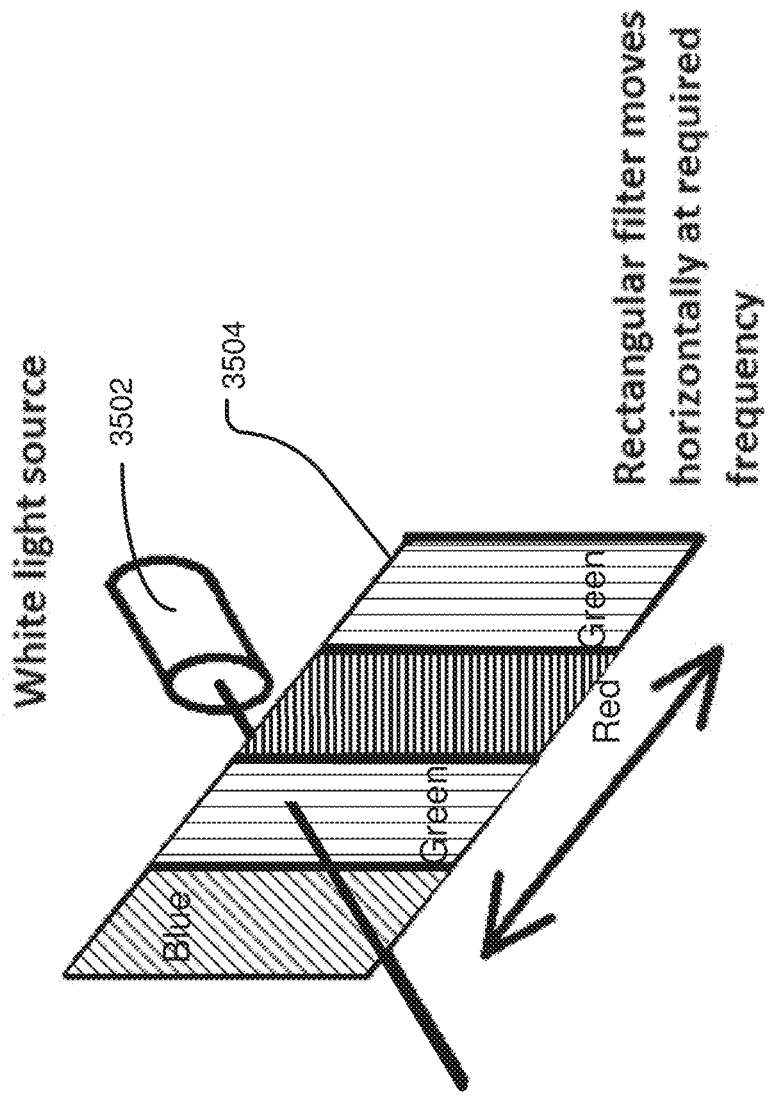

Illustrated in FIG. 35 is an embodiment of an emitter 3502 comprising a linear filter 3504 and shutter mechanism to provide pulsed electromagnetic radiation. The linear filter 3504 and shutter mechanism moves horizontally at a required frequency to filter the appropriate wavelengths of light.

Figure 36:
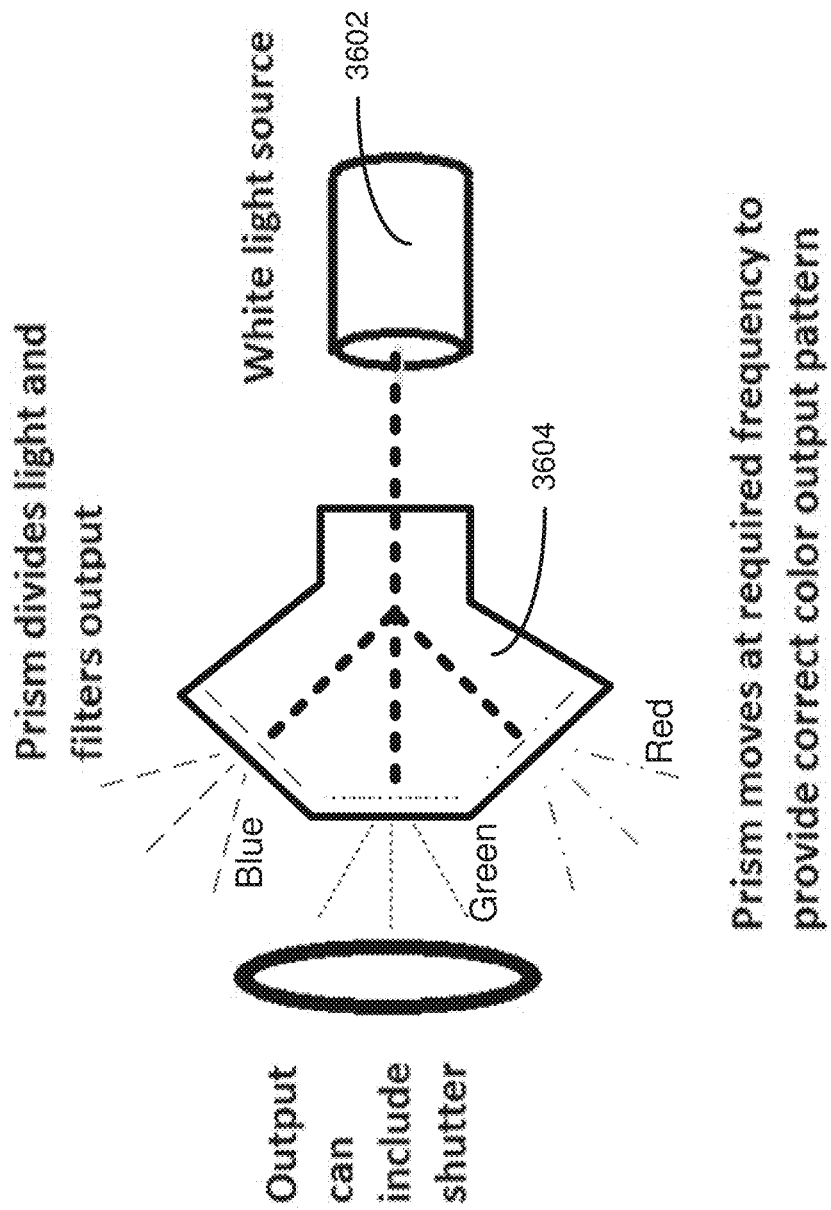

Illustrating in FIG. 36 is an embodiment of an emitter 3602 comprising a prism filter 3604 and shutter mechanism to provide pulsed electromagnetic radiation. The prism filter 3604 filters light and delivers an output can that may include a shutter. The prism filter 3604 moves at a required frequency to provide a correct color output pattern.

Additionally, the teachings and principles of the disclosure may include any and all wavelengths of electromagnetic energy, including the visible and non-visible spectrums, such as infrared (IR), ultraviolet (UV), and X-ray.

Figure 37:
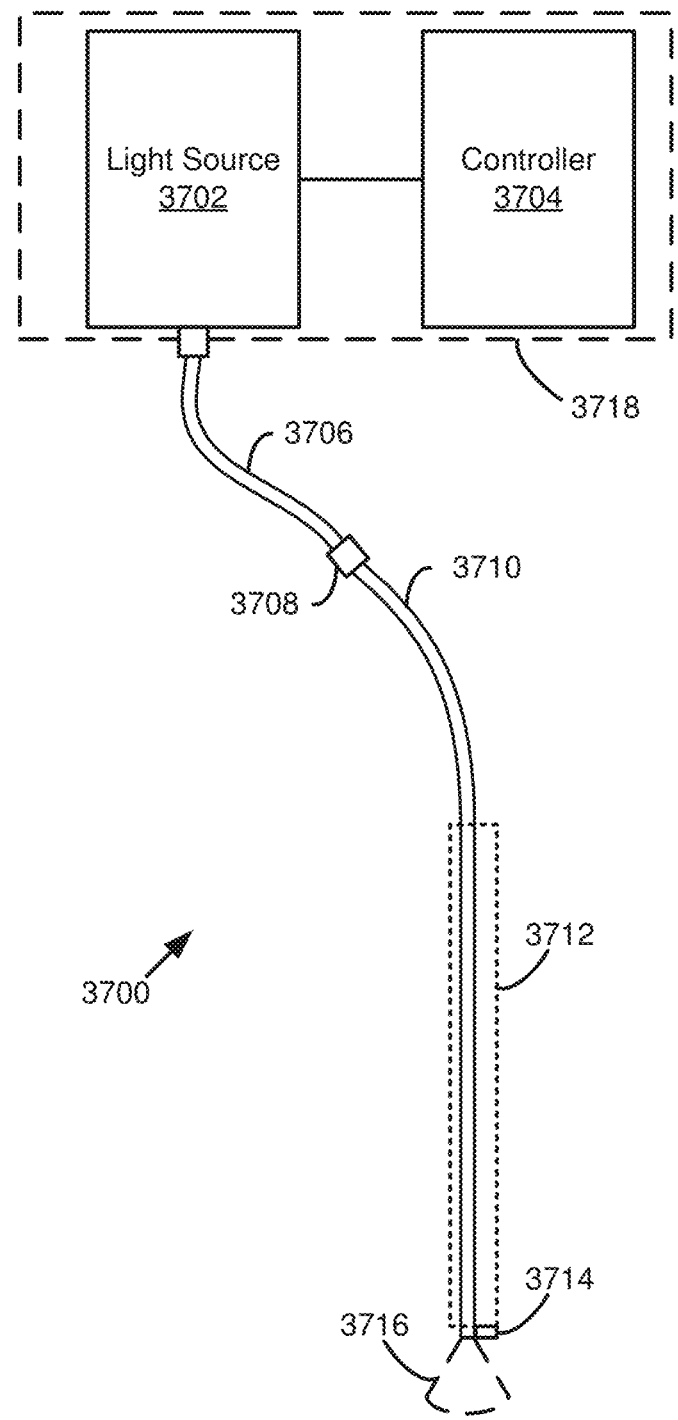
FIG. 37 is a schematic diagram illustrating a system for providing illumination to a light deficient environment, according to one embodiment.

FIG. 37 is a schematic diagram illustrating a system 3700 for providing illumination to a light deficient environment, such as for endoscopic imaging. The system 3700 may be used in combination with any of the systems, methods, or devices disclosed herein. The system 3700 includes a light source 3702, a controller 3704, a jumper waveguide 3706, a waveguide connector 3708, a lumen waveguide 3710, a lumen 3712, and an image sensor 3714 with accompanying optical components (such as a lens). The light source 3702 generates light that travels through the jumper waveguide 3706 and the lumen waveguide 3710 to illuminate a scene at a distal end of the lumen 3712. The light source 3700 may be used to emit any wavelength of electromagnetic energy including visible wavelengths, infrared, ultraviolet, or other wavelengths. The lumen 3712 may be inserted into a patient's body for imaging, such as during a procedure or examination. The light is output as illustrated by dashed lines 3716. A scene illuminated by the light may be captured using the image sensor 3714 and displayed for a doctor or some other medical personnel. The controller 3704 may provide control signals to the light source 3702 to control when illumination is provided to a scene. In one embodiment, the light source 3702 and controller 3704 are located within a camera control unit (CCU) or external console to which an endoscope is connected. If the image sensor 3714 includes a CMOS sensor, light may be periodically provided to the scene in a series of illumination pulses between readout periods of the image sensor 3714 during what is known as a blanking period. Thus, the light may be pulsed in a controlled manner to avoid overlapping into readout periods of the image pixels in a pixel array of the image sensor 3714.

In one embodiment, the lumen waveguide 3710 includes a one or a plurality of optical fibers. The optical fibers may be made of a low-cost material, such as plastic to allow for disposal of the lumen waveguide 3710 and/or other portions of an endoscope. In one embodiment, a single glass fiber having a diameter of 500 microns may be used. The jumper waveguide 3706 may be permanently attached to the light source 3702. For example, a jumper waveguide 3706 may receive light from an emitter within the light source 3702 and provide that light to the lumen waveguide 3710 at the location of the connector 3708. In one embodiment, the jumper waveguide 106 may include one or more glass fibers. The jumper waveguide may include any other type of waveguide for guiding light to the lumen waveguide 3710. The connector 3708 may selectively couple the jumper waveguide 3706 to the lumen waveguide 3710 and allow light within the jumper waveguide 3706 to pass to the lumen waveguide 3710. In one embodiment, the lumen waveguide 3710 may be directly coupled to a light source without any intervening jumper waveguide 3706.

Figure 38:
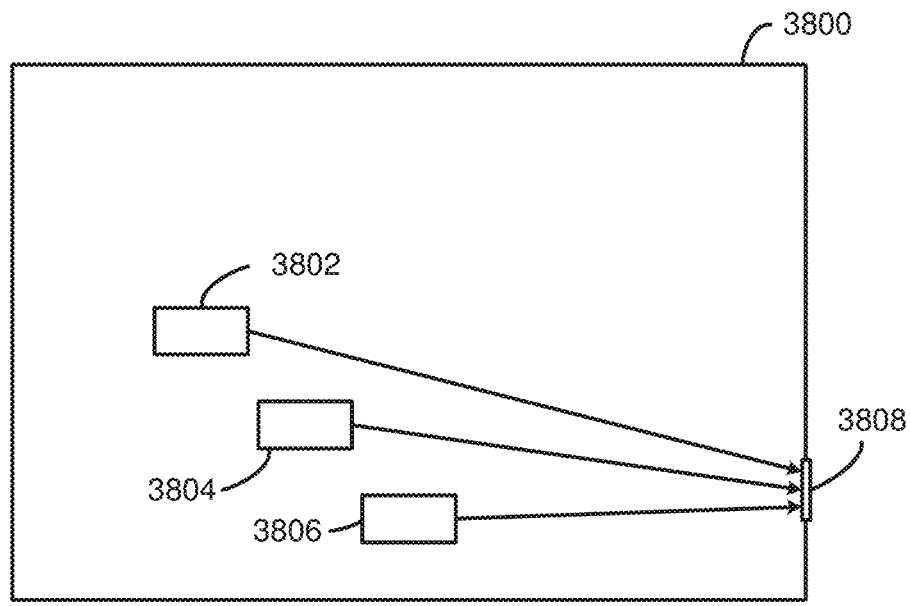
FIG. 38 is a schematic block diagram illustrating a light source having a plurality of emitters, according to one embodiment.
Figure 39:
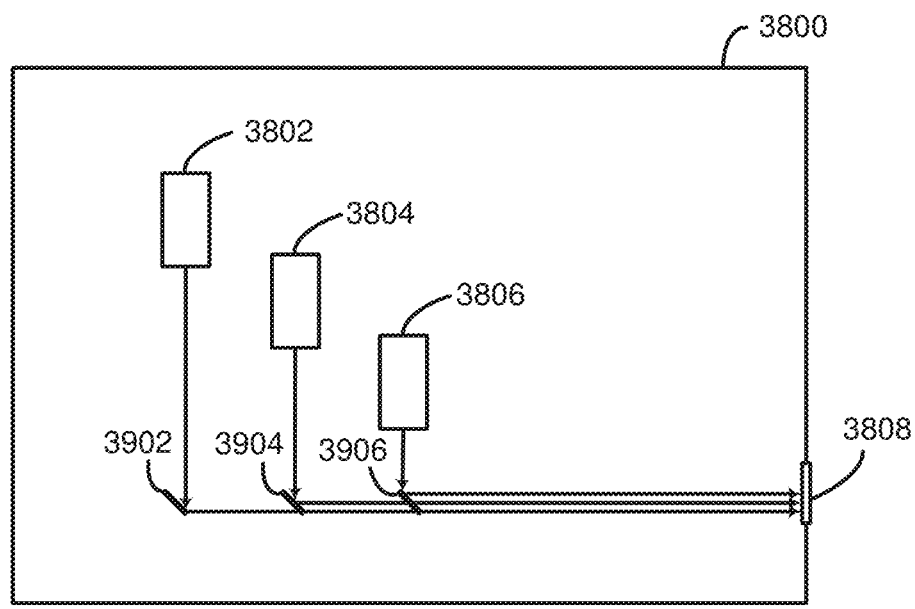
FIG. 39 is a schematic block diagram illustrating a light source having a plurality of emitters, according to another embodiment.
Figure 40:
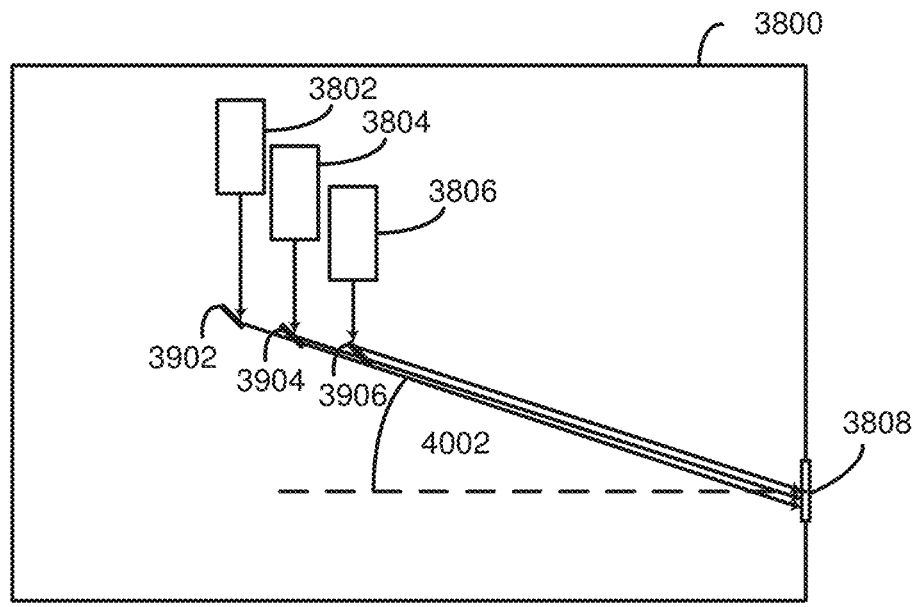
FIG. 40 is a schematic block diagram illustrating a light source having a plurality of emitters, according to yet another embodiment.

FIGS. 38-40 are schematic block diagrams illustrating a light source 3800 having a plurality of emitters. With regard to FIG. 38, the emitters include a first emitter 3802, a second emitter 3804, and a third emitter 3806. Additional emitters may be included, as discussed further below. The emitters 3802, 3804, and 3806 may include one or more laser emitters that emit light having different wavelengths. For example, the first emitter 3802 may emit a wavelength that is consistent with a blue laser, the second emitter 3804 may emit a wavelength that is consistent with a green laser, and the third emitter 3806 may emit a wavelength that is consistent with a red laser. For example, the first emitter 3802 may include one or more blue lasers, the second emitter 3804 may include one or more green lasers, and the third emitter 3806 may include one or more red lasers. The emitters 3802, 3804, 3806 emit laser beams toward a collection region 3808, which may be the location of a waveguide, lens, or other optical component for collecting and/or providing light to a waveguide, such as the jumper waveguide 3706 or lumen waveguide 3710 of FIG. 37.

In an implementation where a patient has been administered a reagent or dye to aid in the identification of certain tissues, structures, chemical reactions, biological processes, and so forth, the emitters 3802, 3804, and 3806 may emit wavelength(s) for fluorescing the reagents or dyes. Such wavelength(s) may be determined based on the reagents or dyes administered to the patient. In such an embodiment, the emitters may need to be highly precise for emitting desired wavelength(s) to fluoresce or activate certain reagents or dyes.

In the embodiment of FIG. 38, the emitters 3802, 3804, 3806 each deliver laser light to the collection region 3808 at different angles. The variation in angle can lead to variations where electromagnetic energy is located in an output waveguide. For example, if the light passes immediately into a fiber bundle (glass or plastic) at the collection region 3808, the varying angles may cause different amounts of light to enter different fibers. For example, the angle may result in intensity variations across the collection region 3808. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 3802, 3804, 3806 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 3808 is represented as a physical component in FIG. 38, the collection region 3808 may simply be a region where light from the emitters 3802, 3804, and 3806 is delivered. In some cases, the collection region 3808 may include an optical component such as a diffuser, mixing rod, lens, or any other intervening optical component between the emitters 3802, 3804, 3806 and an output waveguide.

FIG. 39 illustrates an embodiment of a light source 3800 with emitters 3802, 3804, 3806 that provide light to the collection region 3808 at the same or substantially same angle. The light is provided at an angle substantially perpendicular to the collection region 3808. The light source 3800 includes a plurality of dichroic mirrors including a first dichroic mirror 3902, a second dichroic mirror 3904, and a third dichroic mirror 3906. The dichroic mirrors 3902, 3904, 3906 include mirrors that reflect a first wavelength of light but transmit (or are transparent to) a second wavelength of light. For example, the third dichroic mirror 3906 may reflect blue laser light provided by the third emitter, while being transparent to the red and green light provided by the first emitter 3802 and the second emitter 3804, respectively. The second dichroic mirror 3904 may be transparent to red light from the first emitter 3802, but reflective to green light from the second emitter 3804. If other colors or wavelengths are included dichroic mirrors may be selected to reflect light corresponding to at least one emitter and be transparent to other emitters. For example, the third dichroic mirror 3906 reflect the light form the third emitter 3806 but is to emitters "behind" it, such as the first emitter 3802 and the second emitter 3804. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 3808 at a substantially same angle.

Because the dichroic mirrors allow other wavelengths to transmit or pass through, each of the wavelengths may arrive at the collection region 3808 from a same angle and/or with the same center or focal point. Providing light from the same angle and/or same focal/center point can significantly improve reception and color mixing at the collection region 3808. For example, a specific fiber may receive the different colors in the same proportions they were transmitted/reflected by the emitters 3802, 3804, 3806 and mirrors 3902, 3904, 3906. Light mixing may be significantly improved at the collection region compared to the embodiment of FIG. 38. In one embodiment, any optical components discussed herein may be used at the collection region 3808 to collect light prior to providing it to a fiber or fiber bundle.

FIG. 40 illustrates an embodiment of a light source 3800 with emitters 3802, 3804, 3806 that also provide light to the collection region 3808 at the same or substantially same angle. However, the light incident on the collection region 3808 is offset from being perpendicular. Angle 4002 indicates the angle offset from perpendicular. In one embodiment, the laser emitters 3802, 3804, 3806 may have cross sectional intensity profiles that are Gaussian. As discussed previously, improved distribution of light energy between fibers may be accomplished by creating a more flat or top-hat shaped intensity profile. In one embodiment, as the angle 4002 is increased, the intensity across the collection region 3808 approaches a top hat profile. For example, a top-hat profile may be approximated even with a non-flat output beam by increasing the angle 4002 until the profile is sufficiently flat.

The top hat profile may also be accomplished using one or more lenses, diffusers, mixing rods, or any other intervening optical component between the emitters 3802, 3804, 3806 and an output waveguide, fiber, or fiber optic bundle.

Figure 41:
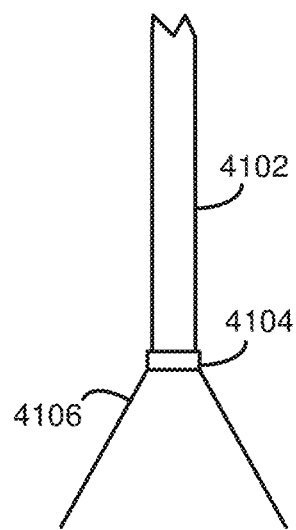
FIG. 41 is a schematic diagram illustrating a single optical fiber outputting via a diffuser at an output to illuminate a scene, according to one embodiment.

FIG. 41 is a schematic diagram illustrating a single optical fiber 4102 outputting via a diffuser 4104 at an output. In one embodiment, the optical fiber 4102 may have a diameter of 500 microns and have a numerical aperture of 0.65 and emit a light cone 4106 of about 70 or 80 degrees without a diffuser 4104. With the diffuser 4104, the light cone 4106 may have an angle of about 110 or 120 degrees. The light cone 4106 may be a majority of where all light goes and is evenly distributed. The diffuser 4104 may allow for more even distribution of electromagnetic energy of a scene observed by an image sensor.

In one embodiment, the lumen waveguide 4102 may include a single plastic or glass optical fiber of about 500 microns. The plastic fiber may be low cost, but the width may allow the fiber to carry a sufficient amount of light to a scene, with coupling, diffuser, or other losses. For example, smaller fibers may not be able to carry as much light or power as a larger fiber. The lumen waveguide 3710 may include a single or a plurality of optical fibers. The lumen waveguide 3702 may receive light directly from the light source or via a jumper waveguide (e.g., see the jumper waveguide 3706 of FIG. 37). A diffuser may be used to broaden the light output 3706 for a desired field of view of the image sensor 3714 or other optical components.

Although three emitters are shown in FIGS. 38-40, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums).

In one embodiment, a light source with a plurality of emitters may be used for multispectral or hyperspectral imaging in a light deficient environment. For example, different chemicals, materials, or tissue may have different responses to different colors or wavelengths of electromagnetic energy. Some tissues have their own spectral signature (how they respond or vary in reflecting wavelengths of electromagnetic radiation). In one embodiment, a specific type of tissues may be detected based on how it responds to a specific wavelength or a specific combination of wavelengths. For example, blood vessel tissues may absorb and reflect different wavelengths or spectrums of electromagnetic energy in a unique way to distinguish it from muscle, fat, bone, nerve, ureter, or other tissues or materials in the body. Furthermore, specific types of muscle or other types of tissue may be distinguished based on their spectral response. Disease states of tissue may also be determined based on spectral information. See U.S. Pat. No. 8,289,503. See also U.S. Pat. No. 8,158,957.

Figure 42:
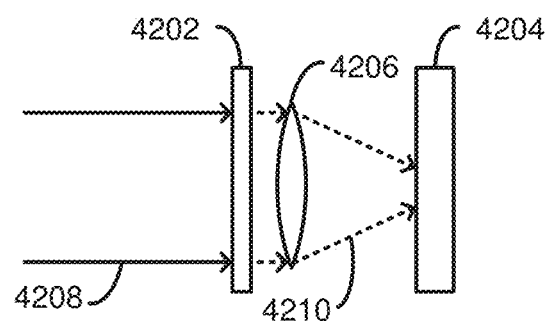
FIG. 42 is a block diagram illustrating generating a filtered image using a filter, according to one embodiment.

In one embodiment, fluorescent image data, and/or multispectral or hyperspectral image data may be obtained using one or more filters to filter out all light or electromagnetic energy, except that in the desired wavelength or spectrum. FIG. 42 is a block diagram illustrating a filter 4202 for filtering out unwanted wavelengths before light 4208 (or other electromagnetic radiation) encounters an imaging sensor 4204 or other imaging medium (e.g., film). In one embodiment, white light 4208 passes through the filter 4202 and filtered light 4210 passes through a lens 4206 to be focused onto the imaging sensor 4204 for image capture and readout. The filter may be located anywhere in the system or may be an attribute of the lens 4206 or image sensor 4204.

In a light deficient environment, the light 4208 may include white light emitted by an emitter in the light deficient environment. The filter 4202 may be selected for the desired examination. For example, if it is desired to detect or highlight a specific tissue, the filter 4202 may be selected to allow wavelengths corresponding to the spectral response of the specific tissue or the fluorescence emission of a specific reagent to pass through. The image sensor 4204, which may include a monochromatic image sensor, may generate an image. Pixels of the captured image that exceed a threshold or fall below a threshold may then be characterized as corresponding to the specific tissue. This data may then be used to generate an image that indicates the location of the specific tissue.

In another embodiment, a fluorescing dye or reagent may be used for imaging specific tissue types, pathways, or the like in a body. For example, a fluorescing dye may be administered to a patient and then an image of the dye may be captured. In one embodiment, fluorescing of the dye may be triggered using a specific wavelength of electromagnetic energy. For example, the dye may only fluoresce when the electromagnetic energy is present.

However, both filters and fluorescing dyes significantly constrain examination. For example, if a filter is used, the desired spectral response that can be detected, and thus the material or tissue that can be detected, is limited by the available filters. Furthermore, the filters may need to be swapped or replaced. With regard to dyes, the dye must be administered before imaging and there may be conflicts between administering different dyes for different purposes during the same examination. Thus, examinations using filters and dyes can take a long time and may require many different examinations to get the desired information.

In one embodiment, multispectral or hyper spectral imaging in a light deficient environment may be achieved using a monochrome image sensor and emitters that emit a plurality of different wavelengths or spectrums of electromagnetic energy. In one embodiment, a light source or other electromagnetic source (such as a light source 3800 in any of FIGS. 38-40) may include a plurality of emitters to cover desired spectrums.

Figure 43:
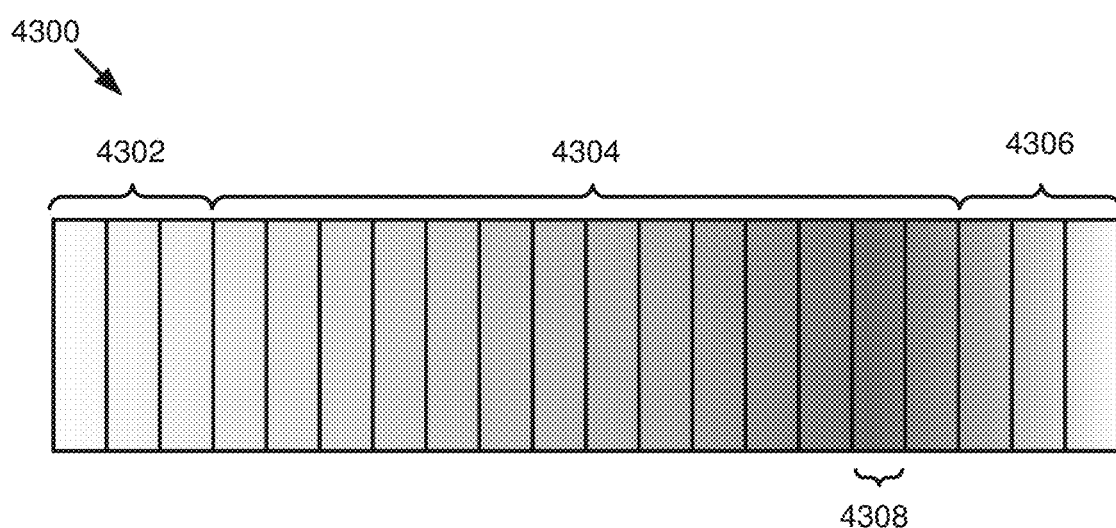
FIG. 43 illustrates a portion of the electromagnetic spectrum divided into a plurality of different sub-spectrums which may be emitted by emitters of a light source, according to one embodiment.

FIG. 43 illustrates a portion of the electromagnetic spectrum 4300 divided into twenty different sub-spectrums. The number of sub-spectrums is illustrative only. In at least one embodiment, the spectrum 4300 may be divided into hundreds of sub-spectrums, each with a small waveband. The spectrum may extend from the infrared spectrum 4302, through the visible spectrum 4304, and into the ultraviolet spectrum 4306. The sub-spectrums each have a waveband 4308 that covers a portion of the spectrum 4300. Each waveband may be defined by an upper wavelength and a lower wavelength.

In one embodiment, at least one emitter (such as a laser emitter) may be included in a light source (such as the light sources 3702, 3800 in FIGS. 37-40) for each sub-spectrum to provide complete and contiguous coverage of the whole spectrum 4300. For example, a light source for providing coverage of the illustrated sub-spectrums may include at least 20 different emitters, at least one for each sub-spectrum. In one embodiment, each emitter may cover a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral imaging. Because the wavelengths come from emitters which can be selectively activated, extreme flexibility in determining spectral responses of a material during an examination can be achieved. Thus, much more information about spectral response may be achieved in less time and within a single examination which would have required multiple examinations, delays because of the administration of dyes or stains, or the like. In one embodiment, a system may capture hyperspectral image data and process that data to identify what type of tissue exists at each pixel.

Figure 44:
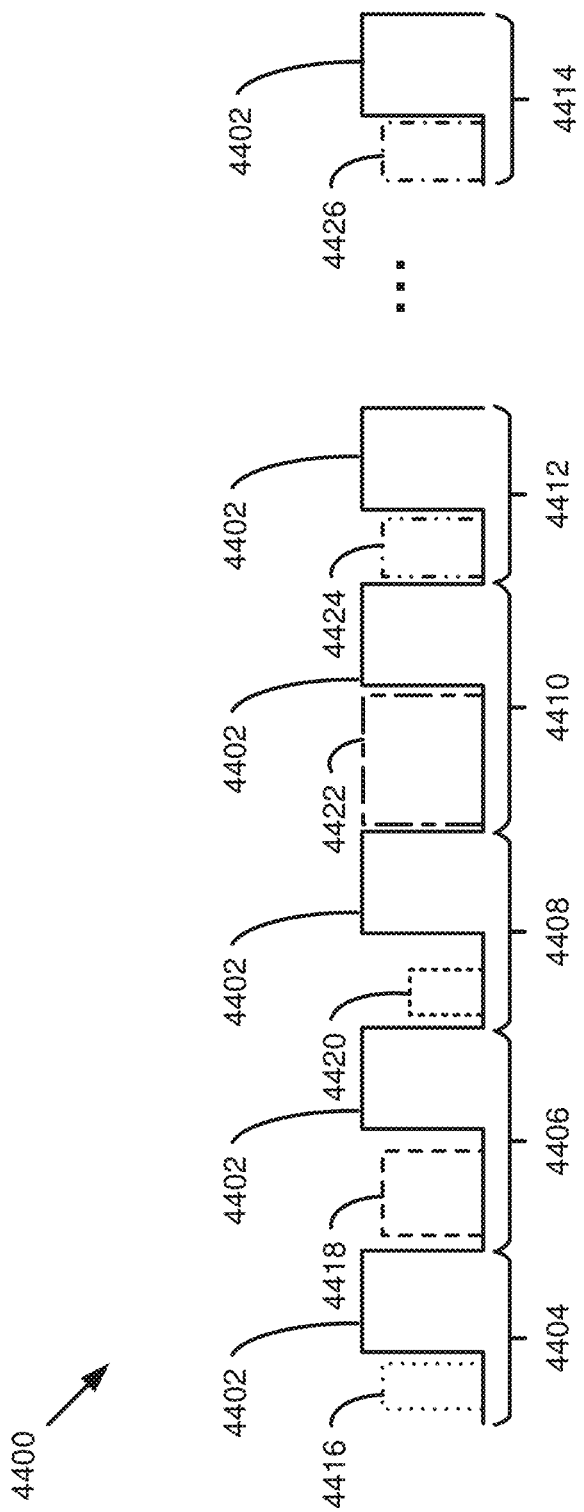
FIG. 44 is a schematic diagram illustrating a timing diagram for emission and readout for generating a multispectral or hyperspectral image, according to one embodiment.

FIG. 44 is a schematic diagram illustrating a timing diagram 4400 for emission and readout for generating a multispectral or hyperspectral image, according to one embodiment. The solid line represents readout (peaks 4402) and blanking periods (valleys) for capturing a series of frames 4404-4414. The series of frames 4404-4414 may include a repeating series of frames which may be used for generating hyperspectral data for a video feed. The series of frames include a first frame 404, a second frame 4406, a third frame 4408, a fourth frame 4410, a fifth frame 4412, and an Nth frame 4426.

In one embodiment, each frame is generated based on at least one pulse of electromagnetic energy. The pulse of electromagnetic energy is reflected and detected by an image sensor and then read out in a subsequent readout (4402). Thus, each blanking period and readout results in an image frame for a specific spectrum of electromagnetic energy. For example, the first frame 404 may be generated based on a spectrum of a first one or more pulses 4416, a second frame 4406 may be generated based on a spectrum of a second one or more pulses 4418, a third frame 4408 may be generated based on a spectrum of a third one or more pulses 4420, a fourth frame 4410 may be generated based on a spectrum of a fourth one or more pulses 4422, a fifth frame 4412 may be generated based on a spectrum of a fifth one or more pulses 4424, and an Nth frame 4426 may be generated based on a spectrum of an Nth one or more pulses 4426.

The pulses 4416-4426 may include energy from a single emitter or from a combination of two or more emitters. For example, the spectrum included in a single readout period or within the plurality of frames 4404-4414 may be selected for a desired examination or detection of a specific tissue or condition. According to one embodiment, one or more pulses may include visible spectrum light for generating a color or black and white image while one or more additional pulses are used to obtain spectral response to classify a type of tissue. For example, pulse 4416 may include red light, pulse 4418 may include blue light, and pulse 4420 may include green light while the remaining pulses 4422-4426 may include wavelengths and spectrums for detecting a specific tissue type. As a further example, pulses for a single readout period may include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on the spectral response.

The plurality of frames 4404-4414 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

A hyperspectral image or hyperspectral image data obtained in a manner illustrated in FIG. 44 may result in a plurality of frames, each based on a different spectrum or combination of spectrums. In some cases, tens or hundreds of different frames may be obtained. In other cases, such as for video streams, the number of frames may be limited to provide a viewable frame rate. Because combinations of different spectrums may be provided in a single readout period, useful and dynamic spectral information may still be obtained even in a video stream.

In one embodiment, a video or other image may include a black and white or color image overlaid with information derived from the spectral response for each pixel. For example, pixels that correspond to a specific tissue or state may be shown in a bright green or other color to assist a doctor or other medical expert during an examination.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In one embodiment, multispectral or hyperspectral imaging may be used to look through materials or substances. For example, infrared wavelengths may pass through some tissues, such as muscle or fat, while reflecting off blood vessels. In one embodiment, infrared waves may penetrate 5, 8 or 10 mm or more into a tissue. Obtaining a series of frames that includes at least one infrared frame may allow an examination to provide information about the location of blood vessels below the surface. This can be extremely helpful for surgical procedures where it may be desirable to perform incisions that avoid blood vessels. In one embodiment, a color or greyscale image may be overlaid with a green color that indicates the location of blood vessels below the surface. Similarly, a known spectral response of blood may be used to look through the blood and see the tissues or structures of interest in an examination.

Assembly of the subframes into a single frame for display on a monitor or other display device may take place after capturing the series of frames 4404-4414. A color or greyscale image may be generated from one or more of the frames and overlay information for pixels may be determined based on all or the remaining frames. The color or greyscale image mat be combined with the overlay information to generate a single frame. The single frame may be displayed as a single image or as an image in a video stream.

In one embodiment, the hyperspectral data obtained as illustrated in FIG. 44 may be provided for analysis by a third-party algorithm to classify a tissue or material captured in the image. In one embodiment, the third-party algorithm may be used to select the spectrums or wavebands to be used during imaging so that a desired spectral response analysis can be performed. In an embodiment, the spectral response analysis may be performed in real-time during a medical imaging procedure or other medical procedure. The spectral data may be overlaid on an RGB or black and white image such that a user may readily differentiate certain types of tissues, organs, chemical processes, diseases, and so forth. In an embodiment, the spectral data may be provided to a computer-operated system, such as a robotics system, for automation of medical imaging or medical procedures.

Figure 45:
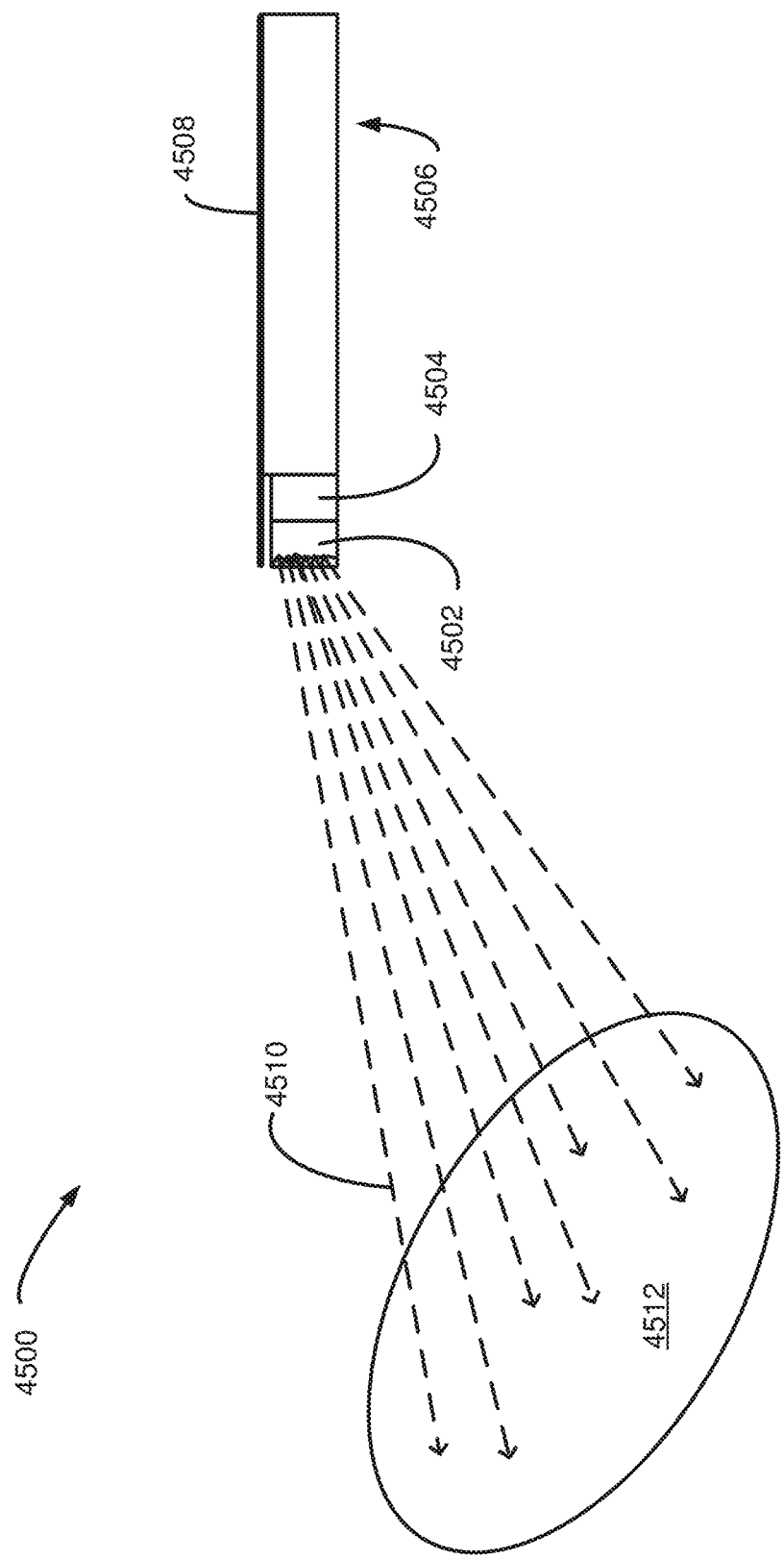
FIG. 45 is a block diagram illustrating generating a filtered image using a filter, according to one embodiment.

FIG. 45 is a schematic diagram of an imaging system 4500 having a single cut filter. The system 4500 includes an endoscope 4506 or other suitable imaging device having a light source 4508 for use in a light deficient environment. The endoscope 4506 includes an image sensor 4504 and a filter 4502 for filtering out unwanted wavelengths of light or other electromagnetic radiation before reaching the image sensor 4504. The light source 4508 transmits light that may illuminate the surface 4512 in a light deficient environment such as a body cavity. The light 4510 is reflected off the surface 4512 and passes through the filter 4502 before hitting the image sensor 4504.

The filter 4502 may be used in an implementation where a fluorescent reagent or dye has been administered. In such an embodiment, the filter 4502 is configured to filter out all light other than one or more desired wavelengths or spectral bands of light or other electromagnetic radiation. In one embodiment, the filter 4502 is configured to filter out an excitation wavelength of electromagnetic radiation that causes a reagent or dye to fluoresce such that only the expected relaxation wavelength of the fluoresced reagent or dye is permitted to pass through the filter 4502 and reach the image sensor 4504. In an embodiment, the filter 4502 filters out at least a fluorescent reagent excitation wavelength between 770 nm and 790 nm. In an embodiment, the filter 4502 filters out at least a fluorescent reagent excitation wavelength between 795 nm and 815 nm. In an embodiment, the filter 4502 filters out at least a fluorescent reagent excitation wavelength between 770 nm and 790 nm and between 795 nm and 815 nm. In these embodiments, the filter 4502 filters out the excitation wavelength of the reagent and permits only the relaxation wavelength of the fluoresced reagent to be read by the image sensor 4504. The image sensor 4504 may be a wavelength-agnostic image sensor and the filter 4502 may be configured to permit the image sensor 4504 to only receive the relaxation wavelength of the fluoresced reagent and not receive the emitted excitation wavelength for the reagent. The data determined by the image sensor 4504 may then indicate a presence of a critical body structure, tissue, biological process, or chemical process as determined by a location of the reagent or dye.

The filter 4502 may further be used in an implementation where a fluorescent reagent or dye has not been administered. The filter 4502 may be selected to permit wavelengths corresponding to a desired spectral response to pass through and be read by the image sensor 4504. The image sensor 4504 may be a monochromatic image sensor such that pixels of the captured image that exceed a threshold or fall below a threshold may be characterized as corresponding to a certain spectral response or fluorescence emission. The spectral response or fluorescence emission, as determined by the pixels captured by the image sensor 4504, may indicate the presence of a certain body tissue or structure, a certain condition, a certain chemical process, and so forth.

In one embodiment, the light source 4508 transmits white light that contacts the surface 4512 and is reflected back where it is filtered by the filter 4502 before it hits the image sensor 4504. In one embodiment, the light source 4508 transmits white light that passes through the filter 4502 such that filtered light of only one or more desired wavelengths emerges from the filter 4502 to be reflected off the surface 4512 and read by the image sensor 4504. For example, in an embodiment, the filter 4502 permits only light having a wavelength of 795 nm to pass through the filter 4502 and contact the image sensor 4504. Further in an embodiment, the filter 4502 permits only certain wavelengths of light to be reflected back to the image sensor 4504 of the endoscope 4506 or other imaging device. The filter 4502 may be located anywhere in the system 4500 or may be an attribute of a lens or the image sensor 4504. The filter 4502 may be located in front of and/or behind the image sensor 4504. In an embodiment, light emitted by the light source 4508 is filtered before it reaches the surface 4512 and the reflected light is filtered by an additional filter before it is ready by the image sensor 4504.

The light source 4508 may be an emitter that may be configured to emit white light or electromagnetic radiation of one or more specific wavelengths. The light source 4508 may include a plurality of lasers configured to emit or pulse light of specified wavelengths. In an embodiment, the light source 4508 emits white light and the filter 4502 is selected to filter all unwanted light other than one or more desired wavelengths of light or other electromagnetic radiation. The filter 4502 may be selected for a specific examination or purpose, for example to highlight a type of body tissue or structure, or to highlight a certain condition or chemical process.

Figure 46:
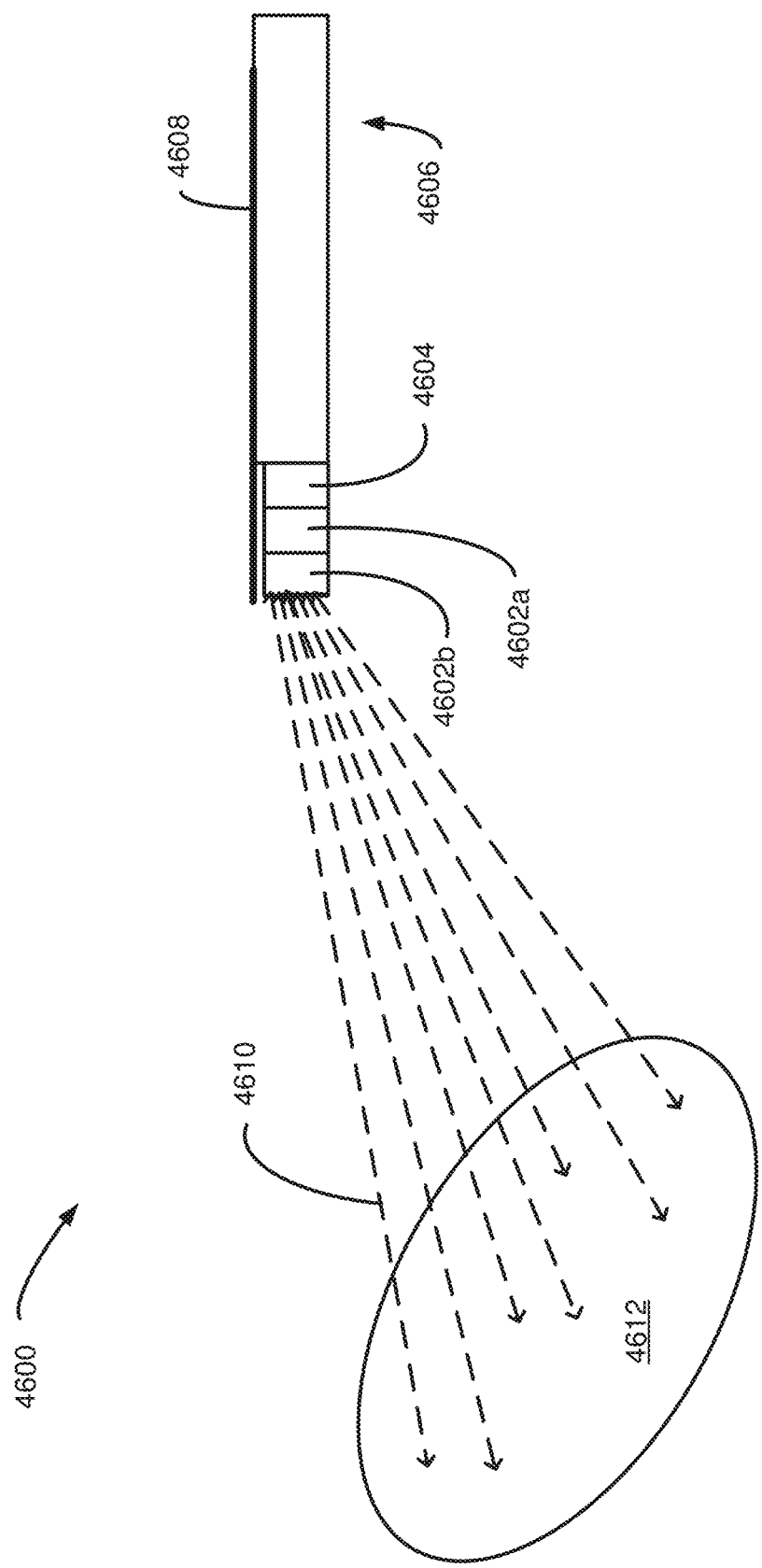
FIG. 46 is a block diagram illustrating generating a filtered image using a plurality of filters, according to one embodiment.

FIG. 46 is a schematic diagram of an imaging system 4600 having multiple cut filters. The system 4600 includes an endoscope 4606 or other suitable imaging device having a light source 4608 for use in a light deficient environment. The endoscope 4606 includes an image sensor 4604 and two filters 4602a, 4602b. It should be appreciated that in alternative embodiments, the system 4600 may include any number of filters, and the number of filters and the type of filters may be selected for a certain purpose e.g., for gathering imaging information of a particular body tissue, body condition, chemical process, and so forth. The filters 4602a, 4602b are configured for filtering out unwanted wavelengths of light or other electromagnetic radiation. The filters 4602a, 4602b may be configured to filter out unwanted wavelengths from white light or other electromagnetic radiation that may be emitted by the light source 4608. The filtered light may hit the surface 4612 (e.g. body tissue) and be reflected back on to the image sensor 4604.

Further to the disclosure with respect to FIG. 45, the filters 4602a, 4602b may be used in an implementation where a fluorescent reagent or dye has been administered. The filters 4602a, 4602b may be configured for blocking an emitted excitation wavelength for the reagent or dye and permitting the image sensor 4604 to only read the relaxation wavelength of the reagent or dye. Further, the filters 4602a, 4602b may be used in an implementation where a fluorescent reagent or dye has not been administered. In such an implementation, the filters 4602a, 4602b may be selected to permit wavelengths corresponding to a desired spectral response to pass through and be read by the image sensor 4604.

The multiple filters 4602a, 4602b may each be configured for filtering out a different range of wavelengths of the electromagnetic spectrum. For example, one filter may be configured for filtering out wavelengths longer than a desired wavelength range and the additional filter may be configured for filtering out wavelengths shorter than the desired wavelength range. The combination of the two or more filters may result in only a certain wavelength or band of wavelengths being read by the image sensor 4604.

In an embodiment, the filters 4602a, 4602b are customized such that electromagnetic radiation between 513 nm and 545 nm contacts the image sensor 4604. In an embodiment, the filters 4602a, 4602b are customized such that electromagnetic radiation between 565 nm and 585 nm contacts the image sensor 4604. In an embodiment, the filters 4602a, 4602b are customized such that electromagnetic radiation between 900 nm and 1000 nm contacts the image sensor 4604. In an embodiment, the filters 4602a, 4602b are customized such that electromagnetic radiation between 425 nm and 475 nm contacts the image sensor 4604. In an embodiment, the filters 4602a, 4602b are customized such that electromagnetic radiation between 520 nm and 545 nm contacts the image sensor 4604. In an embodiment, the filters 4602a, 4602b are customized such that electromagnetic radiation between 625 nm and 645 nm contacts the image sensor 4604. In an embodiment, the filters 4602a, 4602b are customized such that electromagnetic radiation between 760 nm and 795 nm contacts the image sensor 4604. In an embodiment, the filters 4602a, 4602b are customized such that electromagnetic radiation between 795 nm and 815 nm contacts the image sensor 4604. In an embodiment, the filters 4602a, 4602b are customized such that electromagnetic radiation between 370 nm and 420 nm contacts the image sensor 4604. In an embodiment, the filters 4602a, 4602b are customized such that electromagnetic radiation between 600 nm and 670 nm contacts the image sensor 4604. In an embodiment, the filters 4602a, 4602b are configured for permitting only a certain fluorescence relaxation emission to pass through the filters 4602a, 4602b and contact the image sensor 4604.

In an embodiment, the system 4600 includes multiple image sensors 4604 and may particularly include two image sensors for use in generating a three-dimensional image. The image sensor(s) 4604 may be color/wavelength agnostic and configured for reading any wavelength of electromagnetic radiation that is reflected off the surface 4612. In an embodiment, the image sensors 4604 are each color dependent or wavelength dependent and configured for reading electromagnetic radiation of a particular wavelength that is reflected off the surface 4612 and back to the image sensors 4604. Alternatively, the image sensor 4604 may include a single image sensor with a plurality of different pixel sensors configured for reading different wavelengths or colors of light, such as a Bayer filter color filter array. Alternatively, the image sensor 4604 may include one or more color agnostic image sensors that may be configured for reading different wavelengths of electromagnetic radiation according to a pulsing schedule such as those illustrated in FIGS. 5-7E and 15-16, for example.

Figure 47:
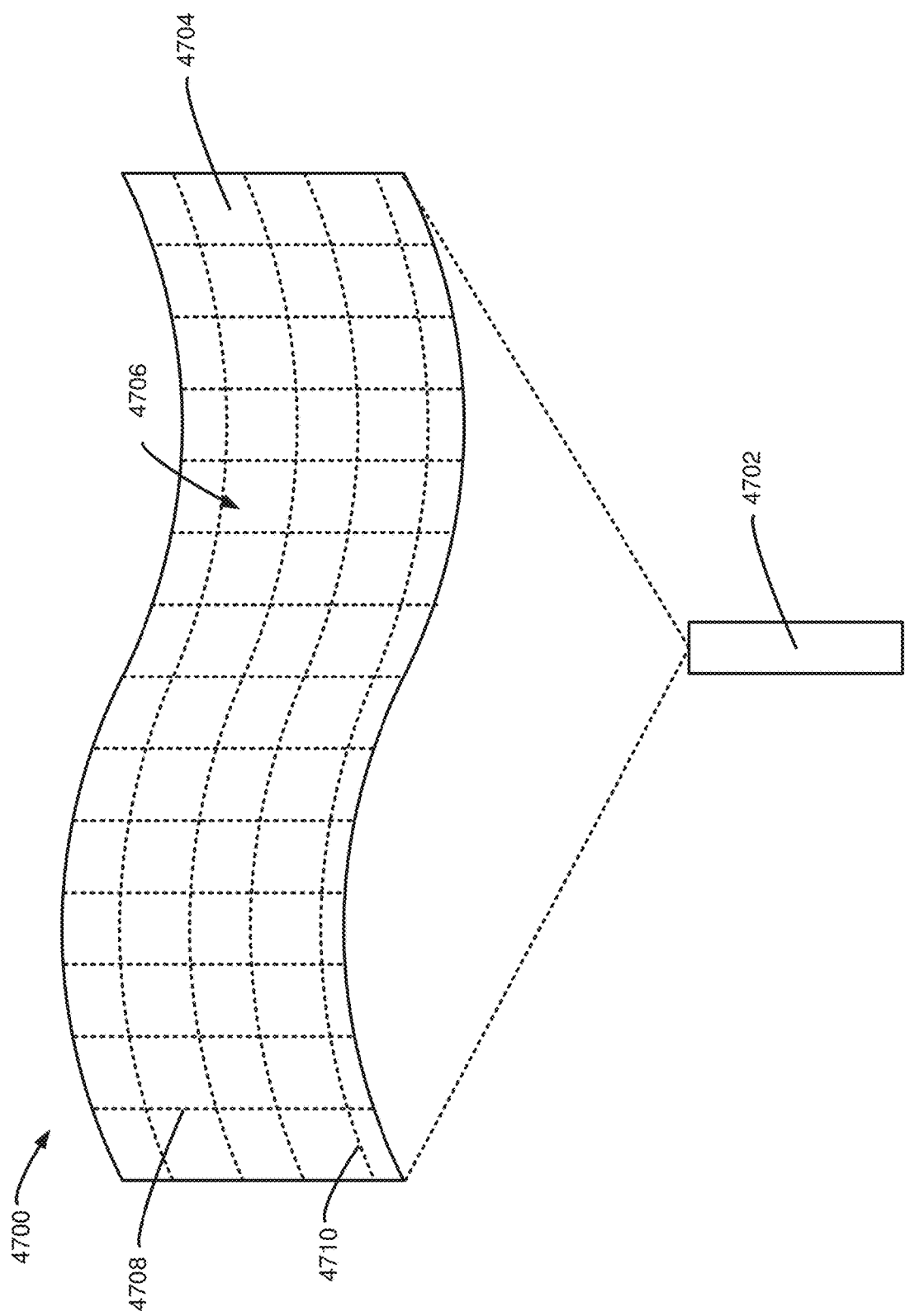
FIG. 47 is a schematic diagram illustrating a grid array for object and/or surface tracking, according to one embodiment.

FIG. 47 is a schematic diagram illustrating a system 4700 for mapping a surface and/or tracking an object in a light deficient environment. In an embodiment, an endoscope 4702 in a light deficient environment pulses a grid array 4706 (may be referred to as a laser map pattern) on a surface 4704. The grid array 4706 may include vertical hashing 4708 and horizontal hashing 4710 in one embodiment as illustrated in FIG. 47. The It should be appreciated the grid array 4706 may include any suitable array for mapping a surface 4704, including, for example, a raster grid of discrete points, an occupancy grid map, a dot array, and so forth. Additionally, the endoscope 4702 may pulse multiple grid arrays 4706 and may, for example, pulse one or more individual grid arrays on each of a plurality of objects or structures within the light deficient environment.

In an embodiment, the system 4700 pulses a grid array 4706 that may be used for determining a three-dimensional surface and/or tracking a location of an object such as a tool or another device in a light deficient environment. In an embodiment, the system 4700 may provide data to a third party system or computer algorithm for determining surface dimensions and configurations by way of light detection and ranging (LIDAR) mapping. The system 4700 may pulse any suitable wavelength of light or electromagnetic radiation in the grid array 4706, including, for example, ultraviolet light, visible, light, and/or infrared or near infrared light. The surface 4704 and/or objects within the environment may be mapped and tracked at very high resolution and with very high accuracy and precision.

In an embodiment, the system 4700 includes an imaging device having a tube, one or more image sensors, and a lens assembly having an optical element corresponding to the one or more image sensors. The system 4700 may include a light engine having an illumination source generating one or more pulses of electromagnetic radiation and a lumen transmitting the one or more pulses of electromagnetic radiation to a distal tip of an endoscope within a light deficient environment such as a body cavity. In an embodiment, at least a portion of the one or more pulses of electromagnetic radiation includes a laser map pattern that is emitted onto a surface within the light deficient environment, such as a surface of body tissue and/or a surface of tools or other devices within the body cavity. The endoscope 4702 may include a two-dimensional, three-dimensional, or n-dimensional camera for mapping and/or tracking the surface, dimensions, and configurations within the light deficient environment.

In an embodiment, the system 4700 includes a processor for determining a distance of an endoscope or tool from an object such as the surface 4704. The processor may further determine an angle between the endoscope or tool and the object. The processor may further determine surface area information about the object, including for example, the size of surgical tools, the size of structures, the size of anatomical structures, location information, and other positional data and metrics. The system 4700 may include one or more image sensors that provide image data that is output to a control system for determining a distance of an endoscope or tool to an object such as the surface 4704. The image sensors may output information to a control system for determining an angle between the endoscope or tool to the object. Additionally, the image sensors may output information to a control system for determining surface area information about the object, the size of surgical tools, size of structures, size of anatomical structures, location information, and other positional data and metrics.

In an embodiment, the grid array 4706 is pulsed by an illumination source of the endoscope 4702 at a sufficient speed such that the grid array 4706 is not visible to a user. In various implementations, it may be distracting to a user to see the grid array 4706 during an endoscopic imaging procedure and/or endoscopic surgical procedure. The grid array 4706 may be pulsed for sufficiently brief periods such that the grid array 4706 cannot be detected by a human eye. In an alternative embodiment, the endoscope 4702 pulses the grid array 4706 at a sufficient recurring frequency such that the grid array 4706 may be viewed by a user. In such an embodiment, the grid array 4706 may be overlaid on an image of the surface 4704 on a display. The grid array 4706 may be overlaid on a black-and-white or RGB image of the surface 4704 such that the grid array 4706 may be visible by a user during use of the system 4700. A user of the system 4700 may indicate whether the grid array 4706 should be overlaid on an image of the surface 4704 and/or whether the grid array 4706 should be visible to the user. The system 4700 may include a display that provides real-time measurements of a distance from the endoscope 4702 to the surface 4704 or another object within the light deficient environment. The display may further provide real-time surface area information about the surface 4704 and/or any objects, structures, or tools within the light deficient environment. The accuracy of the measurements may be accurate to less than one millimeter.

The endoscope 4702 may pulse electromagnetic radiation according to a pulsing schedule such as those illustrated in FIGS. 5-7E and 15-16, for example, that may further include pulsing of the grid array 4706 along with pulsing Red, Green, and Blue light for generating an RGB image and further generating a grid array 4706 that may be overlaid on the RGB image and/or used for mapping and tracking the surface 4704 and objects within the light deficient environment.

In an embodiment, the endoscope 4702 includes one or more color agnostic image sensors. In an embodiment, the endoscope 4702 includes two color agnostic image sensors for generating a three-dimensional image or map of the light deficient environment. The image sensors may generate an RGB image of the light deficient environment according to a pulsing schedule as disclosed herein. Additionally, the image sensors may determine data for mapping the light deficient environment and tracking one or more objects within the light deficient environment based on data determined when the grid array 4706 is pulsed. Additionally, the image sensors may determine spectral or hyperspectral data along with fluorescence imaging data according to a pulsing schedule that may be modified by a user to suit the particular needs of an imaging procedure. In an embodiment, a pulsing schedule includes Red, Green, and Blue pulses along with pulsing of a grid array 4706 and/or pulsing for generating hyperspectral image data and/or fluorescence image data. In various implementations, the pulsing schedule may include any suitable combination of pulses of electromagnetic radiation according to the needs of a user. The recurring frequency of the different wavelengths of electromagnetic radiation may be determined based on, for example, the energy of a certain pulse, the needs of the user, whether certain data (for example, hyperspectral data and/or fluorescence imaging data) needs to be continuously updated or may be updated less frequently, and so forth.

The pulsing schedule may be modified in any suitable manner, and certain pulses of electromagnetic radiation may be repeated at any suitable frequency, according to the needs of a user or computer-implemented program for a certain imaging procedure. For example, in an embodiment where surface tracking data generated based on the grid array 4706 is provided to a computer-implemented program for use in, for example, a robotic surgical procedure, the grid array 4706 may be pulsed more frequently than if the surface tracking data is provided to a user who is visualizing the scene during the imaging procedure. In such an embodiment where the surface tracking data is used for a robotic surgical procedure, the surface tracking data may need to be updated more frequently or may need to be exceedingly accurate such that the computer-implemented program may execute the robotic surgical procedure with precision and accuracy.

In an embodiment, the system 4700 is configured to generate an occupancy grid map comprising an array of cells divided into grids. The system 4700 is configured to store height values for each of the respective grid cells to determine a surface mapping of a three-dimensional environment in a light deficient environment.

Figure 48:
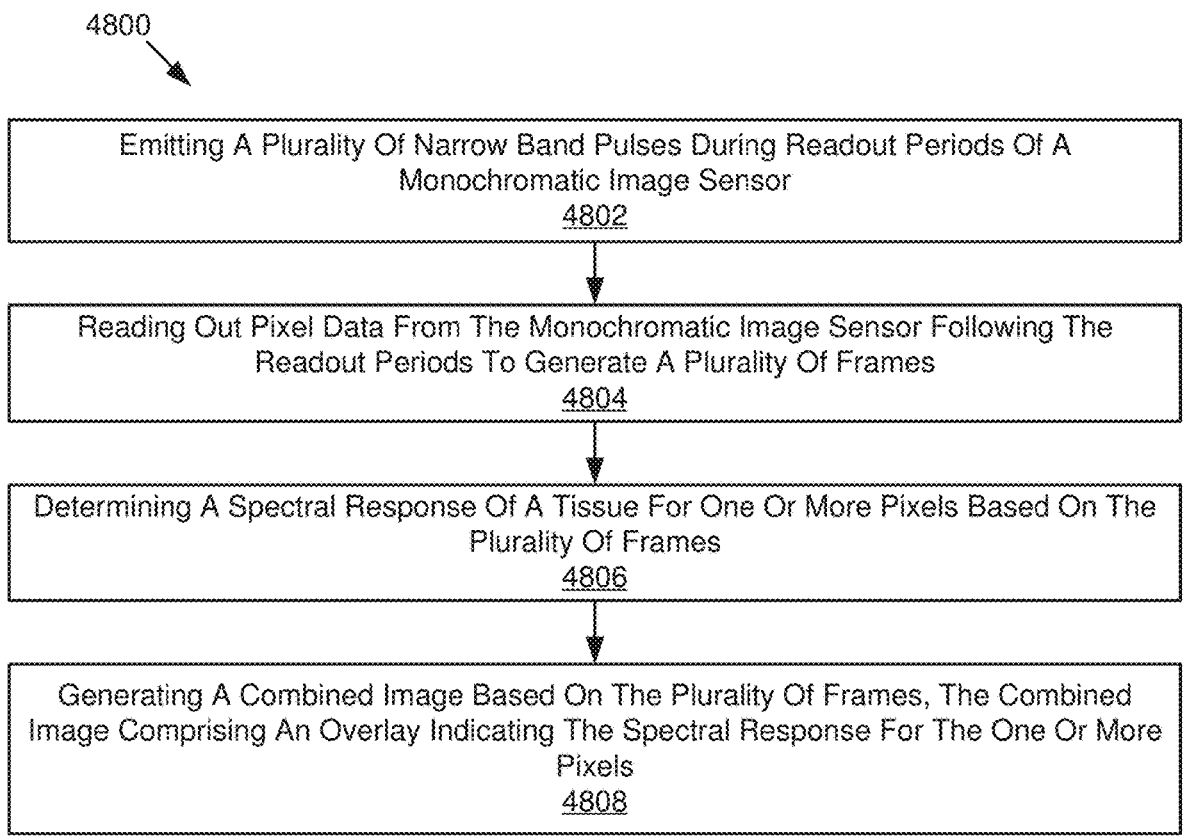
FIG. 48 is a schematic flow chart diagram illustrating a method for emission and readout for generating a multispectral or hyperspectral image, according to one embodiment.

FIG. 48 is a schematic flow chart diagram for a method 4800 for hyperspectral imaging in a light deficient environment. The method 4800 may be performed by an imaging system, such as an endoscopic imaging system illustrated in FIG. 37.

The method 4800 includes emitting at 4802 a plurality of narrow band pulses during readout periods of a monochromatic image sensor. The pulses may be emitted at 4802 using a light source that includes a plurality of emitters that emit electromagnetic energy within the narrow frequency bands. For example, the light source may include at least one emitter for a plurality of frequency bands covering a desired spectrum. A monochromatic image sensor reads out at 4804 pixel data from the monochromatic image sensor following the readout periods to generate a plurality of frames. Each frame may include a different spectral content. These frames may include a plurality of repeating frames that may be used for generating a digital video stream. Each frame may be based energy emitted by one or more emitters of the light source. In one embodiment, a frame may be based on a combination of light emitted by light sources to generate a combination of frequencies to match a frequency response of a desired tissue or substance. A controller, CCU, or other system determines at 4806 a spectral response of a tissue for one or more pixels based on the plurality of frames. For example, the pixel values and knowledge about the frequencies of light emitted for each frame may be used to determine a frequency response for a specific pixel, based on the values for the pixel in the plurality of frames. The system may generate at 4808 a combined image based on the plurality of frames, the combined image comprising an overlay indicating the spectral response for the one or more pixels. For example, the combined image may be a greyscale or color image where pixels corresponding to a specific tissue or classification are shown in bright green.

Figure 49:
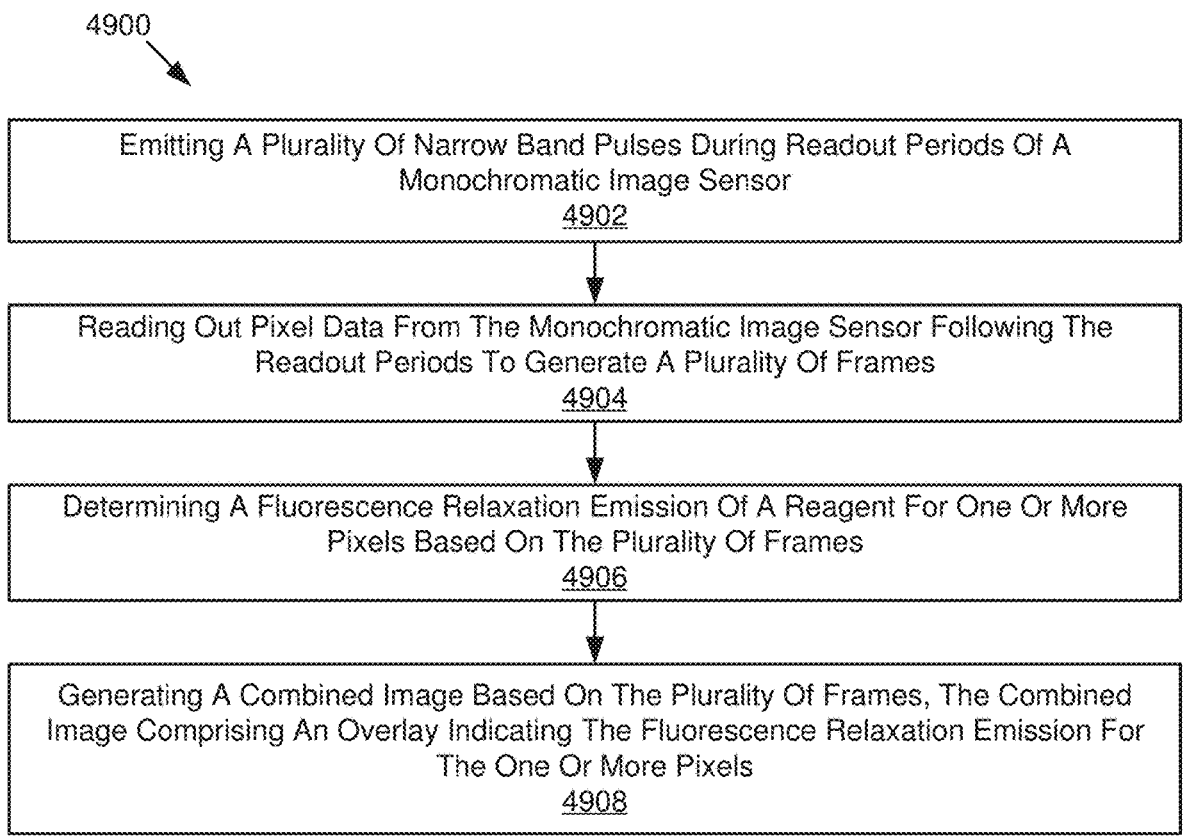
FIG. 49 is a schematic flow chart diagram illustrating a method for emission and readout for generating a fluorescence image, according to one embodiment.

FIG. 49 is a schematic flow chart diagram for a method 4900 for fluorescence imaging in a light deficient environment. The method 4900 may be performed by an imaging system, such as an endoscopic imaging system illustrated in FIG. 37.

The method 4900 includes emitting at 4902 a plurality of narrow band pulses during readout periods of a monochromatic image sensor. The pulses may be emitted at 4902 using a light source that includes a plurality of emitters that emit electromagnetic energy within the narrow frequency bands. For example, the light source may include at least one emitter for a plurality of frequency bands covering a desired spectrum. A monochromatic image sensor reads out at 4904 pixel data from the monochromatic image sensor following the readout periods to generate a plurality of frames. Each frame may include a different spectral content. These frames may include a plurality of repeating frames that may be used for generating a digital video stream. Each frame may be based energy emitted by one or more emitters of the light source. In one embodiment, a frame may be based on a combination of light emitted by light sources to generate a combination of frequencies to match a frequency response of a desired tissue or substance. A controller, CCU, or other system determines at 4906 a fluorescence relaxation emission of a reagent for one or more pixels based on the plurality of frames. For example, the pixel values and knowledge about the frequencies of light emitted for each frame may be used to determine a frequency response for a specific pixel, based on the values for the pixel in the plurality of frames. The system may generate at 4908 a combined image based on the plurality of frames, the combined image comprising an overlay indicating the fluorescence relaxation emission for the one or more pixels. For example, the combined image may be a grey scale or color image where pixels corresponding to a specific tissue or classification are shown in bright green.

EXAMPLES

The following examples pertain to further embodiments:

Example 1 is an endoscopic system for use in a light deficient environment. The system includes an imaging device. The imaging device includes a tube, one or more image sensors, and a lens assembly comprising at least one optical element corresponding to the image sensor. The system includes a display for a user to visualize a scene and an image signal processing controller. The system includes a light engine. The light engine includes an illumination source generating a plurality of pulses of electromagnetic radiation. The light engine further includes a lumen transmitting one or more pulses of electromagnetic radiation to a distal tip of an endoscope, wherein the plurality of pulses of electromagnetic radiation transmitted over the time period comprises a red pulse, a green pulse, and a blue pulse, and further comprises one or more of: an excitation wavelength of electromagnetic radiation between 513 nm and 545 nm, an excitation wavelength of electromagnetic radiation between 565 nm and 585 nm, an excitation wavelength of electromagnetic radiation between 900 nm and 1000 nm, an excitation wavelength of electromagnetic radiation that causes a reagent to fluoresce, or a laser map pattern that is emitted on to a surface of a body tissue.

Example 2 is an endoscopic system as in Example 1, wherein a duration of each pulse of the plurality of pulses of electromagnetic radiation transmitted over the time period is variable.

Example 3 is an endoscopic system as in any of Examples 1-2, wherein during a pulse duration a plurality of sub-pulses of electromagnetic radiation having a sub-duration are emitted, and wherein the sub-duration is shorter than the pulse duration.

Example 4 is an endoscopic system as in any of Examples 1-3, wherein the pulse sub-durations in the pulse duration are different for each sub-pulse of electromagnetic radiation.

Example 5 is an endoscopic system as in any of Examples 1-4, wherein the pulse sub-durations in the pulse duration comprise two or more sub-pulses of electromagnetic radiation with equal duration.

Example 6 is an endoscopic system as in any of Examples 1-5, wherein one or more of the plurality of sub-pulses comprises electromagnetic radiation emitted at two or more wavelengths simultaneously as a single pulse or a single sub-pulse.

Example 7 is an endoscopic system as in any of Examples 1-6, wherein the sub-durations of the plurality of sub-pulses are variable in both electromagnetic radiation wavelengths emitted and in the number of emissions occurring per pulse duration.

Example 8 is an endoscopic system as in any of Examples 1-7, wherein the sub-durations of the plurality of sub-pulses are equivalent to a single pulse duration that provides a single frame exposure of the video stream.

Example 9 is an endoscopic system as in any of Examples 1-8, wherein a duration of the time period is variable.

Example 10 is an endoscopic system as in any of Examples 1-9, wherein the plurality of pulses of electromagnetic radiation transmitted over the time period is adjustable by a user of the endoscopic light engine.

Example 11 is an endoscopic system as in any of Examples 1-10, further comprising a control system for illuminating the scene, wherein the control system automatically adjusts or changes the plurality of pulses of electromagnetic radiation transmitted over the time period based on a threshold, wherein the threshold determines proper illumination of the scene.

Example 12 is an endoscopic system as in any of Examples 1-11, wherein each pulse of the plurality of pulses of electromagnetic radiation transmitted over the time period is an exposure frame created by the image sensor, and wherein one or more exposure frames are displayed to a user as a single image on the display as part of the video stream.

Example 13 is an endoscopic system as in any of Examples 1-12, wherein each pulse of the plurality of pulses of electromagnetic radiation transmitted over the time period is an exposure frame created by the image sensor, and wherein the plurality of pulses of electromagnetic radiation transmitted over the time period are displayed to a user as a single image on the display as part of the video stream.

Example 14 is an endoscopic system as in any of Examples 1-13, wherein each pulse of the plurality of pulses of electromagnetic radiation transmitted over the time period is an exposure frame created by the image sensor, and wherein one or more exposure frames are displayed to a user as an overlay image on the display as part of the video stream.

Example 15 is an endoscopic system as in any of Examples 1-14, wherein the illumination source generates one or more pulses of electromagnetic radiation using one or more laser emitters.

Example 16 is an endoscopic system as in any of Examples 1-15, wherein each pulse of electromagnetic radiation results in an exposure frame created by the image sensor, and wherein one or more exposure frames are displayed to a user as a single image on the display as part of the video stream.

Example 17 is an endoscopic system as in any of Examples 1-16, wherein the single image is assigned a visible color for use on the display, and wherein the visible color is 8-bit or 16-bit or n-bit.

Example 18 is an endoscopic system as in any of Examples 1-17, wherein the plurality of pulses of electromagnetic radiation transmitted over the time period further comprises an excitation wavelength of electromagnetic radiation between 425 nm and 475 nm.

Example 19 is an endoscopic system as in any of Examples 1-18, wherein the plurality of pulses of electromagnetic radiation transmitted over the time period further comprises an excitation wavelength of electromagnetic radiation between 520 nm and 545 nm.

Example 20 is an endoscopic system as in any of Examples 1-19, wherein the plurality of pulses of electromagnetic radiation transmitted over the time period further comprises an excitation wavelength of electromagnetic radiation between 625 nm and 645 nm.

Example 21 is an endoscopic system as in any of Examples 1-20, wherein the plurality of pulses of electromagnetic radiation transmitted over the time period further comprises an excitation wavelength of electromagnetic radiation between 760 nm and 795 nm.

Example 22 is an endoscopic system as in any of Examples 1-21, wherein the plurality of pulses of electromagnetic radiation transmitted over the time period further comprises an excitation wavelength of electromagnetic radiation between 795 nm and 815 nm.

Example 23 is an endoscopic system as in any of Examples 1-22, wherein the plurality of pulses of electromagnetic radiation transmitted over the time period further comprises an excitation wavelength of electromagnetic radiation between 370 nm and 420 nm.

Example 24 is an endoscopic system as in any of Examples 1-23, wherein the plurality of pulses of electromagnetic radiation transmitted over the time period further comprises an excitation wavelength of electromagnetic radiation between 600 nm and 670 nm.

Example 25 is an endoscopic system as in any of Examples 1-24, wherein the light engine comprises a polarization filter.

Example 26 is an endoscopic system as in any of Examples 1-25, wherein the polarization filter is located in a path of the electromagnetic radiation.

Example 27 is an endoscopic system as in any of Examples 1-26, wherein the polarization filter is located at a proximal end of the lumen.

Example 28 is an endoscopic system as in any of Examples 1-27, wherein the polarization filter is located at a distal end of the lumen.

Example 29 is an endoscopic system as in any of Examples 1-28, wherein the lens assembly comprises an electromagnetic radiation filter.

Example 30 is an endoscopic system as in any of Examples 1-29, wherein the lens assembly comprises a polarization filter.

Example 31 is an endoscopic system as in any of Examples 1-30, wherein each pulse of the plurality of pulses of electromagnetic radiation transmitted over the time period results in an exposure frame created by the image sensor, and wherein one or more exposure frames is fed to a corresponding system that will provide location of critical tissue structures in the scene.

Example 32 is an endoscopic system as in any of Examples 1-31, wherein the location of the critical tissue structures in the scene is received by the endoscopic system and overlaid on the display, and wherein the critical tissue structures are encoded to any color selected by either an algorithm or a user.

Example 33 is an endoscopic system as in any of Examples 1-32, wherein the system further comprises a filter that blocks the excitation wavelength of electromagnetic radiation that causes the reagent to fluoresce.

Example 34 is an endoscopic system as in any of Examples 1-33, wherein the filter is located on the at least one optical element of the lens assembly such that the filter blocks the excitation wavelength and allows a wavelength of the fluorescing reagent through the filter.

Example 35 is an endoscopic system as in any of Examples 1-34, wherein the image sensor detects a wavelength of the fluorescing reagent to provide an image of one or more critical structures in a human body.

Example 36 is an endoscopic system as in any of Examples 1-35, wherein the one or more critical structures in the human body comprises one of a nerve, a ureter, a blood vessel, an artery, a blood flow, or a tumor.

Example 37 is an endoscopic system as in any of Examples 1-36, wherein the one or more critical structures in the human body are cancer cells, and wherein the system receives fluoresced electromagnetic radiation from a molecule that attaches a fluorophore that fluoresces when exposed to electromagnetic radiation having a wavelength between 770 nm and 790 nm to one or more of the cancer cells.

Example 38 is an endoscopic system as in any of Examples 1-37, wherein the excitation wavelength of electromagnetic radiation that causes a reagent to fluoresce is between 770 nm and 790 nm.

Example 39 is an endoscopic system as in any of Examples 1-38, further comprising a filter that blocks the excitation wavelength of electromagnetic radiation between 770 nm and 790 nm.

Example 40 is an endoscopic system as in any of Examples 1-39, wherein the excitation wavelength of electromagnetic radiation that causes a reagent to fluoresce is between 795 nm and 815 nm.

Example 41 is an endoscopic system as in any of Examples 1-40, further comprising a filter that blocks the excitation wavelength of electromagnetic radiation between 795 nm and 815 nm.

Example 42 is an endoscopic system as in any of Examples 1-41, wherein the one or more critical structures in the human body are cancer cells, and wherein the system receives fluoresced electromagnetic radiation from a molecule that attaches a fluorophore that fluoresces when exposed to electromagnetic radiation having a wavelength between 795 nm and 815 nm to one or more of the cancer cells.

Example 43 is an endoscopic system as in any of Examples 1-42, wherein the excitation wavelength of electromagnetic radiation that causes a reagent to fluoresce comprises: one or more pulses of electromagnetic radiation between 770 nm and 790 nm, and one or more pulses of electromagnetic radiation between 795 nm and 815 nm.

Example 44 is an endoscopic system as in any of Examples 1-43, further comprising a filter that blocks the excitation wavelength of electromagnetic radiation between 770 nm and 790 nm.

Example 45 is an endoscopic system as in any of Examples 1-44, further comprising a filter that blocks the excitation wavelength of electromagnetic radiation between 795 nm and 815 nm.

Example 46 is an endoscopic system as in any of Examples 1-45, further comprising a first filter that filters electromagnetic radiation between 770 nm and 790 nm and a second filter that filters electromagnetic radiation between 795 nm and 815 nm.

Example 47 is an endoscopic system as in any of Examples 1-46, further comprising one or more filters that allow electromagnetic radiation between 790 nm and 800 nm and above 815 nm to pass through the one or more filters to the image sensor.

Example 48 is an endoscopic system as in any of Examples 1-47, wherein the one or more critical structures in the human body are cancer cells, and wherein the system receives fluoresced electromagnetic radiation from a molecule that attaches a fluorophore that fluoresces when exposed to electromagnetic radiation having a wavelength between 770 nm and 790 nm and between 705 nm and 815 nm to one or more of the cancer cells.

Example 49 is an endoscopic system as in any of Examples 1-48, wherein the imaging device comprises a first image sensor and a second image sensor to produce a three-dimensional image.

Example 50 is an endoscopic system as in any of Examples 1-49, wherein the first image sensor receives electromagnetic radiation about 815 nm.

Example 51 is an endoscopic system as in any of Examples 1-50, wherein the second image sensor receives electromagnetic radiation between 785 nm and 800 nm.

Example 52 is an endoscopic system as in any of Examples 1-51, wherein the first image sensor comprises one or more filters that filters the electromagnetic radiation between 770 nm and 815 nm and the second image sensor comprises one or more filters that filters the electromagnetic radiation between 760 nm and 785 nm and electromagnetic radiation between 800 nm and 850 nm.

Example 53 is an endoscopic system as in any of Examples 1-52, wherein the system comprises a first filter that filters electromagnetic radiation between 770 nm and 815 nm.

Example 54 is an endoscopic system as in any of Examples 1-53, wherein the system comprises a second filter that filters electromagnetic radiation between 760 nm and 785 nm and electromagnetic radiation between 800 nm and 850 nm.

Example 55 is an endoscopic system for use in a light deficient environment. The system includes an imaging device. The imaging device includes a tube, one or more image sensors, and a lens assembly comprising at least one optical element corresponding to the image sensor. The system includes a display for a user to visualize a scene and an image signal processing controller. The system includes a light engine. The light engine includes an illumination source generating a plurality of pulses of electromagnetic radiation. The light engine further includes a lumen transmitting one or more pulses of electromagnetic radiation to a distal tip of an endoscope, wherein the plurality of pulses of electromagnetic radiation transmitted over the time period comprises a red pulse, a green pulse, and a blue pulse, an excitation wavelength of electromagnetic radiation between 513 nm and 545 nm, an excitation wavelength of electromagnetic radiation between 565 nm and 585 nm, an excitation wavelength of electromagnetic radiation between 900 nm and 1000 nm, an excitation wavelength of electromagnetic radiation that causes a reagent to fluoresce, or a laser map pattern that is emitted on to a surface of a body tissue.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements and embodiments may be combined in a single embodiment comprising any combination of the disclosed embodiments, including comprising all disclosed embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

The invention claimed is:

1. An endoscopic system for use in a light deficient environment for capturing color and spectral visualization data, the system comprising:
   an endoscope comprising:
      a tube;
      an image sensor comprising a pixel array that detects electromagnetic radiation and reads out image data; and
      a lens assembly comprising at least one optical element corresponding to the image sensor;
   a light engine that cycles a plurality of sources of electromagnetic radiation on and off according to a pulse cycle to emit a plurality of pulses of electromagnetic radiation, wherein the plurality of sources comprises:
      a first spectral source that emits electromagnetic radiation within a first spectral waveband; and
      a second spectral source that emits electromagnetic radiation within a second spectral waveband;
      wherein the first spectral waveband is different from the second spectral waveband; and
   a controller in communication with the image sensor and the light engine, wherein the controller is configured to:
      receive a user input requesting that an output video stream comprises color imaging data, dimensional information, and an overlay that highlights a target tissue;
      identify two or more sources of the plurality of sources to be pulsed to generate the color imaging data and to identify the target tissue with an algorithm;
      determine a recurring frequency for pulsing each of the two or more sources to generate the video stream according to the user input;
      calculate the pulse cycle for the light engine based on the recurring frequency for pulsing each of the two or more sources; and
      instruct the light engine to cycle the plurality of sources on and off according to the pulse cycle;
   wherein the dimensional information comprises one or more of a dimension, surface area, or relative position of one or more of a surgical tool, anatomical structure, or object within a scene.

2. The endoscopic system of claim 1, wherein the controller is configured to calculate the pulse cycle further based on an optimized a pulse duration for each of the two or more sources for capturing the color imaging data, the dimensional information, and for identifying the target tissue with the algorithm, wherein the pulse duration for each of the plurality of sources of the light engine is variable.

3. The endoscopic system of claim 1, wherein the controller calculates the pulse cycle such that at least one source of the plurality of sources emits a plurality of sub-pulses of electromagnetic radiation during a single pulse duration corresponding with a single blanking period of the image sensor.

4. The endoscopic system of claim 3, wherein two or more of the plurality of sub-pulses of electromagnetic radiation are emitted for a different duration.

5. The endoscopic system of claim 3, wherein two or more of the plurality of sub-pulses of electromagnetic radiation are emitted for an equal duration; and
   wherein the single pulse duration comprises two or more wavelengths of electromagnetic radiation emitted simultaneously.

6. The endoscopic system of claim 3, wherein the light engine cycles the plurality of sources such that the single pulse duration comprises two or more different wavelengths of electromagnetic radiation and further such that two or more of the plurality of sub-pulses are emitted for a different duration.

7. The endoscopic system of claim 1, wherein the two or more sources of electromagnetic radiation pulsed according to the pulse cycle pattern comprises:
a visible source that pulses electromagnetic radiation within a visible waveband, wherein pulses by the visible source correspond with the image sensor outputting the color imaging data; and
one or more of the first spectral source or the second spectral source, wherein pulses by the one or more of the first spectral source or the second spectral source correspond with the image sensor outputting data for identifying the target tissue with the algorithm.

8. The endoscopic system of claim 1, wherein the controller receives color image data and spectral image data from the image sensor, and wherein the controller combines the color image data and the spectral image data to generate overlay image data, and wherein the spectral image data is sensed by the pixel array in response to the light engine pulsing one or more of:
the first spectral waveband;
the second spectral waveband; or
a third spectral waveband;
wherein at least one of the first spectral waveband, the second spectral waveband, or the third spectral waveband is selected for multispectral imaging.

9. The endoscopic system of claim 1, wherein the controller is further configured to automatically adjust the plurality of pulses of electromagnetic radiation emitted according to the pulse cycle based on a threshold, wherein the threshold determines proper illumination for visualizing the scene with the image sensor.

10. The endoscopic system of claim 1, wherein the pixel array detects the electromagnetic radiation and reads out the image data in response to each of a plurality of pulse durations, and wherein the light engine emits one or more pulses of electromagnetic radiation during each pulse duration of the plurality of pulse durations.

11. The endoscopic system of claim 10, wherein the pixel array reads out the image data for generating a plurality of exposure frames, and wherein each of the plurality of exposure frames comprises to one pulse duration of the plurality of pulse durations.

12. The endoscopic system of claim 11, wherein data from two or more of the plurality of exposure frames are displayed to a user as an overlay image, and wherein the overlay image comprises a depiction of the one or more of the dimension, surface area, or relative position of the one or more of the surgical tool, anatomical structure, or object within the scene.

13. The endoscopic system of claim 1, wherein the pixel array detects the electromagnetic radiation and reads out the image data for generating an exposure frame in response to each pulse of the plurality of pulses of electromagnetic radiation emitted by the light engine, and wherein one or more exposure frames are displayed to a user as a single image on display as part of the video stream.

14. The endoscopic system of claim 1, wherein images outputs according to the video stream are assigned a visible color for use on a display, and wherein the visible color is 8-bit or 16-bit or n-bit.

15. The endoscopic system of claim 1, wherein the plurality of sources comprises a source tuned to emit only electromagnetic radiation within a waveband from about 425 nm to about 475 nm.

16. The endoscopic system of claim 1, wherein the plurality of sources comprises a source tuned to emit only electromagnetic radiation within a waveband from about 520 nm to about 545 nm.

17. The endoscopic system of claim 1, wherein the plurality of sources comprises a source tuned to emit only electromagnetic radiation within a waveband from about 625 nm to about 645 nm.

18. The endoscopic system of claim 1, wherein the plurality of sources comprises a source tuned to emit only electromagnetic radiation within a waveband from about 760 nm to about 795 nm.

19. The endoscopic system of claim 1, wherein the plurality of sources comprises a source tuned to emit only electromagnetic radiation within a waveband from about 795 nm to about 815 nm.

20. The endoscopic system of claim 1, wherein the plurality of sources comprises a source tuned to emit only electromagnetic radiation within a waveband from about 370 nm to about 420 nm.

21. The endoscopic system of claim 1, wherein the plurality of sources comprises a source tuned to emit only electromagnetic radiation within a waveband from about 600 nm to about 670 nm.

22. The endoscopic system of claim 1, wherein the plurality of sources of the light engine comprises:
the first spectral source tuned to emit the first spectral waveband, wherein the first spectral waveband comprises electromagnetic radiation from about 513 nm to about 545 nm;
the second spectral source tuned to emit the second spectral waveband, wherein the second spectral waveband comprises electromagnetic radiation from about 565 nm to about 585 nm;
a third spectral source tuned to emit a third spectral waveband, wherein the third spectral waveband comprises electromagnetic radiation from about 900 nm to about 1000 nm;
a fourth spectral source tuned to emit a fourth spectral waveband, wherein the fourth spectral waveband comprises electromagnetic radiation from about 770 nm to about 795 nm; and
a fifth spectral source tuned to emit a fifth spectral waveband, wherein the fifth spectral waveband comprises electromagnetic radiation from about 790 nm to about 815 nm.

23. The endoscopic system of claim 1, further comprising a polarization filter that is located in a path of the plurality of pulses of electromagnetic radiation emitted by the light engine.

24. The endoscopic system of claim 23, further comprising a waveguide that transmits the plurality of pulses of electromagnetic radiation from the light engine to a distal end of the tube of the endoscope, and wherein the polarization filter is located at a proximal end of the waveguide.

25. The endoscopic system of claim 23, further comprising a waveguide that transmits the plurality of pulses of electromagnetic radiation from the light engine to a distal end of the tube of the endoscope, and wherein the polarization filter is located at a distal end of the waveguide.

26. The endoscopic system of claim 1, further comprising a lens assembly and an electromagnetic radiation filter.

27. The endoscopic system of claim 1, wherein the plurality of sources of the light engine comprises a laser mapping source configured to emit light diffracted into a laser map pattern, and wherein the laser map pattern comprises one or more of vertical hashing, horizontal hashing, a raster grid of discrete points, an occupancy grid map, or a dot array.

28. The endoscopic system of claim 1, wherein the image sensor reads out a plurality of exposure frames that each correspond in time with at least one pulse of the plurality of pulses of electromagnetic radiation emitted by the light engine; and
wherein at least a portion of the plurality of exposure frames is provided to the algorithm to identify the target tissue within the scene.

29. The endoscopic system of claim 1, wherein the controller is further configured to:
provide imaging data to the algorithm to identify a location of the target tissue within the scene; and
render an overlay frame highlighting the target tissue based on an output received from the algorithm, wherein the highlight of the target tissue is encoded to any color selected by either an overlay algorithm or a user.

30. The endoscopic system of claim 1, wherein at least one of the first spectral waveband or the second spectral waveband is a fluorescence excitation wavelength that causes a reagent to fluoresce, and wherein the endoscopic system further comprises a filter that prevents the fluorescence excitation wavelength from irradiating the pixel array.

31. The endoscopic system of claim 30, wherein the filter is located on an optical element of a lens assembly such that the filter prevents the fluorescence excitation wavelength from irradiating the pixel array and allows a fluorescence relaxation wavelength of the reagent to irradiate the pixel array.

32. The endoscopic system of claim 1, wherein the pixel array detects a fluorescence relaxation wavelength and outputs fluorescence imaging data, wherein the fluorescence imaging data comprises information for identifying one or more critical structures in a human body.

33. The endoscopic system of claim 32, wherein the one or more critical structures in the human body comprises one of a nerve, a ureter, a blood vessel, an artery, a blood flow, or a tumor.

34. The endoscopic system of claim 32, wherein the one or more critical structures in the human body are cancer cells, and wherein the fluorescence relaxation wavelength is released by a reagent comprising a fluorophore that fluoresces when exposed to electromagnetic radiation having a wavelength between 770 nm and 815 nm.

35. The endoscopic system of claim 1, wherein the controller calculates the pulse cycle to comprise a fluorescence excitation emission that causes a reagent to fluoresce, and wherein the fluorescence excitation emission comprises electromagnetic radiation within a waveband from 770 nm to 815 nm.

36. The endoscopic system of claim 1, further comprising a filter that prevents electromagnetic radiation within a waveband from 770 nm to 815 nm from irradiating the pixel array of the image sensor.

37. The endoscopic system of claim 1, wherein the controller calculates the pulse cycle such that the plurality of pulses of electromagnetic radiation emitted by the light engine comprises a fluorescence excitation emission that causes a reagent to fluoresce, and wherein the fluorescence excitation emission comprises only electromagnetic radiation within a waveband from about 770 nm to about 815 nm.

38. The endoscopic system of claim 1, further comprising a filter that prevents electromagnetic radiation within a waveband from about 770 nm to about 790 nm from irradiating the pixel array of the image sensor.

39. The endoscopic system of claim 1, further comprising a filter that prevents electromagnetic radiation within a waveband from about 795 nm to about 815 nm from irradiating the pixel array of the image sensor.

40. The endoscopic system of claim 37, further comprising:
a first filter that prevents electromagnetic radiation between 770 nm and 790 nm from irradiating the pixel array of the image sensor; and
a second filter that prevents electromagnetic radiation between 795 nm and 815 nm from irradiating the pixel array of the image sensor.

41. The endoscopic system of claim 37, further comprising one or more filters that allow electromagnetic radiation between 790 nm and 800 nm and above 815 nm to pass through the one or more filters to the image sensor.

42. The endoscopic system of claim 1, wherein the image sensor comprises a first image sensor and a second image sensor, and wherein the dimensional information is calculated based on data output by the first image sensor and the second image sensor to produce a three-dimensional image.

43. The endoscopic system of claim 42, further comprising a filter that prevents the first image sensor from being irradiated by electromagnetic radiation having a wavelength less than 815 nm.

44. The endoscopic system of claim 42, further comprising a filter that prevents the second image sensor from being irradiated by electromagnetic radiation outside a waveband from 785 nm to 800 nm.

45. The endoscopic system of claim 42, further comprising:
one or more filters that prevent the first image sensor from being irradiated by electromagnetic radiation between 770 nm and 815 nm; and
one or more filters that prevent the second image sensor from being irradiated by electromagnetic radiation between 760 nm and 785 nm and electromagnetic radiation between 800 nm and 850 nm.

46. The endoscopic system of claim 1, further comprising a first filter that filters electromagnetic radiation between 770 nm and 815 nm.

47. The endoscopic system of claim 46, further comprising a second filter that filters electromagnetic radiation between 760 nm and 785 nm and electromagnetic radiation between 800 nm and 850 nm.

48. The endoscopic system of claim 1, wherein the two or more sources of electromagnetic radiation pulsed according to the pulse cycle comprises:
a visible source that pulses electromagnetic radiation within a visible waveband, wherein pulses by the visible source correspond with the image sensor outputting the color imaging data; and
one or more of the first spectral source or the second spectral source, wherein pulses by the one or more of the first spectral source or the second spectral source corresponding with the image sensor outputting fluorescence imaging data for identifying the target tissue with the algorithm.

49. The endoscopic system of claim 1, wherein the two or more sources of electromagnetic radiation pulsed according to the pulse cycle comprises:
a visible source that pulses electromagnetic radiation within a visible waveband, wherein pulses by the visible source correspond with the image sensor outputting the color imaging data; and a laser mapping source that pulses electromagnetic radiation diffracted into a laser map pattern, wherein pulses by the laser mapping source correspond with the image sensor outputting data for calculating the dimensional information.

50. The endoscopic system of claim 1, wherein the controller is further configured to:
    calculate an operational cycle for the image sensor that corresponds in time with the pulse cycle of the light engine; and
    instruct the image sensor to accumulate electromagnetic radiation and read out a plurality of exposure frames according to the operational cycle.

51. The endoscopic system of claim 50, wherein the controller is further configured to:
    receive an exposure frame output by the image sensor according to the operational cycle; and
    assign a datatype to the exposure frame based on when the pixel array detected the electromagnetic radiation for the exposure frame and further based on the pulse cycle of the light engine.

52. The endoscopic system of claim 51, wherein the controller is configured to assign a fluorescence datatype to the exposure frame in response to determining the pixel array detected the electromagnetic radiation when the light engine pulsed an excitation source of electromagnetic radiation.

53. The endoscopic system of claim 51, wherein the controller is configured to assign a multispectral datatype to the exposure frame in response to determining the pixel array detected the electromagnetic radiation when the light engine pulsed one or more of the first spectral source or the second spectral source.

54. The endoscopic system of claim 51, wherein the controller is configured to assign a laser mapping datatype to the exposure frame in response to determining the pixel array detected the electromagnetic radiation when the light engine pulsed electromagnetic radiation diffracted into a laser map pattern.

55. The endoscopic system of claim 51, wherein the controller is configured to assign a color datatype to the exposure frame in response to determining the pixel array detected the electromagnetic radiation when the light engine pulsed white light.

56. The endoscopic system of claim 51, wherein the pixel array comprises a color filter array, and wherein the image sensor outputs a plurality of exposure frames comprising a plurality of datatypes depending on which of the sources of electromagnetic radiation the light engine cycled on when the pixel array detected the electromagnetic radiation.

57. The endoscopic system of claim 56, wherein the plurality of datatypes comprises:
    a color datatype detected by the pixel array when the light engine cycled on a white light source;
    a fluorescence datatype detected by the pixel array when the light engine cycled on an excitation source of electromagnetic radiation selected to fluoresce a tissue or reagent;
    a multispectral datatype detected by the pixel array when the light engine cycled on one or more of the first spectral source or the second spectral source; and
    a laser mapping datatype detected by the pixel array when the light engine cycled on electromagnetic radiation diffracted into a laser map pattern.

* * * * *